(12) United States Patent
Stansfield et al.

(10) Patent No.: US 9,688,662 B2
(45) Date of Patent: Jun. 27, 2017

(54) N-(2,3-DIHYDRO-1H-PYRROLO[2,3-B]PYRIDIN-5-YL)-4-QUINAZOLINAMINE AND N-(2,3-DIHYDRO-1H-INDOL-5-YL)-4-QUINAZOLINAMINE DERIVATIVES AS PERK INHIBITORS

(71) Applicant: Janssen Pharmaceutica NV, Beerse (BE)

(72) Inventors: Ian Stansfield, Val de Reuil (FR); Yannick Aime Eddy Ligny, Val de Reuil (FR); Nathalie Claudie Isabelle Amblard, Val de Reuil (FR); Matthias Luc Aime Versele, Val de Reuil (FR)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/782,091

(22) PCT Filed: Mar. 31, 2014

(86) PCT No.: PCT/EP2014/056430
§ 371 (c)(1),
(2) Date: Oct. 2, 2015

(87) PCT Pub. No.: WO2014/161808
PCT Pub. Date: Oct. 9, 2014

(65) Prior Publication Data
US 2016/0039798 A1    Feb. 11, 2016

(30) Foreign Application Priority Data
Apr. 4, 2013   (EP) ..................... 13162362

(51) Int. Cl.
| | | |
|---|---|---|
| A61K 31/4045 | (2006.01) | |
| A61K 31/407 | (2006.01) | |
| A61K 31/517 | (2006.01) | |
| C07D 239/72 | (2006.01) | |
| C07D 403/12 | (2006.01) | |
| C07D 405/14 | (2006.01) | |
| C07D 413/14 | (2006.01) | |
| C07D 403/14 | (2006.01) | |
| C07D 409/14 | (2006.01) | |
| C07D 471/04 | (2006.01) | |
| C07D 491/056 | (2006.01) | |

(52) U.S. Cl.
CPC .......... *C07D 403/12* (2013.01); *A61K 31/407* (2013.01); *A61K 31/4045* (2013.01); *A61K 31/517* (2013.01); *C07D 239/72* (2013.01); *C07D 403/14* (2013.01); *C07D 405/14* (2013.01); *C07D 409/14* (2013.01); *C07D 413/14* (2013.01); *C07D 471/04* (2013.01); *C07D 491/056* (2013.01)

(58) Field of Classification Search
CPC .............. A61K 31/4045; A61K 31/407; A61K 31/517; C07D 239/72

USPC ......................................... 544/253; 514/258.1
See application file for complete search history.

(56) References Cited

U.S. PATENT DOCUMENTS

| | | |
|---|---|---|
| 5,747,498 A | 5/1998 | Schnur et al. |
| 2007/0287708 A1 | 12/2007 | Cole et al. |
| 2011/0288083 A1 | 11/2011 | Cardozo et al. |

FOREIGN PATENT DOCUMENTS

| | | | |
|---|---|---|---|
| EP | 566226 | 10/1993 | |
| WO | 9515758 A1 | 6/1995 | |
| WO | 9703069 A1 | 1/1997 | |
| WO | 03/051849 A1 | 6/2003 | |
| WO | 03/064399 A1 | 8/2003 | |
| WO | 2004/009601 A1 | 1/2004 | |
| WO | 2005070891 A3 | 10/2005 | |
| WO | 2009/130481 A1 | 10/2009 | |
| WO | 2011119663 A1 | 9/2011 | |
| WO | WO 2011119663 A1 * | 9/2011 | ........... A61K 31/405 |
| WO | 2012/069917 A1 | 5/2012 | |

OTHER PUBLICATIONS

Zhao, He, et al., "Indoline and Piperazine Containing Derivatives as a Novel Class of Mixed D2/D4 Receptor Antagonists. Part 1: Identification and Structure—Activity Relationships", Pergamon, Elsevier Science Ltd., Bioorganic & Medicinal Chemistry Letters, (2002) 3105-3109.

(Continued)

*Primary Examiner* — Kamal Saeed
*Assistant Examiner* — Janet L Coppins

(57) ABSTRACT

The present invention relates to N-(2,3-dihydro-1H-pyrrolo[2,3-b]pyridin-5-yl)-4-quinazolinamine and N-(2,3-dihydro-1H-indol-5-yl)-4-quinazolinamine derivatives of Formula (I)

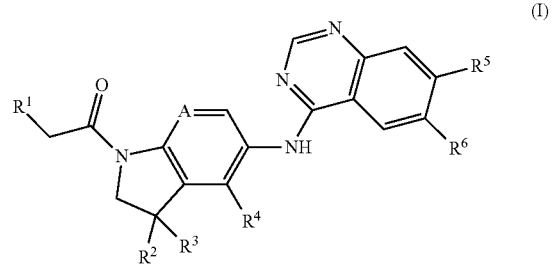

wherein $R^1$, $R^2$, $R^3$, $R^4$, $R^5$, $R^6$ and A have the meaning defined in the claims. The compounds according to the present invention are useful as inhibitors of PERK. The invention further relates to processes for preparing such compounds, pharmaceutical compositions comprising said compounds as an active ingredient as well as the use of said compounds as a medicament.

11 Claims, No Drawings

(56) References Cited

OTHER PUBLICATIONS

Bursavich, Matthew G., et al., "5'-Phenyl-3'H-spiro[indoline-3,2'[1,3,4]thiadiazol]-2-one inhibitors of ADAMTS-5 (Aggrecanase-2)", Elsevier, Science Diet, Bioorganic & Medicinal Chemistry Letters, (2007) 5630-5633.

Inman, Martyn, et al., "Indole synthesis—something old, something crew",Chemical Science, RSC Publishing, (2013) 4, 29-41.

Srinivas, B., et al,, "Synthesis and Screening of New Isatin Derivatives", Scholars Research Library, Der Pharma Chernica (2010), 2(6), 378-384.

Arico, Fabio, et al., "5-Membered N-heterocyclic compounds by dimethyl carbonate chemistry", Green Chemistry (2012) 14, 58-61.

Rad-Moghadam, Kurosh, et al., "One-pot Three-component Synthesis of 2-Substituted 4-Arninoguinazolines", Guilan University, Chemistry Department, J. Heterocyclic Chem (2006) 43, 913-916.

Jones, Terence R., et al., "Quinazoline Antifolates Inhibiting Thymidylate Synthase: 2-Desamino Derivatives with Enhanced Solubility and Potency", J. Med. Chem. (1969) 32, 847-852.

Wang, Zengxue, et al., "One-Pot Cyclization of 2-Arninophenethyl Alcohols: A Novel and Direct Approach to the Synthesis of N-Acyl indoilnes", J. Org. Chem., Department of Chemistry, Shanghai University, JOC Note, (2007), 72, 9364-9367.

Whelligan, Daniel K,, et al., "Two-Step Synthesis of Aza- and Diazaindoles from Chloroamino-N-heterocycles Using Ethoxyvinylborolane", Cancer Research UK Centre for Cancer Therapeutics, American Chemical Society, JOC Featured Article (2010), 75, 11-15.

Leroi, Corinne, et al., "Alkoxyamine-Mediated Radical Synthesis of Indolinones and Indolines", American Chemical Society, Organic Letters (2003) vol. 5, No, 26, 4943-4945.

Thibault, Carl,, et ai., "Concise and Efficient Synthesis of 4-Fluoro-1H-pyrroio[2,3-b]pyridine", American Chemical Society, Organic Letters (2003) vol. 5, No, 26, 5023-5025.

Huestis, Malcolm P. et al., "Site-Selective Azaindole Arylation at the Azine and Azole Rings via N-Oxide Activation", American Chemical Society, Organic Letters (2009) vol. 11, No. 6, 1357-1360.

Chandregowda, Venkateshappa, et ai., "Convergent Approach for Commercial Synthesis of Getitinib and Erlotinib", Vittal Mallya Scientific Research Foundation, Organic Process Research & Development, (2007) vol. 11, No. 5, 813-816.

Pearson, Stuart E., et al., "A Practical, Efficient Synthesis of 5-Amino-7-azaindole", AstraZeneca Pvt, Ltd., Advanced Online Publication (2005) No, 15, 2503-2506.

Chandrasekhar, Srivari, et al., "Palladium-Catalyzed Reduction of N-(tert-Butoxycarbonyi)indoles by Polymethylhydrosiloxane", Synthesis, (2007), No. 10, 1509-1512.

Torres, Jose C., et al,, "A Synthesis of 3-Fluoroindoles and 3,3-Difluoroindolines by Reduction of 3,3-Difluoro-2-oxindoles using a Borane Tetrahydrofuran Complex", Elsevier Science Ltd., Tetrahedron (1999) 55, 1881-1892.

Connolly, David J., et al., "Synthesis of quinazolinones and quinazolines", Elsevier Science Ltd., Tetrahedron (2005) 61, 10153-10202.

Cuny, Eckehard, et al., "Benzologs of Allopurinol: Synthesis of Pyrazolo [4,3-g] and [3,44] Quinazolinones1)", Tetrahedron Letters, (1980) vol. 21, 3029-3032.

Meister, Siike, et al,, "Extensive Immunoglobulin Production Sensitizes Myeloma Cells for Proteasome inhibition", Research Article, American Association for Cancer Research, (2007) 67 (4), 1783-1792.

Wang, Shiyu, et al., "The impact of the unfolded protein response on human disease", JCB:Review, J. Cell Biol., (2012), vol. 197, No. 7, 857-867.

Matsumoto, Masakatsu, et al., "A Facile One Step Synthesis of 4-Aminoindoles from 5-Halo-4-Oxo-4,5,6,7- Tetrahydroindoles", Heterocycles, (1986) vol. 24, No. 6.

Wang, Shu-Liang, et al,, "Green Synthesis of Quinazolinone Derivatives Catalyzed by Iodine in Ionic Liquid", School of Chemistry and Engineering, Synthetic Communications, (2012) 42, 341-349.

International Search Report and the Written Opinion of the International Searching Authority for Application No. PCT/EP2014/056430, filed Sep. 18, 2008. Date of Mailing Jun. 6, 2014.

* cited by examiner

N-(2,3-DIHYDRO-1H-PYRROLO[2,3-B] PYRIDIN-5-YL)-4-QUINAZOLINAMINE AND N-(2,3-DIHYDRO-1H-INDOL-5-YL)-4-QUINAZOLINAMINE DERIVATIVES AS PERK INHIBITORS

CROSS REFERENCE TO RELATED APPLICATIONS

This application is a national stage application of Patent Application No. PCT/EP2014/056430, filed 31 Mar. 2014, which claims the benefit of EP Patent Application No. 13162362.1, filed on 4 Apr. 2013, now abandoned. The complete disclosures of the aforementioned related patent applications are hereby incorporated herein by reference for all purposes.

FIELD OF THE INVENTION

The present invention relates to N-(2,3-dihydro-H-pyrrolo[2,3-b]pyridin-5-yl)-4-quinazolinamine and N-(2,3-dihydro-1H-indol-5-yl)-4-quinazolinamine derivatives, useful as PERK (PKR-like ER Kinase) inhibitors. The invention further relates to processes for preparing such compounds, pharmaceutical compositions comprising said compounds as an active ingredient as well as the use of said compounds as a medicament.

BACKGROUND OF THE INVENTION

Most secreted and membrane proteins are processed in the endoplasmic reticulum (ER). The influx of proteins into the ER is coordinated with the capacity of the ER by a stress response mechanism, called the unfolded protein response (UPR). The UPR consists of three branches to respond to accumulation of unfolded protein within the lumen of the ER: IRE1/ERN1, PERK/EIF2AK3, and ATF6 (Walter et al., Science 2011, 334(6059): 1081-6). Whereas both ATF6 and IRE1 mainly increase the capacity of the ER by increasing transcription of ER chaperones, lipid synthesis genes and components of the ER-associated degradation (ERAD) machinery, PERK reduces de novo protein synthesis by directly phosphorylating eukaryotic initiation factor 2 alpha (eIF2alpha), thereby inhibiting global protein initiation. The UPR functions to restore ER homeostasis, and thus serves as a cellular survival mechanism under most physiologic ER stress conditions. However, under severe and unresolvable ER stress, the UPR can promote apoptosis through induction of the pro-apoptotic factor, CHOP (C/EBP homologous protein; GADD153).

Aberrant activation of the unfolded protein response has been implicated in a wide variety of pathologies as recently reviewed by Wang et al. (J. Cell Biol 2012, 197(7):857-67). Inhibition of the PERK-branch of the unfolded protein response relieves PERK-mediated protein translation inhibition, and hence derepresses protein synthesis under ER stress. This may be therapeutically useful in diseases associated with activation of the UPR, such as cancer, in particular secretory cancer types, diabetes (e.g. type 1 diabetes), obesity, ocular diseases, stroke, myocardial infarction, cardiovascular disease, atherosclerosis, arrhythmias, viral infectious and inflammatory diseases, and neurodegenerative diseases (such as amyotrophic lateral sclerosis, prion-related diseases, Huntington's, Alzheimer's and Parkinson's disease), and the like. An application of UPR-mediated cell death, is the efficacy of proteasome inhibitors (such as bortezomib/Velcade®) in the treatment of multiple myeloma: these malignant plasma cells are characterized by a high secretory burden due to constitutive secretion of immunoglobulins, and are exquisitely sensitive to inhibition of proteaseome activity which overwhelms the ER with unfolded proteins, and leads to CHOP-mediated apoptosis (Meister et al., Canc Res 2007, 67(4):1783-92).

WO 95/15758 describes the preparation of (hetero)arylquinazolines which inhibit CSF-1R receptor tyrosine kinase;

WO 97/03069 discloses heterocyclyl-substituted quinazolines as protein tyrosine kinase inhibitors;

WO 2005/070891 describes a class of compounds useful in treating cancer and angiogenesis;

WO 2011/119663 is directed to substituted indoline derivatives which are inhibitors of PERK.

There is a strong need for novel compounds which inhibit PERK kinase activity, thereby opening new avenues for the treatment or prevention of cancer, in particular secretory cancer types, diabetes (e.g. type 1 diabetes), obesity, ocular diseases, stroke, myocardial infarction, cardiovascular disease, atherosclerosis, arrhythmias, viral infectious and inflammatory diseases, and neurodegenerative diseases (such as amyotrophic lateral sclerosis, prion-related diseases, Huntington's, Alzheimer's and Parkinson's disease), and the like. It is accordingly an object of the present invention to provide such compounds.

The present invention is concerned with a chemical series of potent and selective inhibitors of PERK. These compounds are kinase-selective, not only compared to more than 400 unrelated kinases but also compared to the closely related eIF2alpha kinase family members, GCN2 and PKR. These compounds inhibit phosphorylation of eIF2α at 10-20 nM ($IC_{50}$) in HEK293 cells, incubated with the ER stressor tunicamycin. These PERK inhibitors are selectively antiproliferative in an ER-stressed epithelial cancer model (A549 cells with tunicamycin) at nM concentrations, but to a lesser extent in the absence of ER stress, illustrating the selectivity of these molecules in a cellular model. Furthermore, in the absence of an exogenous ER stressor, these PERK inhibitors induced ER stress (eg, as evidenced by induction of the pro-apoptotic CHOP gene) selectively in multiple myeloma cell lines and certain B-cell lymphoma cell lines (e.g. diffuse large B-cell lymphoma, mantle cell lymphoma, follicular lymphoma) at low nM concentrations, confirming the intrinsic sensitivity of multiple myeloma and B-cell lymphoma models to ER stress. The magnitude of this induction by PERK inhibitors was comparable to well-established ER stressors, such as tunicamycin, and correlated closely with reduced proliferation in malignant B-cell lines. In the tests performed, it was found that the induction of ER stress was maximal at a dose corresponding to approximately 50-75% inhibition of PERK.

SUMMARY OF THE INVENTION

It has been found that the compounds of the present invention are useful as PERK inhibitors. The compounds according to the invention and compositions thereof, may be useful for the treatment or prevention, in particular for the treatment, of cancer, in particular secretory cancer types, diabetes (e.g. type 1 diabetes), obesity, ocular diseases, stroke, myocardial infarction, cardiovascular disease, atherosclerosis, arrhythmias, viral infectious and inflammatory diseases, and neurodegenerative diseases (such as amyotrophic lateral sclerosis, prion-related diseases, Huntington's, Alzheimer's and Parkinson's disease), and the like.

The present invention concerns novel compounds of Formula (I)

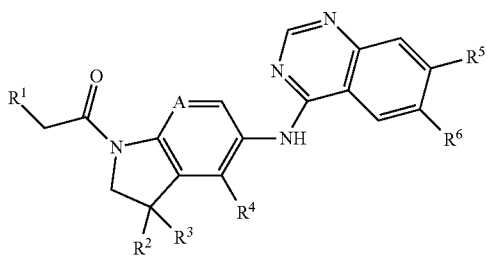

tautomers and stereoisomeric forms thereof, wherein
$R^1$ is —$Ar^1$, —O—$Ar^1$ or —NH—$Ar^1$;
$Ar^1$ is phenyl, pyridinyl, indazolyl, pyrazolyl, indolyl, imidazolyl, benzimidazolyl, thienyl, quinazolinyl, benzo[b]thienyl, benzofuranyl, 1H-pyrrolo[2,3-b]pyridinyl, imidazo[1,2-a]pyridinyl, 1,3-dihydro-1-oxo-2H-isoindolyl, 1,3-dihydro-1,3-dioxo-2H-isoindolyl, naphthyl, isoquinolinyl, quinolinyl, cinnolinyl, furanyl or 2,3-dihydro-2-oxo-1H-benzimidazolyl;
  each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ and $C_{1-4}$alkyl substituted with one or more halo atoms;
$Ar^2$ is phenyl, thienyl, furanyl, isoxazolyl, oxazolyl or pyrazolyl; each optionally substituted with 1, 2 or 3 $C_{1-4}$alkyl groups;
$R^2$ and $R^3$ are the same and are hydrogen or fluoro;
A is CH or N;
$R^4$ is hydrogen, chloro or fluoro;
$R^5$ is hydrogen, —$OR^7$ or —O—$(CH_2)_m$—O—$R^7$;
$R^6$ is hydrogen, —$OR^8$ or —O—$(CH_2)_m$—O—$R^8$;
provided that at least one of $R^5$ and $R^6$ is not hydrogen;
or $R^5$ and $R^6$ are taken together to form the bivalent radical —O—$(CH_2)_n$—O—;
n is 1, 2 or 3;
m is 1, 2, 3 or 4;
$R^7$ is $C_{1-4}$alkyl optionally substituted with one $NR^{9a}R^{10a}$;
$R^8$ is $C_{1-4}$alkyl optionally substituted with one $NR^{9b}R^{10b}$;
$R^{9a}$ and $R^{10a}$ each independently are hydrogen or $C_{1-4}$alkyl;
  or $R^{9a}$ and $R^{10a}$ are taken together with the nitrogen to which they are attached to form a saturated monocyclic 4, 5, 6 or 7-membered heterocycle which may further contain one additional heteroatom selected from O, S, S(=O)$_p$ or N; and which heterocycle may optionally be substituted with 1, 2 or 3 substituents each independently selected from the group consisting of halo and $C_{1-4}$alkyl;
$R^{9b}$ and $R^{10b}$ each independently are hydrogen or $C_{1-4}$alkyl;
  or $R^{9b}$ and $R^{10b}$ are taken together with the nitrogen to which they are attached to form a saturated monocyclic 4, 5, 6 or 7-membered heterocycle which may further contain one additional heteroatom selected from O, S, S(=O)$_p$ or N; and which heterocycle may optionally be substituted with 1, 2 or 3 substituents each independently selected from the group consisting of halo and $C_{1-4}$alkyl;
p is 1 or 2;
and pharmaceutically acceptable addition salts, and solvates thereof.

The present invention also concerns methods for the preparation of compounds of the present invention and pharmaceutical compositions comprising them.

The compounds of the present invention were found to inhibit PERK, and therefore may be useful in the treatment or prevention, in particular in the treatment, of cancer, in particular secretory cancer types, diabetes (e.g. type 1 diabetes), obesity, ocular diseases, stroke, myocardial infarction, cardiovascular disease, atherosclerosis, arrhythmias, viral infectious and inflammatory diseases, and neurodegenerative diseases (such as amyotrophic lateral sclerosis, prion-related diseases, Huntington's, Alzheimer's and Parkinson's disease), and the like.

In view of the aforementioned pharmacology of the compounds of Formula (I) and pharmaceutically acceptable addition salts, and solvates thereof, it follows that they may be suitable for use as a medicament.

In particular the compounds of Formula (I) and pharmaceutically acceptable addition salts, and solvates thereof, may be suitable in the treatment or prevention, in particular in the treatment, of cancer, in particular secretory cancer types.

The present invention also concerns the use of compounds of Formula (I) and pharmaceutically acceptable addition salts, and solvates thereof, for the manufacture of a medicament for the inhibition of PERK, for the treatment or prevention of cancer.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

Whenever the term "substituted" is used in the present invention, it is meant, unless otherwise is indicated or is clear from the context, to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "halo" as a group or part of a group is generic for fluoro, chloro, bromo, iodo unless otherwise is indicated or is clear from the context.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes methyl, ethyl, n-propyl, i-propyl, 2-methyl-ethyl, butyl and its isomers (e.g. n-butyl, isobutyl and tert-butyl), and the like.

The term "$C_{1-4}$alkyloxy" as a group or part of a group refers to a radical having the Formula $OR^b$ wherein $R^b$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The chemical names of the intermediates and compounds were generated according to the nomenclature rules agreed upon by the International Union of Pure and Applied Chemistry (IUPAC), using Symyx draw (version 4.0) (Accelrys©, Inc.).

The heterocycles in the $Ar^1$ or $Ar^2$ definition are meant to include all the possible isomeric forms of the heterocycles.

The carbocycles or heterocycles covered by for instance the terms $Ar^1$ or $Ar^2$ may be attached to the remainder of the molecule of Formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like, or when the carbocycle is naphthyl, it may be 1-naphthyl, 2-naphthyl and the like.

The term "compounds of the invention" as used herein, is meant to include the compounds of Formula (I) and pharmaceutically acceptable addition salts, and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Whenever one of the ring systems in the definition of $Ar^1$, $Ar^2$, or the saturated monocyclic heterocycle formed by taking $R^{9a}$ and $R^{10a}$ or $R^{9b}$ and $R^{10b}$ together, is substituted with one or more substituents, those substituents may replace any hydrogen atom bound to a carbon or nitrogen atom of the ring system.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds of Formula (I) may also exist in their tautomeric form. Such forms in so far as they may exist, are intended to be included within the scope of the present invention.

It follows that a single compound may exist in both stereoisomeric and tautomeric form.

For therapeutic use, salts of the compounds of Formula (I) and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove or hereinafter are meant to comprise the therapeutically active non-toxic acid and base addition salt forms which the compounds of Formula (I) and solvates thereof, are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as pharmaceutically acceptable addition salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I) and pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, an element, in particular when mentioned in relation to a compound of Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

As used in the specification and the appended claims, the singular forms "a", "an" and "the" also include plural referents unless the context clearly dictates otherwise. For example, "a compound" means 1 compound or more than 1 compound.

In an embodiment, the present invention concerns novel compounds of Formula (I), tautomers and stereoisomeric forms thereof, wherein
$R^1$ is —$Ar^1$, —O—$Ar^1$ or —NH—$Ar^1$;
$Ar^1$ is phenyl, pyridinyl, indazolyl, pyrazolyl, indolyl, imidazolyl, benzimidazolyl, thienyl, benzo[b]thienyl, benzofuranyl, 1H-pyrrolo[2,3-b]pyridinyl, imidazo[1,2-a]pyridinyl, 1,3-dihydro-1-oxo-2H-isoindolyl, 1,3-dihydro-1,3-dioxo-2H-isoindolyl or 2,3-dihydro-2-oxo-1H-benzimidazolyl;
each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ and $C_{1-4}$alkyl substituted with one or more halo atoms;
$Ar^2$ is phenyl, thienyl, furanyl, isoxazolyl or pyrazolyl; each optionally substituted with 1, 2 or 3 $C_{1-4}$alkyl groups;
$R^2$ and $R^3$ are the same and are hydrogen or fluoro;
A is CH or N;
$R^4$ is hydrogen, chloro or fluoro;
$R^5$ is hydrogen, —$OR^7$ or —O—$(CH_2)_m$—O—$R^7$;
$R^6$ is hydrogen, —$OR^8$ or —O—$(CH_2)_m$—O—R;
provided that at least one of $R^5$ and $R^6$ is not hydrogen;
or $R^5$ and $R^6$ are taken together to form the bivalent radical —O—$(CH_2)_n$—O—;
n is 1, 2 or 3;
m is 1, 2, 3 or 4;
$R^7$ is $C_{1-4}$alkyl optionally substituted with one $NR^{9a}R^{10a}$;
$R^8$ is $C_{1-4}$alkyl optionally substituted with one $NR^{9b}R^{10b}$;
$R^{9a}$ and $R^{10a}$ each independently are hydrogen or $C_{1-4}$alkyl; or $R^{9a}$ and $R^{10a}$ are taken together with the nitrogen to which they are attached to form a saturated monocyclic 4, 5, 6 or 7-membered heterocycle which may further contain one additional heteroatom selected from O, S, S(=O)$_p$ or N; and which heterocycle may optionally be substituted with 1, 2 or 3 substituents each independently selected from the group consisting of halo and $C_{1-4}$alkyl;
$R^{9b}$ and $R^{10b}$ each independently are hydrogen or $C_{1-4}$alkyl; or $R^{9b}$ and $R^{10b}$ are taken together with the nitrogen to which they are attached to form a saturated monocyclic 4, 5, 6 or 7-membered heterocycle which may further contain one additional heteroatom selected from O, S, S(=O)$_p$ or N; and which heterocycle may optionally be substituted with 1, 2 or 3 substituents each independently selected from the group consisting of halo and $C_{1-4}$alkyl;
p is 1 or 2;
and pharmaceutically acceptable addition salts, and solvates thereof.

In an embodiment, the present invention concerns novel compounds of Formula (I), tautomers and stereoisomeric forms thereof, wherein
$R^1$ is —$Ar^1$, —O—$Ar^1$ or —NH—$Ar^1$;
$Ar^1$ is phenyl, pyridinyl, indazolyl, pyrazolyl, indolyl, benzimidazolyl, thienyl, benzo[b]thienyl, benzofuranyl, 1H-pyrrolo[2,3-b]pyridinyl, imidazo[1,2-a]pyridinyl, 1,3-dihydro-1-oxo-2H-isoindolyl, 1,3-dihydro-1,3-dioxo-2H-isoindolyl or 2,3-dihydro-2-oxo-1H-benzimidazolyl;
each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ and $C_{1-4}$alkyl substituted with one or more halo atoms;
$Ar^2$ is phenyl, thienyl, furanyl, isoxazolyl, oxazolyl or pyrazolyl; each optionally substituted with 1, 2 or 3 $C_{1-4}$alkyl groups;
$R^2$ and $R^3$ are the same and are hydrogen or fluoro;
A is CH or N;
$R^4$ is hydrogen, chloro or fluoro;
$R^5$ is hydrogen, —$OR^7$ or —O—$(CH_2)_m$—O—$R^7$;
$R^6$ is hydrogen, —$OR^8$ or —O—$(CH_2)_m$—O—$R^8$;
provided that at least one of $R^5$ and $R^6$ is not hydrogen;
n is 1, 2 or 3;
m is 1, 2, 3 or 4;
$R^7$ is $C_{1-4}$alkyl optionally substituted with one $NR^{9a}R^{10a}$;
$R^8$ is $C_{1-4}$alkyl optionally substituted with one $NR^{9b}R^{10b}$;

$R^{9a}$ and $R^{10a}$ each independently are hydrogen or $C_{1-4}$alkyl; or $R^{9a}$ and $R^{10a}$ are taken together with the nitrogen to which they are attached to form a saturated monocyclic 4, 5, 6 or 7-membered heterocycle which may further contain one additional heteroatom selected from O, S, $S(=O)_p$ or N; and which heterocycle may optionally be substituted with 1, 2 or 3 substituents each independently selected from the group consisting of halo and $C_{1-4}$alkyl;

$R^{9b}$ and $R^{10b}$ each independently are hydrogen or $C_{1-4}$alkyl; or $R^{9b}$ and $R^{10b}$ are taken together with the nitrogen to which they are attached to form a saturated monocyclic 4, 5, 6 or 7-membered heterocycle which may further contain one additional heteroatom selected from O, S, $S(=O)_p$ or N; and which heterocycle may optionally be substituted with 1, 2 or 3 substituents each independently selected from the group consisting of halo and $C_{1-4}$alkyl;

p is 1 or 2;

and pharmaceutically acceptable addition salts, and solvates thereof.

In an embodiment, the present invention concerns novel compounds of Formula (I), tautomers and stereoisomeric forms thereof, wherein $R^1$ is —$Ar^1$, —O—$Ar^1$ or —NH—$Ar^1$;

$Ar^1$ is phenyl, pyridinyl, indazolyl, pyrazolyl, indolyl, benzimidazolyl, thienyl, benzo[b]thienyl, benzofuranyl, 1H-pyrrolo[2,3-b]pyridinyl, imidazo[1,2-a]pyridinyl, or 2,3-dihydro-2-oxo-1H-benzimidazolyl;

each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ and $C_{1-4}$alkyl substituted with one or more halo atoms;

$Ar^2$ is phenyl, thienyl, furanyl, isoxazolyl or pyrazolyl; each optionally substituted with 1, 2 or 3 $C_{1-4}$alkyl groups;

$R^2$ and $R^3$ are the same and are hydrogen or fluoro;

A is CH or N;

$R^4$ is hydrogen, chloro or fluoro;

$R^5$ is hydrogen, —$OR^7$ or —O—$(CH_2)_m$—O—$R^7$;

$R^6$ is hydrogen, —$OR^8$ or —O—$(CH_2)_m$—O—R;

provided that at least one of $R^5$ and $R^6$ is not hydrogen;

or $R^5$ and $R^6$ are taken together to form the bivalent radical —O—$(CH_2)_n$—O—;

n is 1, 2 or 3;

m is 1, 2, 3 or 4;

$R^7$ is $C_{1-4}$alkyl optionally substituted with one $NR^{9a}R^{10a}$;

$R^8$ is $C_{1-4}$alkyl optionally substituted with one $NR^{9b}R^{10b}$;

$R^{9a}$ and $R^{10a}$ each independently are hydrogen or $C_{1-4}$alkyl; or $R^{9a}$ and $R^{10a}$ are taken together with the nitrogen to which they are attached to form a saturated monocyclic 4, 5, 6 or 7-membered heterocycle which may further contain one additional heteroatom selected from O, S, $S(=O)_p$ or N; and which heterocycle may optionally be substituted with 1, 2 or 3 substituents each independently selected from the group consisting of halo and $C_{1-4}$alkyl;

$R^{9b}$ and $R^{10b}$ each independently are hydrogen or $C_{1-4}$alkyl; or $R^{9b}$ and $R^{10b}$ are taken together with the nitrogen to which they are attached to form a saturated monocyclic 4, 5, 6 or 7-membered heterocycle which may further contain one additional heteroatom selected from O, S, $S(=O)_p$ or N; and which heterocycle may optionally be substituted with 1, 2 or 3 substituents each independently selected from the group consisting of halo and $C_{1-4}$alkyl;

p is 1 or 2;

and pharmaceutically acceptable addition salts, and solvates thereof.

In an embodiment, the present invention concerns novel compounds of Formula (I), tautomers and stereoisomeric forms thereof, wherein $R^1$ is —$Ar^1$;

$Ar^1$ is phenyl, pyridinyl, indazolyl, pyrazolyl, indolyl, benzimidazolyl, thienyl, benzo[b]thienyl, benzofuranyl, 1H-pyrrolo[2,3-b]pyridinyl, imidazo[1,2-a]pyridinyl, or 2,3-dihydro-2-oxo-1H-benzimidazolyl;

each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ and $C_{1-4}$alkyl substituted with one or more halo atoms;

$Ar^2$ is phenyl, thienyl, furanyl, isoxazolyl, or pyrazolyl; each optionally substituted with 1, 2 or 3 $C_{1-4}$alkyl groups;

$R^2$ and $R^3$ are the same and are hydrogen or fluoro; in particular hydrogen;

A is CH;

$R^4$ is hydrogen or fluoro;

$R^5$ is —OR;

$R^6$ is —$OR^8$;

or $R^5$ and $R^6$ are taken together to form the bivalent radical —O—$CH_2$—O—;

$R^7$ is $C_{1-4}$alkyl;

$R^8$ is $C_{1-4}$alkyl optionally substituted with one morpholinyl;

and pharmaceutically acceptable addition salts, and solvates thereof.

In an embodiment, the present invention concerns novel compounds of Formula (I), tautomers and stereoisomeric forms thereof, wherein $R^1$ is —$Ar^1$, —O—$Ar^1$ or —NH—$Ar^1$;

$Ar^1$ is phenyl, pyridinyl, indazolyl, pyrazolyl, indolyl, imidazolyl, benzimidazolyl, thienyl, quinazolinyl, benzo[b]thienyl, benzofuranyl, 1H-pyrrolo[2,3-b]pyridinyl, imidazo[1,2-a]pyridinyl, 1,3-dihydro-1-oxo-2H-isoindolyl, 1,3-dihydro-1,3-dioxo-2H-isoindolyl, naphthyl, isoquinolinyl, quinolinyl, cinnolinyl, furanyl or 2,3-dihydro-2-oxo-1H-benzimidazolyl;

each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ or $C_{1-4}$alkyl substituted with one or more halo atoms;

$Ar^2$ is phenyl, thienyl, furanyl, isoxazolyl, oxazolyl or pyrazolyl; each optionally substituted with 1, 2 or 3 $C_{1-4}$alkyl groups;

$R^2$ and $R^3$ are the same and are hydrogen or fluoro;

A is CH or N;

$R^4$ is hydrogen, chloro or fluoro;

$R^5$ is hydrogen or —$OR^7$;

$R^6$ is hydrogen or —$OR^8$;

provided that at least one of $R^5$ and $R^6$ is not hydrogen;

or $R^5$ and $R^6$ are taken together to form the bivalent radical —O—$(CH_2)_n$—O—;

n is 1, 2 or 3;

$R^7$ is $C_{1-4}$alkyl;

$R^8$ is $C_{1-4}$alkyl;

and pharmaceutically acceptable addition salts, and solvates thereof.

In an embodiment, the present invention concerns novel compounds of Formula (I), tautomers and stereoisomeric forms thereof, wherein $R^1$ is —$Ar^1$;

$Ar^1$ is phenyl or indolyl; in particular phenyl, indol-1-yl or indol-3-yl;

each optionally substituted with 1 or 2 substituents each independently selected from the group consisting of $C_{1-4}$alkyl and halo; in particular each optionally substituted with 1 or 2 substituents each independently selected from the group consisting of methyl and fluoro;
$R^2$ and $R^3$ are the same and are hydrogen;
A is CH;
$R^4$ is hydrogen or fluoro;
$R^5$ is methoxy;
$R^6$ is $OR^8$;
$R^8$ is $C_{1-4}$alkyl optionally substituted with one morpholinyl; in particular $R^8$ is methyl or

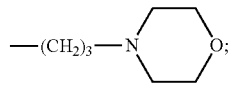

and pharmaceutically acceptable addition salts, and solvates thereof.

In an embodiment, the present invention concerns novel compounds of Formula (I), tautomers and stereoisomeric forms thereof, wherein
$R^1$ is —$Ar^1$;
$Ar^1$ is phenyl or indolyl; in particular phenyl or indol-3-yl;
  each optionally substituted with 1 or 2 substituents each independently selected from the group consisting of $C_{1-4}$alkyl and halo; in particular each optionally substituted with 1 or 2 substituents each independently selected from the group consisting of methyl and fluoro;
$R^2$ and $R^3$ are the same and are hydrogen;
A is CH;
$R^4$ is hydrogen or fluoro;
$R^5$ is methoxy;
$R^6$ is methoxy;
and pharmaceutically acceptable addition salts, and solvates thereof In an embodiment, the present invention concerns novel compounds of Formula (I), tautomers and stereoisomeric forms thereof, wherein
$R^1$ is —$Ar^1$ or —O—$Ar^1$;
$Ar^1$ is phenyl, pyridinyl, indazolyl, pyrazolyl, indolyl, imidazolyl, benzimidazolyl, thienyl, benzo[b]thienyl, benzofuranyl, 1H-pyrrolo[2,3-b]pyridinyl, imidazo[1,2-a]pyridinyl, 1,3-dihydro-1-oxo-2H-isoindolyl, 1,3-dihydro-1,3-dioxo-2H-isoindolyl or 2,3-dihydro-2-oxo-1H-benzimidazolyl;
  each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ and $C_{1-4}$alkyl substituted with one or more halo atoms;
$Ar^2$ is phenyl, thienyl, furanyl, isoxazolyl or pyrazolyl; each optionally substituted with one $C_{1-4}$alkyl group;
$R^2$ and $R^3$ are the same and are hydrogen or fluoro;
A is CH or N;
$R^4$ is hydrogen or fluoro;
$R^5$ is hydrogen, —$OR^7$ or —O—$(CH_2)_m$—O—$C_{1-4}$alkyl;
$R^6$ is —$OR^8$ or —O—$(CH_2)_m$—O—$C_{1-4}$alkyl;
or $R^5$ and $R^6$ are taken together to form the bivalent radical —O—$CH_2$—O—;
m is 1, 2, 3 or 4;
$R^7$ is $C_{1-4}$alkyl;
$R^8$ is $C_{1-4}$alkyl optionally substituted with one $NR^{9b}R^{10b}$;
$R^{9b}$ and $R^{10b}$ are taken together with the nitrogen to which they are attached to form morpholinyl;
and pharmaceutically acceptable addition salts, and solvates thereof.

In an embodiment, the present invention concerns novel compounds of Formula (I), tautomers and stereoisomeric forms thereof, wherein
$R^1$ is —$Ar^1$ or —O—$Ar^1$;
$Ar^1$ is phenyl, 2-pyridinyl, indazol-1-yl, indazol-3-yl, pyrazol-3-yl, pyrazol-5-yl, indol-1-yl, indol-2-yl, indol-3-yl, imidazol-1-yl, benzimidazol-1-yl, 2-thienyl, 3-thienyl, benzo[b]thien-3-yl, 3-benzofuranyl, 1H-pyrrolo[2,3-b]pyridin-3-yl, imidazo[1,2-a]pyridin-3-yl, 1,3-dihydro-1-oxo-2H-isoindol-2-yl, 1,3-dihydro-1,3-dioxo-2H-isoindol-2-yl or 2,3-dihydro-2-oxo-1H-benzimidazol-1-yl;
  each optionally substituted with 1, 2 or 3 substituents each independently selected from the group consisting of methyl, methylcarbonyl, methoxy, F, Br, $Ar^2$ and $C_{1-4}$alkyl substituted with one or more F atoms;
$Ar^2$ is phenyl, 2-thienyl, 3-thienyl, 3-furanyl, 4-isoxazolyl or pyrazol-4-yl; each optionally substituted with one methyl group;
$R^2$ and $R^3$ are the same and are hydrogen or fluoro;
A is CH or N;
$R^4$ is hydrogen or fluoro;
$R^5$ is hydrogen, —$OR^7$ or —O—$(CH_2)_m$—O—$CH_3$;
$R^6$ is —$OR^8$ or —O—$(CH_2)_m$—O—$CH_3$;
or $R^5$ and $R^6$ are taken together to form the bivalent radical —O—$CH_2$—O—;
m is 1, 2, 3 or 4;
$R^7$ is methyl;
$R^8$ is methyl optionally substituted with one $NR^{9b}R^{10b}$;
$R^{9b}$ and $R^{10b}$ are taken together with the nitrogen to which they are attached to form morpholinyl;
and pharmaceutically acceptable addition salts, and solvates thereof.

In an embodiment, the present invention relates to those compounds of Formula (I) and pharmaceutically acceptable addition salts, and solvates thereof, or any subgroup thereof as mentioned in any of the other embodiments, wherein $R^1$ is —$Ar^1$.

In an embodiment, the present invention relates to those compounds of Formula (I) and pharmaceutically acceptable addition salts, and solvates thereof, or any subgroup thereof as mentioned in any of the other embodiments, wherein $Ar^1$ is phenyl, indol-1-yl or indol-3-yl each optionally substituted as specified in any of the other embodiments.

In an embodiment, the present invention relates to those compounds of Formula (I) and pharmaceutically acceptable addition salts, and solvates thereof, or any subgroup thereof as mentioned in any of the other embodiments, wherein $R^1$ is —$Ar^1$ and $Ar^1$ is phenyl, indol-1-yl or indol-3-yl each optionally substituted as specified in any of the other embodiments.

In an embodiment, the present invention relates to those compounds of Formula (I) and pharmaceutically acceptable addition salts, and solvates thereof, or any subgroup thereof as mentioned in any of the other embodiments, wherein $R^1$ is —$Ar^1$; and $Ar^1$ is phenyl or indolyl each optionally substituted as specified in any of the other embodiments.

In an embodiment, the present invention relates to those compounds of Formula (I) and pharmaceutically acceptable addition salts, and solvates thereof, or any subgroup thereof as mentioned in any of the other embodiments, wherein $R^{9a}$ and $R^{10a}$ each independently are hydrogen or $C_{1-4}$alkyl; or $R^{9a}$ and $R^{10a}$ are taken together with the nitrogen to which they are attached to form morpholinyl.

In an embodiment, the present invention relates to those compounds of Formula (I) and pharmaceutically acceptable addition salts, and solvates thereof, or any subgroup thereof as mentioned in any of the other embodiments, wherein $R^{9b}$ and $R^{10b}$ each independently are hydrogen or $C_{1-4}$alkyl; or $R^{9b}$ and $R^{10b}$ are taken together with the nitrogen to which they are attached to form morpholinyl.

In an embodiment, the present invention relates to those compounds of Formula (I) and pharmaceutically acceptable addition salts, and solvates thereof, or any subgroup thereof as mentioned in any of the other embodiments, wherein $R^1$ is —$Ar^1$; $Ar^1$ is phenyl, pyridinyl, indazolyl, pyrazolyl, indolyl, imidazolyl, benzimidazolyl, thienyl, quinazolinyl, benzo[b]thienyl, benzofuranyl, 1H-pyrrolo[2,3-b]pyridinyl, imidazo[1,2-a]pyridinyl, 1,3-dihydro-1-oxo-2H-isoindolyl, 1,3-dihydro-1,3-dioxo-2H-isoindolyl, or 2,3-dihydro-2-oxo-1H-benzimidazolyl; each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ or $C_{1-4}$alkyl substituted with one or more halo atoms.

In an embodiment, the present invention relates to those compounds of Formula (I) and pharmaceutically acceptable addition salts, and solvates thereof, or any subgroup thereof as mentioned in any of the other embodiments, wherein $R^1$ is —O—$Ar^1$ or —NH—$Ar^1$; in particular —O—$Ar^1$.

In an embodiment, the present invention relates to those compounds of Formula (I) and pharmaceutically acceptable addition salts, and solvates thereof, or any subgroup thereof as mentioned in any of the other embodiments, wherein $R^1$ is —NH—$Ar^1$.

In an embodiment, the present invention relates to those compounds of Formula (I) and pharmaceutically acceptable addition salts, and solvates thereof, or any subgroup thereof as mentioned in any of the other embodiments, wherein $Ar^1$ is phenyl, pyridinyl, indazolyl, pyrazolyl, indolyl, imidazolyl, benzimidazolyl, thienyl, benzo[b]thienyl, benzofuranyl, 1H-pyrrolo[2,3-b]pyridinyl, imidazo[1,2-a]pyridinyl, 1,3-dihydro-1-oxo-2H-isoindolyl, 1,3-dihydro-1,3-dioxo-2H-isoindolyl, or 2,3-dihydro-2-oxo-1H-benzimidazolyl; each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ or $C_{1-4}$alkyl substituted with one or more halo atoms.

In an embodiment, the present invention relates to those compounds of Formula (I) and pharmaceutically acceptable addition salts, and solvates thereof, or any subgroup thereof as mentioned in any of the other embodiments, wherein $Ar^1$ is phenyl, pyridinyl, indazolyl, pyrazolyl, indolyl, benzimidazolyl, thienyl, benzo[b]thienyl, benzofuranyl, 1H-pyrrolo[2,3-b]pyridinyl, imidazo[1,2-a]pyridinyl, or 2,3-dihydro-2-oxo-1H-benzimidazolyl;
each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ and $C_{1-4}$alkyl substituted with one or more halo atoms.

In an embodiment, the present invention relates to those compounds of Formula (I) and pharmaceutically acceptable addition salts, and solvates thereof, or any subgroup thereof as mentioned in any of the other embodiments, wherein $Ar^1$ is phenyl, indazolyl, pyrazolyl, indolyl, thienyl, benzo[b]thienyl, benzofuranyl or imidazo[1,2-a]pyridinyl;
each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ and $C_{1-4}$alkyl substituted with one or more halo atoms; in particular each optionally substituted with 1, 2 or 3 substituents each independently selected from the group consisting of $C_{1-4}$alkyl, halo, $C_{1-4}$alkyloxy and $C_{1-4}$alkyl substituted with one or more halo atoms.

In an embodiment, the present invention relates to those compounds of Formula (I) and pharmaceutically acceptable addition salts, and solvates thereof, or any subgroup thereof as mentioned in any of the other embodiments, wherein $Ar^1$ is phenyl, pyridinyl, indazolyl, pyrazolyl, indolyl, imidazolyl, benzimidazolyl, thienyl, benzo[b]thienyl, benzofuranyl, 1H-pyrrolo[2,3-b]pyridinyl, imidazo[1,2-a]pyridinyl, 1,3-dihydro-1-oxo-2H-isoindolyl, 1,3-dihydro-1,3-dioxo-2H-isoindolyl, or 2,3-dihydro-2-oxo-1H-benzimidazolyl;
each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ and $C_{1-4}$alkyl substituted with one or more halo atoms;
provided that when $Ar^1$ is indazolyl, indolyl, benzimidazolyl, benzo[b]thienyl, benzofuranyl, 1H-pyrrolo[2,3-b]pyridinyl, imidazo[1,2-a]pyridinyl, 1,3-dihydro-1-oxo-2H-isoindolyl, 1,3-dihydro-1,3-dioxo-2H-isoindolyl, or 2,3-dihydro-2-oxo-1H-benzimidazolyl, said bicyclic radical is attached to the remainder of the molecule with the 5-membered ring.

In an embodiment, the bicyclic radicals indazolyl, indolyl, benzimidazolyl, benzo[b]thienyl, benzofuranyl, 1H-pyrrolo[2,3-b]pyridinyl, imidazo[1,2-a]pyridinyl, 1,3-dihydro-1-oxo-2H-isoindolyl, 1,3-dihydro-1,3-dioxo-2H-isoindolyl, or 2,3-dihydro-2-oxo-1H-benzimidazolyl, when present in the $Ar^1$ definition of any of the other embodiments, are attached to remainder of the molecule with their 5-membered ring.

In an embodiment, the present invention relates to those compounds of Formula (I) and pharmaceutically acceptable addition salts, and solvates thereof, or any subgroup thereof as mentioned in any of the other embodiments, wherein $Ar^1$ is phenyl, pyridinyl, indazolyl, indol-1-yl, indol-3-yl, thienyl, benzo[b]thienyl, 1H-pyrrolo[2,3-b]pyridinyl, imidazo[1,2-a]pyridinyl, 1,3-dihydro-1-oxo-2H-isoindolyl, or 1,3-dihydro-1,3-dioxo-2H-isoindolyl; each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ and $C_{1-4}$alkyl substituted with one or more halo atoms;
$R^5$ is —$OR^7$ or —O—$(CH_2)_m$—O—$R^7$;
$R^6$ is —$OR^8$ or —O—$(CH_2)_m$—O—$R^8$;
or $R^5$ and $R^6$ are taken together to form a bivalent radical —O—$CH_2$—O—.

In an embodiment, the present invention relates to those compounds of Formula (I) and pharmaceutically acceptable addition salts, and solvates thereof, or any subgroup thereof as mentioned in any of the other embodiments, wherein
$R^5$ is —$OR^7$ or —O—$(CH_2)_m$—O—$R^7$;
$R^6$ is —$OR^8$ or —O—$(CH_2)_m$—O—$R^8$;
or $R^5$ and $R^6$ are taken together to form a bivalent radical —O—$CH_2$—O—.

In an embodiment, the present invention relates to those compounds of Formula (I) and pharmaceutically acceptable addition salts, and solvates thereof, or any subgroup thereof as mentioned in any of the other embodiments, wherein
$R^5$ is —$OR^7$ or —O—$(CH_2)_m$—O—$R^7$;
$R^6$ is —$OR^8$ or —O—$(CH_2)_m$—O—$R^8$.

In an embodiment, the present invention relates to those compounds of Formula (I) and pharmaceutically acceptable addition salts, and solvates thereof, or any subgroup thereof as mentioned in any of the other embodiments, wherein n is 1.

In an embodiment, the present invention relates to those compounds of Formula (I) and pharmaceutically acceptable addition salts, and solvates thereof, or any subgroup thereof as mentioned in any of the other embodiments, wherein $R^4$ is hydrogen.

In an embodiment, the present invention relates to those compounds of Formula (I) and pharmaceutically acceptable addition salts, and solvates thereof, or any subgroup thereof as mentioned in any of the other embodiments, wherein R$^4$ is hydrogen or fluoro; in particular fluoro.

In an embodiment, the present invention relates to those compounds of Formula (I) and pharmaceutically acceptable addition salts, and solvates thereof, or any subgroup thereof as mentioned in any of the other embodiments, wherein A is CH.

In an embodiment, the present invention relates to those compounds of Formula (I) and pharmaceutically acceptable addition salts, and solvates thereof, or any subgroup thereof as mentioned in any of the other embodiments, wherein A is N.

In an embodiment, the present invention relates to those compounds of Formula (I) and pharmaceutically acceptable addition salts, and solvates thereof, or any subgroup thereof as mentioned in any of the other embodiments, wherein R$^2$ and R$^3$ are the same and are hydrogen.

In an embodiment, the present invention relates to those compounds of Formula (I) and pharmaceutically acceptable addition salts, and solvates thereof, or any subgroup thereof as mentioned in any of the other embodiments, wherein R$^2$ and R$^3$ are the same and are fluoro.

In an embodiment, the present invention relates to those compounds of Formula (I) and pharmaceutically acceptable addition salts, and solvates thereof, or any subgroup thereof as mentioned in any of the other embodiments, wherein R$^5$ and R$^6$ are methoxy.

In an embodiment, the present invention relates to those compounds of Formula (I) and pharmaceutically acceptable addition salts, and solvates thereof, or any subgroup thereof as mentioned in any of the other embodiments, wherein R$^5$ and R$^6$ are not taken together to form the bivalent radical —O—(CH$_2$)$_n$—O—.

In an embodiment, the present invention relates to those compounds of Formula (I) and pharmaceutically acceptable addition salts, and solvates thereof, or any subgroup thereof as mentioned in any of the other embodiments, wherein Ar$^1$ is phenyl, pyridinyl, indazolyl, pyrazolyl, indolyl, benzimidazolyl, thienyl, benzo[b]thienyl, benzofuranyl, 1H-pyrrolo[2,3-b]pyridinyl, imidazo[1,2-a]pyridinyl, 1,3-dihydro-1-oxo-2H-isoindolyl, 1,3-dihydro-1,3-dioxo-2H-isoindolyl or 2,3-dihydro-2-oxo-1H-benzimidazolyl;
each optionally substituted with 1, 2 or 3 substituents each independently selected from the group consisting of C$_{1-4}$alkyl, C$_{1-4}$alkylcarbonyl, C$_{1-4}$alkyloxy, halo, Ar$^2$ and C$_{1-4}$alkyl substituted with one or more halo atoms;
and wherein R$^5$ and R$^6$ are not taken together to form the bivalent radical —O—(CH$_2$)$_n$—O—.

In an embodiment, the present invention relates to those compounds of Formula (I) and pharmaceutically acceptable addition salts, and solvates thereof, or any subgroup thereof as mentioned in any of the other embodiments, wherein R$^5$ is OR$^7$ and R$^6$ is OR$^8$.

In an embodiment, the present invention relates to those compounds of Formula (I) and pharmaceutically acceptable addition salts, and solvates thereof, or any subgroup thereof as mentioned in any of the other embodiments, wherein
R$^5$ is OR$^7$; R$^6$ is OR$^8$;
R$^7$ is C$_{1-4}$alkyl, in particular methyl;
R$^8$ is C$_{1-4}$alkyl optionally substituted with one morpholinyl; in particular R$^8$ is methyl or

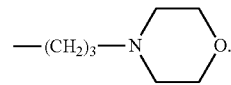

In an embodiment, the present invention relates to those compounds of Formula (I) and pharmaceutically acceptable addition salts, and solvates thereof, or any subgroup thereof as mentioned in any of the other embodiments, wherein
R$^5$ is hydrogen, —OR$^7$ or —O—(CH$_2$)$_m$—O—C$_{1-4}$alkyl;
R$^6$ is hydrogen, —OR$^8$ or —O—(CH$_2$)$_m$—O—C$_{1-4}$alkyl;
provided that at least one of R$^5$ and R$^6$ is not hydrogen.

In an embodiment, the present invention relates to those compounds of Formula (I) and pharmaceutically acceptable addition salts, and solvates thereof, or any subgroup thereof as mentioned in any of the other embodiments, wherein
R$^7$ is C$_{1-4}$alkyl, in particular methyl;
R$^8$ is C$_{1-4}$alkyl, in particular methyl.

In an embodiment, the present invention relates to those compounds of Formula (I) and pharmaceutically acceptable addition salts, and solvates thereof, or any subgroup thereof as mentioned in any of the other embodiments, wherein one or more of the following heterocyclic groups in the Ar$^1$ definition are:
pyridinyl is 2-pyridinyl;
indazolyl is indazol-1-yl or indazol-3-yl;
pyrazolyl is pyrazol-3-yl or pyrazol-5-yl;
indolyl is indol-1-yl, indol-2-yl or indol-3-yl;
imidazolyl is imidazol-1-yl;
benzimidazolyl is benzimidazol-1-yl;
thienyl is 2-thienyl or 3-thienyl;
benzo[b]thienyl is benzo[b]thien-3-yl;
benzofuranyl is 3-benzofuranyl;
1H-pyrrolo[2,3-b]pyridinyl is 1H-pyrrolo[2,3-b]pyridin-3-yl;
imidazo[1,2-a]pyridinyl is imidazo[1,2-a]pyridin-3-yl;
1,3-dihydro-1-oxo-2H-isoindolyl is 1,3-dihydro-1-oxo-2H-isoindol-2-yl;
1,3-dihydro-1,3-dioxo-2H-isoindolyl is 1,3-dihydro-1,3-dioxo-2H-isoindol-2-yl;
2,3-dihydro-2-oxo-1H-benzimidazolyl is 2,3-dihydro-2-oxo-1H-benzimidazol-1-yl;
it should be understood that any of these heterocyclic groups may be substituted as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein
Ar$^1$ is phenyl, 2-pyridinyl, indazol-1-yl, indazol-3-yl, pyrazol-3-yl, pyrazol-5-yl, indol-1-yl, indol-2-yl, indol-3-yl, imidazol-1-yl, benzimidazol-1-yl, 2-thienyl, 3-thienyl, benzo[b]thien-3-yl, 3-benzofuranyl, 1H-pyrrolo[2,3-b]pyridin-3-yl, imidazo[1,2-a]pyridin-3-yl, 1,3-dihydro-1-oxo-2H-isoindol-2-yl, 1,3-dihydro-1,3-dioxo-2H-isoindol-2-yl or 2,3-dihydro-2-oxo-1H-benzimidazol-1-yl;
it should be understood that any of these groups may be substituted as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein
Ar$^1$ is phenyl, 2-pyridinyl, indazol-1-yl, indazol-3-yl, pyrazol-3-yl, pyrazol-5-yl, indol-1-yl, indol-2-yl, indol-3-yl, benzimidazol-1-yl, 2-thienyl, 3-thienyl, benzo[b]thien-3-yl, 3-benzofuranyl, 1H-pyrrolo[2,3-b]pyridin-3-yl, imidazo[1, 2-a]pyridin-3-yl, 1,3-dihydro-1-oxo-2H-isoindol-2-yl, 1,3-dihydro-1,3-dioxo-2H-isoindol-2-yl or 2,3-dihydro-2-oxo-1H-benzimidazol-1-yl;

it should be understood that any of these groups may be substituted as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein
$Ar^1$ is phenyl, indol-1-yl or indol-3-yl; in particular indol-1-yl or indol-3-yl; more in particular indol-3-yl; it should be understood that any of these groups may be substituted as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein
$Ar^1$ is phenyl, indol-1-yl or indol-3-yl; in particular indol-1-yl or indol-3-yl; more in particular indol-3-yl;
each optionally substituted with 1 or 2 substituents selected from the group consisting of methyl and fluoro.

In an embodiment, the present invention relates to those compounds of Formula (I) and pharmaceutically acceptable addition salts, and solvates thereof, or any subgroup thereof as mentioned in any of the other embodiments, wherein
$Ar^1$ is phenyl, indazolyl, indolyl, benzimidazolyl, benzo[b]thienyl, benzofuranyl, 1H-pyrrolo[2,3-b]pyridinyl or imidazo[1,2-a]pyridinyl;
each optionally substituted with 1, 2 or 3 substituents each independently selected from the group consisting of $C_{1-4}$alkyl, $C_{1-4}$alkylcarbonyl, $C_{1-4}$alkyloxy, halo and $C_{1-4}$alkyl substituted with 1, 2 or 3 halo atoms.

In an embodiment, the present invention relates to those compounds of Formula (I) and pharmaceutically acceptable addition salts, and solvates thereof, or any subgroup thereof as mentioned in any of the other embodiments, wherein
$R^1$ is —$Ar^1$; $Ar^1$ is phenyl, indol-1-yl or indol-3-yl; in particular indol-1-yl or indol-3-yl; more in particular indol-3-yl;
each optionally substituted with 1 or 2 substituents selected from the group consisting of methyl and fluoro.

In an embodiment, the present invention relates to those compounds of Formula (I) and pharmaceutically acceptable addition salts, and solvates thereof, or any subgroup thereof as mentioned in any of the other embodiments, wherein
$R^1$ is —$Ar^1$;
$Ar^1$ is indol-1-yl or indol-3-yl, in particular indol-3-yl, each optionally substituted with 1 or 2 substituents selected from the group consisting of methyl, fluoro and methoxy, in particular each optionally substituted with 1 or 2 substituents selected from the group consisting of methyl and fluoro.

In an embodiment, the present invention relates to those compounds of Formula (I) and pharmaceutically acceptable addition salts, and solvates thereof, or any subgroup thereof as mentioned in any of the other embodiments, wherein
$R^1$ is —$Ar^1$; $Ar^1$ is indol-1-yl or indol-3-yl; in particular indol-3-yl;
each substituted with 1 or 2 substituents selected from the group consisting of methyl and fluoro.

In an embodiment, the present invention relates to those compounds of Formula (I) and pharmaceutically acceptable addition salts, and solvates thereof, or any subgroup thereof as mentioned in any of the other embodiments, wherein one or more of the following heterocyclic groups in the $Ar^2$ definition are:

thienyl is 2-thienyl or 3-thienyl;

furanyl is 3-furanyl;

isoxazolyl is 4-isoxazolyl;

pyrazolyl is pyrazol-4-yl;

it should be understood that any of these heterocyclic groups may be substituted as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein $Ar^2$ is phenyl, 2-thienyl, 3-thienyl, 3-furanyl, 4-isoxazolyl or pyrazol-4-yl;

it should be understood that any of these groups may be substituted as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein $Ar^2$ is phenyl, 2-thienyl, 3-thienyl, 3-furanyl, 4-isoxazolyl or pyrazol-4-yl;

each optionally substituted with 1 methyl group.

In an embodiment, the present invention relates to those compounds of Formula (I) and pharmaceutically acceptable addition salts, and solvates thereof, or any subgroup thereof as mentioned in any of the other embodiments, wherein $Ar^1$ is as defined in any of the other embodiments and is substituted with at least 1 and maximum 3 substituents as defined in any of the other embodiments.

Another embodiment of the present invention relates to those compounds of Formula (I) and pharmaceutically acceptable addition salts, and solvates thereof, or any subgroup thereof as mentioned in any of the other embodiments, wherein the expression "$C_{1-4}$alkyl substituted with one or more halo atoms" is in particular "$C_{1-4}$alkyl substituted with 1, 2 or 3 halo atoms"; more in particular "$C_{1-4}$alkyl substituted with 3 halo atoms"; even more in particular "$C_{1-4}$alkyl substituted with 3 fluoro atoms".

In an embodiment the compound of Formula (I) is selected from the group consisting of

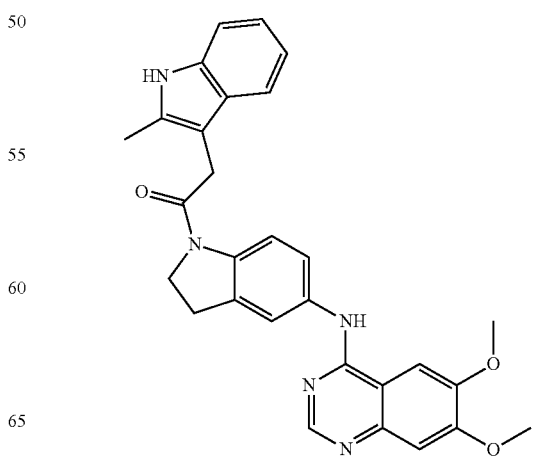

-continued

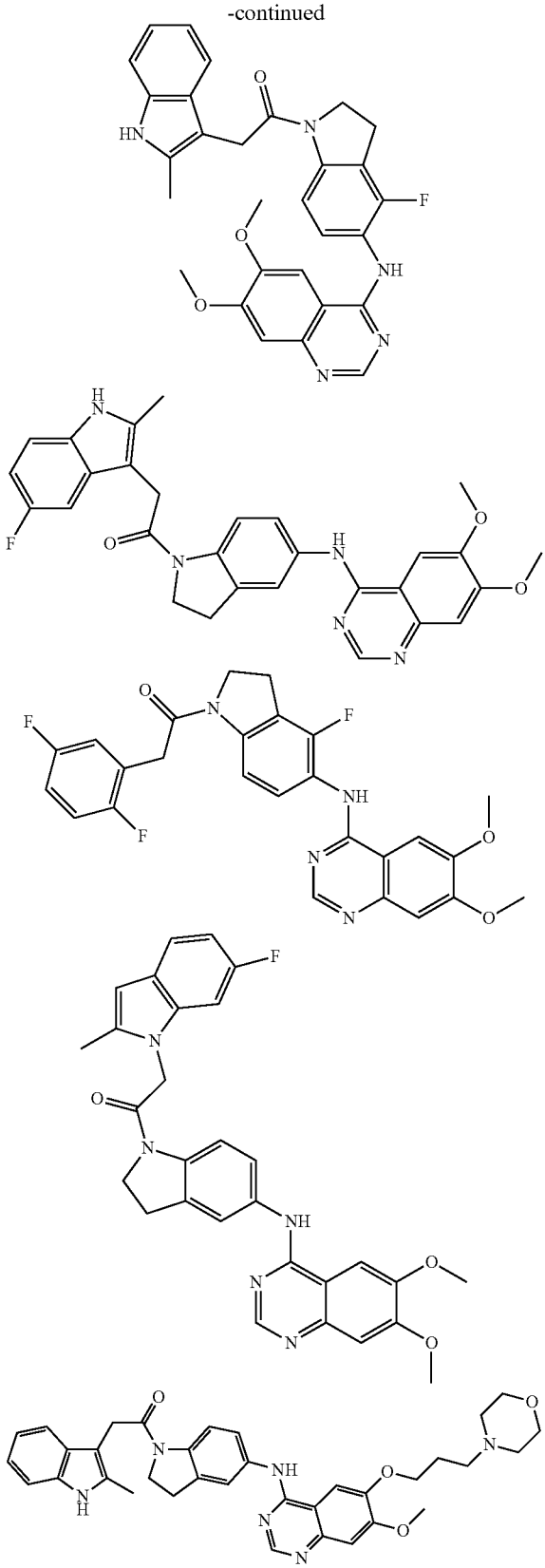

tautomers and stereoisomeric forms thereof,
and pharmaceutically acceptable addition salts, and solvates thereof.

All possible combinations of the above-indicated embodiments are considered to be embraced within the scope of this invention.

Preparation of the Compounds

Synthetic Methods

The present invention is also concerned with processes for preparing the compounds of this invention, intermediates and subgroups thereof.

The compounds of Formula (I) of the present invention can be prepared according to the procedures of the following schemes and examples, using appropriate materials which are either commercially available or can be prepared by standard means obvious to those skilled in the art, and are further exemplified by specific examples. Moreover, by utilizing the procedures described with the disclosure contained herein, one of ordinary skill in the art can readily prepare additional compounds of the present invention claimed herein.

The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The compounds of the present invention can also be prepared using standard synthetic processes commonly used by those skilled in the art of organic chemistry.

During any of the below synthetic sequences it may be necessary and/or desirable to protect sensitive or reactive functional groups (for example, hydroxy, amino, thio or carboxy) on any of the intermediates or molecules concerned, where these are desired in the final product, to avoid their unwanted participation in the reactions. Conventional protecting groups can be used therefor in accordance with standard practice. The protecting groups may be removed at a convenient subsequent stage using methods known from the art.

Alternatively, in the presence of reactive functional groups, the person skilled in the art may consider tuning the general reaction conditions on the basis of standard chemistry knowledge, to avoid undesired side reactions.

The skilled person will realize that in some reactions microwave heating may be used instead of conventional heating to shorten the overall reaction time.

The general preparation of some typical examples is shown below. All the variables are defined as described in the scope of the invention unless otherwise mentioned or unless a context dictates otherwise.

Scheme 1 (Method A)

Method A

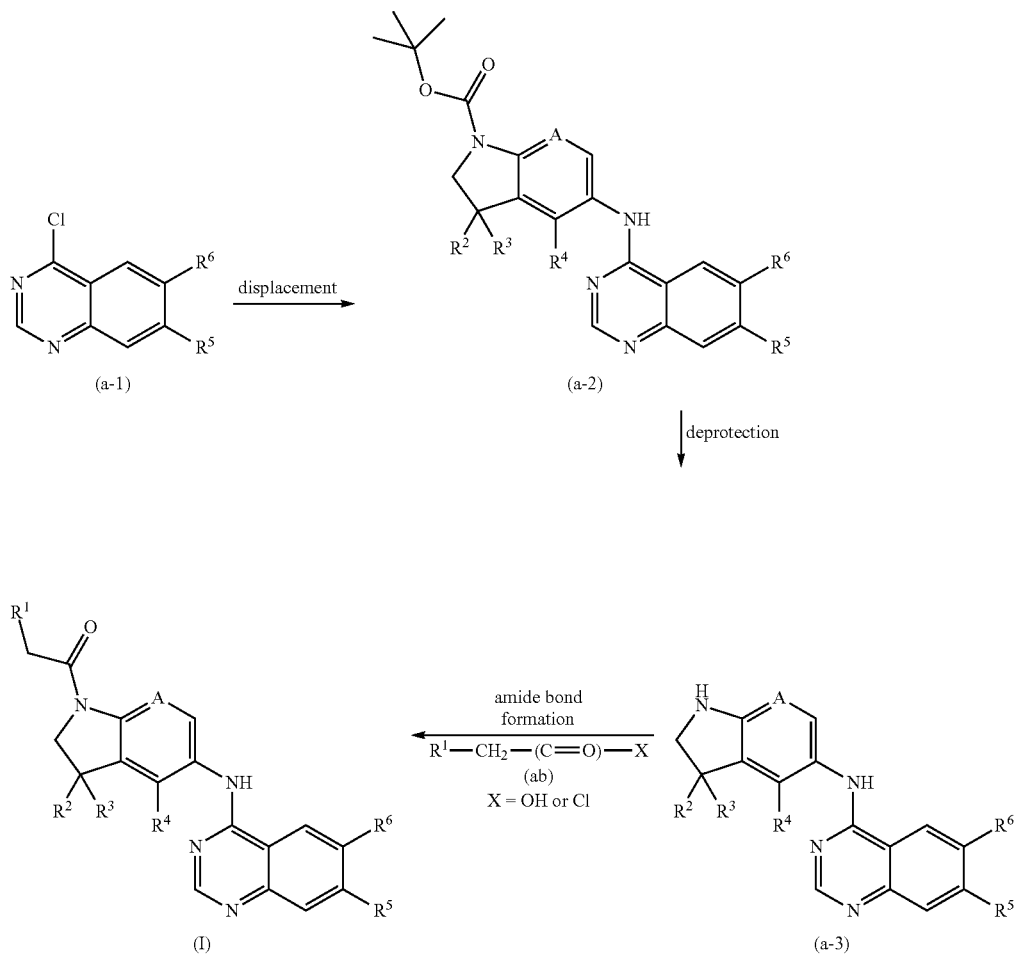

Under Method A, a compound of Formula (I) can be prepared via a nucleophilic aromatic substitution/deprotection/amide bond formation sequence to assemble the side chain on the quinazoline scaffold.

An intermediate of formula (a-2) can be prepared by reacting an appropriately functionalized and Boc-protected ('Boc' means tert-Butyloxycarbonyl) indolinyl or azaindolinyl moiety with a quinazoline derivative of formula (a-1) via displacement of the halogen (in particular a chlorine atom) from the 4-position of the quinazoline scaffold. The reaction may be performed by heating the 2 building blocks together in a suitable solvent (such as $^i$PrOH (2-propanol)) at between 75° C. and 115° C. for between 1 h and 12 h. Said indolinyl or azaindolinyl and quinazoline building blocks may be obtained either from commercial sources or can be easily prepared by the skilled person as described herein or by standard procedures of organic chemistry.

Alternatively, the nitrogen in an indolinyl or azaindolinyl of formula (a-2) can also be protected by a protecting group such as $C_{1-4}$alkylcarbonyl, e.g. methylcarbonyl, instead of a Boc-group.

An intermediate of formula (a-3) can be obtained by subsequent Boc-deprotection under acidic conditions (eg, TFA, HCl) in a suitable solvent (such as DCM; dioxane). A compound of Formula (I) can be prepared by an acylation reaction of the deprotected indoline or azaindoline of formula (a-3) in straightforward fashion with an intermediate of formula (ab) wherein X is OH or Cl (eg, via amide bond formation in the presence of a base (such as $^i$Pr$_2$NEt (diisopropylethylamine)) using standard coupling reagents such as HATU (1-[bis(dimethylamino)methylene]-1H-[1,2,3]triazolo[4,5-b]pyridin-1-ium 3-oxide hexafluorophosphate), TBTU (2-(1H-Benzotriazole-1-yl)-1,1,3,3-tetramethyluronium tetrafluoroborate) in a suitable solvent such as DMF (N,N-dimethylformamide) at temperatures between room temperature and 90° C.; or reaction with an acyl chloride). An intermediate of formula (ab) is commercially available or can be prepared by standard means obvious to those skilled in the art.

Scheme 2 (Method B)

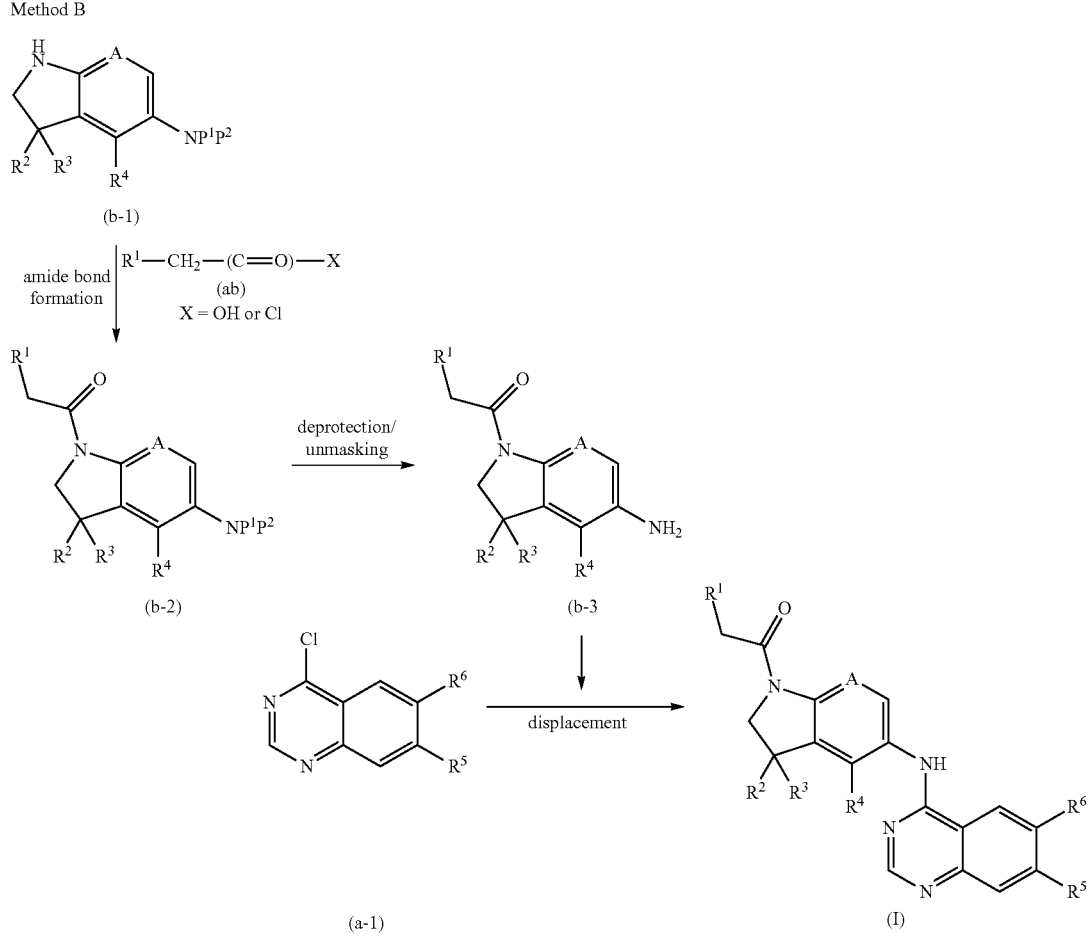

Under Method B, a compound of Formula (I) can be prepared by introducing a pre-assembled side chain (b-3) on the quinazoline scaffold of formula (a-1) as the final step.

An intermediate of formula (b-2) can be prepared by an acylation reaction of the appropriately functionalized amino-indolinyl or amino-azaindolinyl moiety of formula (b-1) (available either from commercial sources or prepared as described herein or by standard procedures of organic chemistry) in straightforward fashion with an intermediate of formula (ab) wherein X is OH or Cl (eg, via amide bond formation in the presence of a base (such as $^i$Pr$_2$NEt) using standard coupling reagents such as HATU, TBTU in a solvent such as DMF at temperatures between room temperature and 80° C.; or reaction with an acyl chloride). The intermediate of formula (b-1) has the amino functionality protected or masked as a pre-cursor moiety (such as nitro) (depicted as NP$^1$P$^2$).

An intermediate of formula (b-3) can be prepared by deprotection/unmasking of the aniline moiety of the intermediate (b-2) (eg, by reduction of a nitro moiety with Pd/C in a solvent such as MeOH or EtOH/THF under a hydrogen atmosphere).

A compound of Formula (I) can be prepared by reacting an intermediate of formula (b-3) with a quinazoline derivative of formula (a-1) via displacement of a halogen (more specifically a chlorine atom) from the 4-position of the quinazoline derivative. The reaction may be performed by heating the 2 building blocks together in a suitable solvent (such as $^i$PrOH) at between 75° C. and 115° C. for between 1 h and 12 h. An intermediate of formula (a-1) is either from commercial sources or can be easily prepared by the skilled person as described herein or by standard procedures of organic chemistry.

Scheme 3 (Method C)

Method C

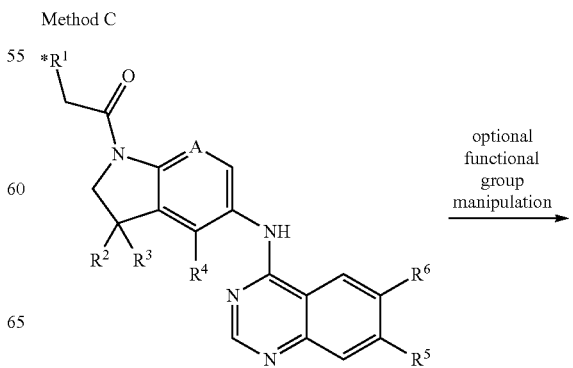

optional functional group manipulation

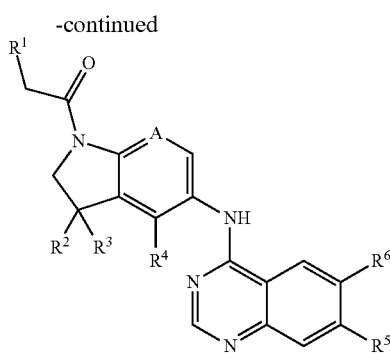

Compounds of Formula (I) and any subgroup thereof may be converted into further compounds of Formula (I) and any subgroup thereof, using procedures known in the art.

Under Method C, the molecule can be assembled (using either Method A or B) with a suitably functionalized $R^1$ moiety ($*R^1$) such that subsequent modification is possible (eg, via Suzuki cross-coupling to an aryl halide, such as an aryl bromide, performed at between 110° C. and 125° C. in a microwave oven for 5 minutes; reductive elimination) to yield a further compound of Formula (I).

Chemica 2010, 2, 378; Bioorganic & Medicinal Chemistry Letters 2007, 17, 5630; Tetrahedron 1999, 55, 1881; Organic Letters 2003, 5, 4943; Green Chemistry 2012, 14, 58; Journal of Organic Chemistry 2007, 72, 9364), where U is C—R and R can be H or an alkyl chain comprising either one or both carbon atoms of the nascent indoline/azaindoline ring. Alternatively, (d-4) can be accessed from (d-5) by deprotection. In turn, (d-5) can be prepared by nitration of (d-3) (eg, WO 2009/130481) or via reduction of a suitable scaffold (d-2) (eg, Synthesis, 2007, 10, 1509; WO 2012/069917; Synthesis 2005, 15, 2503; Bioorganic & Medicinal Chemistry Letters 2002, 12, 3105) with protection prior to the reduction. Said indole/azaindole scaffolds (d-2) can be obtained commercially or can be prepared by those skilled in the art by standard procedures of organic chemistry starting from an intermediate of formula (d-1) (eg, Chem. Sci. 2013, 4, 29; Organic Letters 2009, 11, 1357; Journal of Organic Chemistry 2010, 75, 11), where U is C—R and R can be H or an alkyl chain comprising either one or both carbon atoms of the nascent indole/azaindole ring. Furthermore, $*R^4$ can be converted to $R^4$ on a suitable indole/azaindole scaffold (d-2) by standard procedures accessible to those skilled in the art (eg, Heterocycles 1986, 24, 1667; WO 2004/009601; Organic Letters 2003, 5, 5023). Similarly, (d-6) can be obtained from (d-5) by deprotection/unmasking Scheme 4 (Method D)

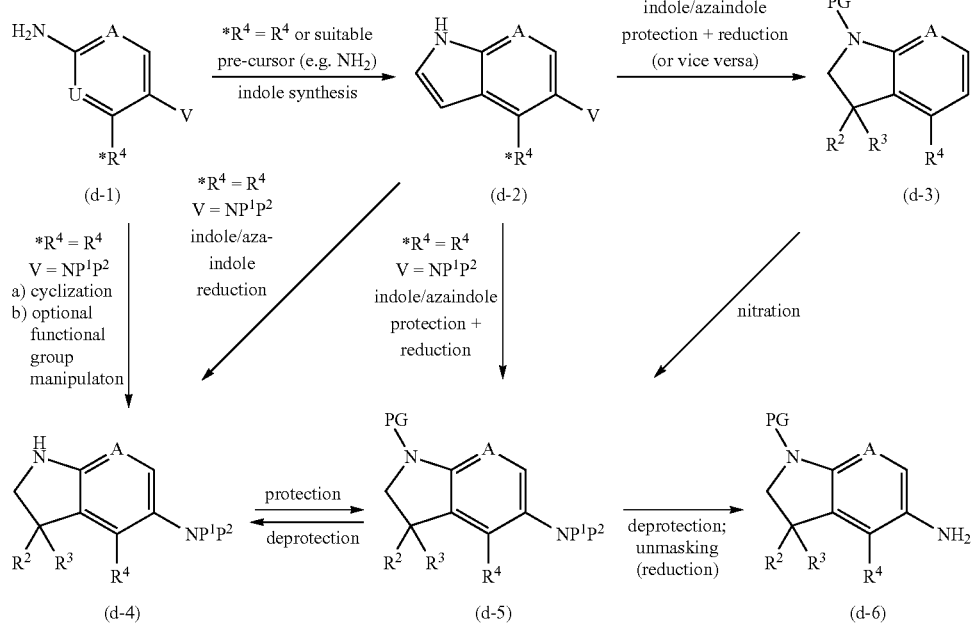

$NP^1P^2$ is an amino functionality protected or masked as a pre-cursor moiety (such as nitro)

Under Method D, non-commercial indoline or azaindoline intermediates/starting materials (for Methods A, B, C described herein) of general formulae (d-4) or (d-6) can be prepared via multiple (non-limiting) synthetic approaches, as illustrated in Scheme 4 (PG means protecting group such as Boc or methylcarbonyl). Thus, (d-4) can be prepared from the appropriate aniline (d-1) via cyclization and eventual subsequent functional group manipulation (eg, Der Pharma Chemica 2010, 2, 378; ... ) of the aniline moiety. Additionally, (d-5) can be prepared from (d-4) via a protection step, and (d-4) accessed directly from (d-2) via reduction.

Starting materials can be obtained commercially or can be prepared by those skilled in the art by standard procedures of organic chemistry. The preparation of such starting materials is described within the accompanying non-limiting examples. Alternatively, necessary starting materials are obtainable by analogous procedures to those illustrated or cited, which are within the ordinary skill of an organic chemist.

For example, a quinazoline (or quinazolone pre-cursor) may be prepared by any process known to be applicable to the preparation of chemically-related compounds (eg, WO 2003/051849; WO 2003/064399; *Synthetic Communications* 2012, 42, 341; *J. Medicinal Chemistry* 1989, 32, 847; *Tetrahedron* 2005, 61, 10153; *Tetrahedron Letters* 1980, 21, 3029; *J. Heterocyclic Chemistry* 2006, 43, 913). Traditional methods for preparation of 4-anilinoquinazolines include the construction of a suitable 4-chloroquinazoline intermediate and then reacting said intermediate with suitable substituted aniline in acidic or basic media (eg, EP 0566226 (1993); U.S. Pat. No. 5,747,498 (1998)). Alternatively quinazoline assembly may be via construction of a suitable formamidine intermediate (eg, *Org. Proc. Res. Dev.* 2007, 11, 813).

In all these preparations, the reaction products may be isolated from the reaction medium and, if necessary, further purified according to methodologies generally known in the art such as, for example, extraction, crystallization, trituration and chromatography.

Pharmacology

It has been found that the compounds of the present invention inhibit PERK kinase activity.

Therefore, the compounds of the invention and compositions thereof may be useful for use in the treatment or prevention, in particular in the treatment, of cancer, in particular secretory cancer types, diabetes (e.g. type 1 diabetes), obesity, ocular diseases, stroke, myocardial infarction, cardiovascular disease, atherosclerosis, arrhythmias, viral infectious and inflammatory diseases, and neurodegenerative diseases (such as amyotrophic lateral sclerosis, prion-related diseases, Huntington's, Alzheimer's and Parkinson's disease), and the like;
in particular for use in the treatment or prevention, in particular in the treatment, of cancer, in particular secretory cancer types, diabetes, obesity, viral infectious and inflammatory diseases, and neurodegenerative diseases (such as amyotrophic lateral sclerosis, prion-related diseases, Huntington's, Alzheimer's and Parkinson's disease), and the like;
more in particular for use in the treatment or prevention, in particular in the treatment, of cancer;
even more in particular for use in the treatment or prevention, in particular in the treatment, of secretory cancer types.

Therefore, the compounds of the invention and compositions thereof may be useful for use in the treatment or prevention, in particular in the treatment, of cancer, in particular secretory cancer types.

In an embodiment, the compounds of the invention and compositions thereof may be useful for use in the treatment or prevention, in particular in the treatment, of multiple myeloma, waldenstrom's macroglobulinemia, B-cell lymphoma (e.g. diffuse large B-cell lymphoma, chronic lymphocytic leukemia, mantle cell lymphoma, follicular lymphoma, hairy cell leukemia), insulinoma;
in particular multiple myeloma, waldenstrom's macroglobulinemia, diffuse large B-cell lymphoma, mantle cell lymphoma, follicular lymphoma, insulinoma.

In an embodiment, the compounds of the invention and compositions thereof may be useful for use in the treatment or prevention, in particular in the treatment, of multiple myeloma, B-cell lymphoma (e.g. diffuse large B-cell lymphoma, chronic lymphocytic leukemia, mantle cell lymphoma, follicular lymphoma, hairy cell leukemia), insulinoma; in particular multiple myeloma, diffuse large B-cell lymphoma, mantle cell lymphoma, follicular lymphoma, insulinoma.

The invention relates to compounds of Formula (I) and pharmaceutically acceptable addition salts, and solvates thereof, for use as a medicament.

The invention also relates to compounds of Formula (I) and pharmaceutically acceptable addition salts, and solvates thereof, for use in the inhibition of PERK kinase activity.

The compounds of the present invention may have anti-angiogenic activity.

The invention also relates to compounds of Formula (I) and pharmaceutically acceptable addition salts, and solvates thereof, for use in anti-angiogenic therapies.

The invention also relates to compounds of Formula (I) and pharmaceutically acceptable addition salt, and solvates thereof, for use in the treatment or prevention, in particular in the treatment, of secretory cancer types.

The invention also relates to compounds of Formula (I) and pharmaceutically acceptable addition salts, and solvates thereof, for use in the treatment or prevention, in particular in the treatment, of multiple myeloma, waldenstrom's macroglobulinemia, B-cell lymphoma (e.g. diffuse large B-cell lymphoma, chronic lymphocytic leukemia, mantle cell lymphoma, follicular lymphoma, hairy cell leukemia), insulinoma; in particular multiple myeloma, waldenstrom's macroglobulinemia, diffuse large B-cell lymphoma, mantle cell lymphoma, follicular lymphoma, insulinoma.

The invention also relates to compounds of Formula (I) and pharmaceutically acceptable addition salts, and solvates thereof, for use in the treatment or prevention, in particular in the treatment, of diseases or conditions selected from the group consisting of cancer, in particular secretory cancer types, diabetes (e.g. type 1 diabetes), obesity, ocular diseases, stroke, myocardial infarction, cardiovascular disease, atherosclerosis, arrhythmias, viral infectious and inflammatory diseases, and neurodegenerative diseases (such as amyotrophic lateral sclerosis, prion-related diseases, Huntington's, Alzheimer's and Parkinson's disease), and the like.

The invention also relates to compounds of Formula (I) and pharmaceutically acceptable addition salts, and solvates thereof, for use in the treatment or prevention, in particular in the treatment, of diseases or conditions selected from the group consisting of neurodegenerative diseases such as amyotrophic lateral sclerosis, prion-related diseases, Huntington's, Alzheimer's, Parkinson's disease, diffuse Lewy body dementia, frontotemporal dementia, dementias with mixed protein pathologies (e.g. tau, amyloid and alphasynuclein) and the like.

The invention also relates to compounds of Formula (I) and pharmaceutically acceptable addition salts, and solvates thereof, for use in the treatment or prevention, in particular in the treatment, of diseases or conditions selected from the group consisting of neurodegenerative diseases such as amyotrophic lateral sclerosis, prion-related diseases, Huntington's, Alzheimer's dementia (Alzheimer's disease, senile dementia of Alzheimer type), Down's disease, disturbance of memory, mild cognitive impairment (MCI), Dutch-type hereditary cerebral hemorrhage with amyloidosis, cerebral amyloid angiopathy, other degenerated dementia, vascular degenerated mixed dementia, dementia associated with Parkinson's disease, dementia associated with progressive supranuclear paralysis, dementia associated with corticobasal degeneration, age-related macular degeneration, amyloid angiopathy, Parkinson's disease, diffuse Lewy body dementia, frontotemporal dementia, dementias with mixed protein pathologies (e.g. tau, amyloid and alphasynuclein), argyrophilic grain dementia, creutzfeldt-Jakob disease, dementia pugilistica, diffuse neurofibrillary tangles with calcificationa, Gerstmann-Straussler-Scheinker disease, Hallervorden-Spatz disease, myotonic dystrophy, Niemann-Pick disease (type C), non-Guamanian motor neuron disease with neurofibrillary tangles, Pick's disease, postencephalitic parkinsonism, progressive subcortical gliosis, progressive supranuclear palsy, subacute sclerosing panencephalitis, tangle only dementia, cognitive disorder, hypoxia, brain ischemia (cerebral ischemia), surgical dementia, glioblastoma or glioblastoma multiforme (GBM), traumatic brain injury (TBI), chronic encephalopathy, brain trauma, dementia pugilistica, or chemo-brain (CB) and the like.

In an embodiment, said disease or condition is cancer, in particular secretory cancer types.

In an embodiment, said disease or condition is multiple myeloma, waldenstrom's macroglobulinemia, B-cell lymphoma (e.g. diffuse large B-cell lymphoma, chronic lymphocytic leukemia, mantle cell lymphoma, follicular lymphoma, hairy cell leukemia), insulinoma; in particular multiple myeloma, waldenstrom's macroglobulinemia, diffuse large B-cell lymphoma, mantle cell lymphoma, follicular lymphoma, insulinoma.

In an embodiment, said disease or condition is haematological cancer.

In an embodiment, said disease or condition is multiple myeloma, waldenstrom's macroglobulinemia or B-cell lymphoma (e.g. diffuse large B-cell lymphoma, chronic lymphocytic leukemia, mantle cell lymphoma, follicular lymphoma, hairy cell leukemia); in particular multiple myeloma or B-cell lymphoma (e.g. diffuse large B-cell lymphoma, chronic lymphocytic leukemia, mantle cell lymphoma, follicular lymphoma, hairy cell leukemia).

In an embodiment, said disease or condition is multiple myeloma or B-cell lymphoma (e.g. diffuse large B-cell lymphoma, chronic lymphocytic leukemia, mantle cell lymphoma, follicular lymphoma, hairy cell leukemia).

In an embodiment, said disease or condition is insulinoma.

In an embodiment, said disease or condition is multiple myeloma.

In an embodiment, said disease or condition is waldenstrom's macroglobulinemia.

In an embodiment, said disease or condition is B-cell lymphoma (e.g. diffuse large B-cell lymphoma, chronic lymphocytic leukemia, mantle cell lymphoma, follicular lymphoma, hairy cell leukemia).

In an embodiment, said disease or condition is secretary B-cell lymphoma.

In an embodiment, said disease or condition is diffuse large B-cell lymphoma, chronic lymphocytic leukemia, mantle cell lymphoma, follicular lymphoma, hairy cell leukemia.

In an embodiment, said disease or condition is diffuse large B-cell lymphoma, mantle cell lymphoma, follicular lymphoma.

In an embodiment, said disease or condition is diffuse large B-cell lymphoma.

The compounds of the present invention can be "anti-cancer agents", which term also encompasses "anti-tumor cell growth agents" and "anti-neoplastic agents". For example, the methods of the invention may be useful for treating cancers and chemosensitizing and/or radiosensitizing tumor cells in cancers such as ACTH-producing tumors, acute lymphocytic leukemia, acute nonlymphocytic leukemia, cancer of the adrenal cortex, bladder cancer, colon cancer, brain cancer, breast cancer, cervical cancer, chronic myelocytic leukemia, colorectal cancer, cutaneous T-cell lymphoma, endometrial cancer, esophageal cancer, Ewing's sarcoma gallbladder cancer, head & neck cancer, Hodgkin's Lymphoma, Kaposi's sarcoma, kidney cancer, liver cancer, lung cancer (small and/or non-small cell), malignant peritoneal effusion, malignant pleural effusion, melanoma, mesothelioma, multiple myeloma, waldenstrom's macroglobulinemia, B-cell lymphoma (e.g. diffuse large B-cell lymphoma, chronic lymphocytic leukemia, mantle cell lymphoma, follicular lymphoma, hairy cell leukemia), insulinoma, neuroblastoma, osteosarcoma, ovarian cancer, ovary (germ cell) cancer, prostate cancer, pancreatic cancer, penile cancer, retinoblastoma, skin cancer, soft tissue sarcoma, squamous cell carcinomas, stomach cancer, testicular cancer, thyroid cancer, trophoblastic neoplasms, uterine cancer, vaginal cancer, cancer of the vulva and Wilm's tumor.

Secretory cancer types are cancers characterized by a high rate of protein secretion (such as immunoglobulins or hormones); these cancer cells are characterized by an extensively developed endoplasmic reticulum.

The invention also relates to compounds of Formula (I) and pharmaceutically acceptable addition salts, and solvates thereof, for use in the treatment of said diseases.

The invention also relates to compounds of Formula (I) and pharmaceutically acceptable addition salts, and solvates thereof, for the treatment or prevention, in particular for the treatment, of said diseases.

The invention also relates to compounds of Formula (I) and pharmaceutically acceptable addition salts, and solvates thereof, for the treatment or prevention, in particular in the treatment, of PERK mediated diseases or conditions.

The invention also relates to the use of compounds of Formula (I) and pharmaceutically acceptable addition salts, and solvates thereof, for the manufacture of a medicament.

The invention also relates to the use of compounds of Formula (I) and pharmaceutically acceptable addition salts, and solvates thereof, for the manufacture of a medicament for the inhibition of PERK.

The invention also relates to the use of compounds of Formula (I) and pharmaceutically acceptable addition salts, and solvates thereof, for the manufacture of a medicament for the treatment or prevention, in particular for the treatment, of any one of the disease conditions mentioned hereinbefore.

The invention also relates to the use of compounds of Formula (I) and pharmaceutically acceptable addition salts, and solvates thereof, for the manufacture of a medicament for the treatment of any one of the disease conditions mentioned hereinbefore.

The compounds of Formula (I) and pharmaceutically acceptable addition salts, and solvates thereof, can be administered to mammals, preferably humans for the treatment or prevention of any one of the diseases mentioned hereinbefore.

In view of the utility of the compounds of Formula (I) and pharmaceutically acceptable addition salts, and solvates thereof there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I) and pharmaceutically acceptable addition salts, and solvates thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent cancer or cancer-related conditions, may be administered alone or in combination with one or more additional therapeutic agents. Combination therapy includes administration of a single pharmaceutical dosage formulation which contains a compound of Formula (I), a pharmaceutically acceptable addition salt, or a solvate thereof, and one or more additional therapeutic agents, as well as administration of the compound of Formula (I), a pharmaceutically acceptable addition salt, or a solvate thereof, and each additional therapeutic agents in its own separate pharmaceutical dosage formulation. For example, a compound of Formula (I), a pharmaceutically acceptable addition salt, or a solvate thereof and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound of Formula (I), a pharmaceutically acceptable addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds of Formula (I) and pharmaceutically acceptable addition salts, and solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing a compound of Formula (I), a pharmaceutically acceptable addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the compounds of Formula (I) and pharmaceutically acceptable addition salts, and solvates thereof, in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), a pharmaceutically acceptable addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy, including chemotherapy and radiation treatment. Examples of anti-cancer agents or adjuvants (supporting agents in the therapy) include but are not limited to:

- platinum coordination compounds for example cisplatin optionally combined with amifostine, carboplatin or oxaliplatin;
- taxane compounds for example paclitaxel, paclitaxel protein bound particles (Abraxane™) or docetaxel;
- topoisomerase I inhibitors such as camptothecin compounds for example irinotecan, SN-38, topotecan, topotecan hcl;
- topoisomerase II inhibitors such as anti-tumour epipodophyllotoxins or podophyllotoxin derivatives for example etoposide, etoposide phosphate or teniposide;
- anti-tumour vinca alkaloids for example vinblastine, vincristine or vinorelbine;
- anti-tumour nucleoside derivatives for example 5-fluorouracil, leucovorin, gemcitabine, gemcitabine hcl, capecitabine, cladribine, fludarabine, nelarabine;
- alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;
- anti-tumour anthracycline derivatives for example daunorubicin, doxorubicin optionally in combination with dexrazoxane, doxil, idarubicin, mitoxantrone, epirubicin, epirubicin hcl, valrubicin;
- molecules that target the IGF-1 receptor for example picropodophilin;
- tetracarcin derivatives for example tetrocarcin A;
- glucocorticoïden for example prednisone;
- antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
- estrogen receptor antagonists or selective estrogen receptor modulators or inhibitors of estrogen synthesis for example tamoxifen, fulvestrant, toremifene, droloxifene, faslodex, raloxifene or letrozole;
- aromatase inhibitors such as exemestane, anastrozole, letrazole, testolactone and vorozole;
- differentiating agents such as retinoids, vitamin D or retinoic acid and retinoic acid metabolism blocking agents (RAMBA) for example accutane;
- DNA methyl transferase inhibitors for example azacytidine or decitabine;
- antifolates for example premetrexed disodium;
- antibiotics for example antinomycin D, bleomycin, mitomycin C, dactinomycin, carminomycin, daunomycin, levamisole, plicamycin, mithramycin;
- antimetabolites for example clofarabine, aminopterin, cytosine arabinoside or methotrexate, azacitidine, cytarabine, floxuridine, pentostatin, thioguanine;
- apoptosis inducing agents and antiangiogenic agents such as Bcl-2 inhibitors for example YC 137, BH 312, ABT 737, gossypol, HA 14-1, TW 37 or decanoic acid;
- tubuline-binding agents for example combrestatin, colchicines or nocodazole;
- kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus; or a Bruton's tyrosine kinase (BTK) inhibitor, for example ibrutinib;
- farnesyltransferase inhibitors for example tipifarnib;
- histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;
- Inhibitors of the ubiquitin-proteasome pathway for example carfilzomib, PS-341, MLN 0.41 or bortezomib;
- Yondelis;
- Telomerase inhibitors for example telomestatin;
- Matrix metalloproteinase inhibitors for example batimastat, marimastat, prinostat or metastat.
- Recombinant interleukins for example aldesleukin, denileukin diftitox,
- interferon alfa 2a, interferon alfa 2b, peginterferon alfa 2b
- MAPK inhibitors
- Retinoids for example alitretinoin, bexarotene, tretinoin
- Arsenic trioxide
- Asparaginase
- Steroids for example dromostanolone propionate, megestrol acetate, nandrolone (decanoate, phenpropionate), dexamethasone
- Gonadotropin releasing hormone agonists or antagonists for example abarelix, goserelin acetate, histrelin acetate, leuprolide acetate
- Thalidomide, lenalidomide
- Mercaptopurine, mitotane, pamidronate, pegademase, pegaspargase, rasburicase
- BH3 mimetics for example ABT-737
- MEK inhibitors for example PD98059, AZD6244, CI-1040
- colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.
- a steroidal cytochrome P450 17alpha-hydroxylase-17,20-lyase inhibitor (CYP17), e.g. abiraterone, abiraterone acetate.

The present invention further relates to a product containing as first active ingredient a compound according to the invention and as further active ingredient one or more anticancer agents, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter ($mg/m^2$) of body surface area, or as known in the art, if different. Trastuzumab is advantageously administered in a dosage of 1 to 5 mg per square meter ($mg/m^2$) of body surface area, particularly 2 to 4 $mg/m^2$ per course of treatment.

These dosages may be administered for example once, twice or more per course of treatment, which may be repeated for example every 7, 14, 21 or 28 days.

The following examples illustrate the present invention.

EXAMPLES

All solvents were obtained from commercial sources (Fluka, puriss.) and were used without further purification. With the exception of routine deprotection and coupling steps, reactions were carried out under an atmosphere of nitrogen in oven dried (110° C.) glassware. Organic extracts were dried over magnesium sulfate and were concentrated (after filtration of the drying agent) on rotary evaporators operating under reduced pressure. Flash chromatography was carried out on commercial flash chromatography systems (PurifFlash 215 from Interchim; Armen Spot; Knauer; Novasep operating at flow rates between 18 mL/min to 200 mL/min depending on the system employed) utilizing pre-packed columns.

Reagents were usually obtained directly from commercial suppliers (and used as supplied) but a limited number of compounds from in-house corporate collections were utilized. In the latter case, the reagents are readily accessible using routine synthetic steps well known to those skilled in the art.

$^1$H NMR spectra were recorded on a Bruker Avance 500 spectrometer equipped with a reverse triple-resonance ($^1$H, $^{13}$C, $^{15}$N TXI) probe with z gradients and operating at (reported) frequencies between 125 and 500 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; br, broad, and combinations thereof); coupling constant(s) in hertz (Hz); number of protons. Preparative scale HPLC separations were carried out on a Waters separation module, equipped with a Diode array detector and a simple quadripole MS detector using flow rates between from 20 to 50 ml/min.

The following abbreviations are used in the examples, the schemes and tables: Ac: acetyl; ACN: acetonitrile; aq.: aqueous; Ar: aryl; atm: atmosphere; cat.: catalytic; Co.: compound; dioxin(e): 1,4-dioxane; Celite®: diatomaceous earth; dppf: (1,1'-bisdiphenylphosphino)ferrocene; DAST: diethylaminosulfur trifluoride; 1,2-DCE: 1,2-dichloroethane; DCM: dichloromethane; DIAD: diisopropylazodicarboxylate; DIPE: diisopropyl ether; DIPEA: diisopropylethyl amine; DMA: N,N-dimethylacetamide; DMAP: N,N-dimethylpyridin-4-amine; DME: dimethoxyethane; DMF: dimethylformamide; DMS: dimethylsulfide; DMSO: dimethylsulfoxide; DMP: Dess-Martin Periodinane; EDC: 1-ethyl-(3-dimethylaminopropyl)carbodiimide HCl salt; eq.: equivalent(s); Et$_3$N:triethylamine; EtOAc: ethyl acetate; Et$_2$O: diethyl ether; EtOH: ethanol; FC: Flash chromatography; h: hour(s); HATU: O-(7-azabenzotriazol-1-yl)-N,N,N',N'-tetramethyluronium hexafluorophosphate; HOBt: 1-hydroxybenzotriazole; Int.: Intermediate; $^i$PrOH: 2-propanol; LC: liquid chromatography; MeCN: acetonitrile; min: minute(s); MeOH: methanol; M.pt: melting point; Ms: methanesulfonyl; MS: mass spectrum; NBS: N-bromo succinimide; quant.: quantitative; RP-HPLC: reversed phase high pressure liquid chromatography; RT: room temperature; sat.: saturated; sec.: second(s); SFC: Super-critical fluid chromatography; TBAF: tetrabutyl ammonium fluoride; TBTU: O-benzotriazol-1-yl-N,N,N',N'-tetramethyluronium tetrafluoroborate; TFA: trifluoroacetic acid; THF: tetrahydrofuran; THP: tetrahydropyranyl; TMS: trimethylsilyl; Ts: para-toluene sulfonyl.

Preparation of Intermediates

Intermediate 1

N-indolin-5-yl-6,7-dimethoxy-quinazolin-4-amine (hydrochloride salt)

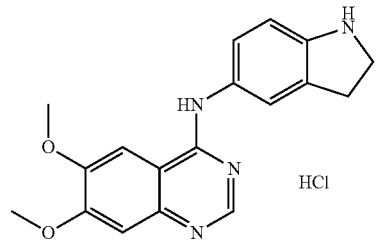 [SMILES: COc1cc2ncnc(Nc3ccc4c(c3)CCN4)c2cc1OC ; Cl]

Step 1 tert-butyl 5-[(6,7-dimethoxyquinazolin-4-yl)amino]indoline-1-carboxylate

A mixture of tert-butyl 5-amino-1-indoline-1-carboxylate (purchased from Enamine company) (5 g; 21.3 mmol), 4-chloro-6,7-dimethoxy-quinazoline (purchased from Activate Scientific Company) (5.6 g; 24.9 mmol) in $^i$PrOH (50 mL) was stirred at reflux for 2 h then at room temperature for 48 h. The precipitate was filtered off, washed twice with $^i$PrOH and four times with diethylether.

The precipitate was dried in vacuo to give tert-butyl 5-[(6,7-dimethoxyquinazolin-4-yl)amino]indoline-1-carboxylate (9.95 g; 100%). $^1$H NMR (500 MHz, DMSO-d$_6$, 296 K) δ 11.15 (br.s, 1H), 8.78 (s, 1H), 8.21 (s, 1H), 7.76 (br.s, 1H), 7.51 (s, 1H), 7.37-7.43 (m, 1H), 7.30 (s, 1H), 3.94-4.03 (m, 8H), 3.12 (t, J=8.5 Hz, 2H).

Step 2

N-indolin-5-yl-6,7-dimethoxy-quinazolin-4-amine (hydrochloride salt)

At 0° C. tert-butyl 5-[(6,7-dimethoxyquinazolin-4-yl)amino]indoline-1-carboxylate (3.40 g; 8.05 mmol) was added to 4 N HCl in dioxane (35 mL; 140 mmol). The reaction mixture was stirred at room temperature overnight. The precipitate was filtered off, washed with diethylether once and dried in vacuo to give intermediate 1 (N-indolin-5-yl-6,7-dimethoxy-quinazolin-4-amine) as its hydrochloride salt (2.77 g; 96%). $^1$H NMR (500 MHz, DMSO-d$_6$, 297 K) δ 11.73 (s, 1H), 8.82 (s, 1H), 8.45 (s, 1H), 7.75 (s, 1H), 7.63 (d, J=8.5 Hz, 1H), 7.43 (d, J=8.5 Hz, 1H), 7.39 (s, 1H), 4.03 (s, 3H), 4.00 (s, 3H), 3.75 (t, J=7.9 Hz, 3H), 3.23 (t, J=7.9 Hz, 2H).

Intermediates 2-5 were prepared by an analogous protocol as was used for the synthesis for Intermediate 1 using the appropriate 4-chloroquinazoline and aminoindoline starting materials (Table 1)

TABLE 1

| Int. | Structure | Starting Materials |
|---|---|---|
| 2 | (structure) · HCl | (structures) |
| 3 | (structure) · HCl | (structures) |
| 4 | (structure) · HCl | (structures) |

TABLE 1-continued

| Int. | Structure | Starting Materials |
|---|---|---|
| 5 | 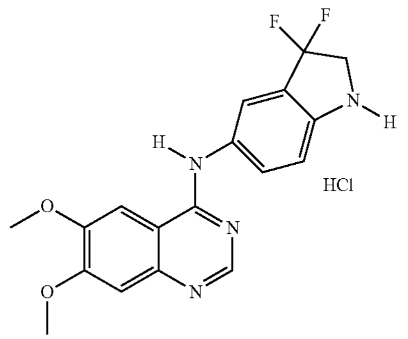 [SMILES: COc1cc2ncnc(Nc3ccc4c(c3)C(F)(F)CN4)c2cc1OC ; Cl] | |

[Structures shown in table]

Intermediate 6

N-(4-fluoroindolin-5-yl)-6,7-dimethoxy-quinazolin-4-amine (hydrochloride salt)

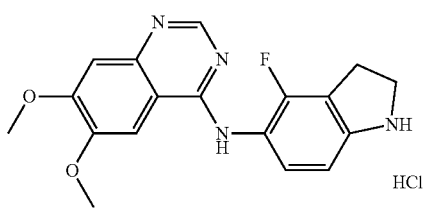 [SMILES: COc1cc2ncnc(Nc3ccc4c(c3F)CCN4)c2cc1OC ; Cl]

Step 1

1-[5-(6,7-dimethoxy-quinazolin-4-ylamino)-4-fluoro-2,3-dihydro-indol-1-yl]-ethanone

A mixture of 1-(4-fluoro-5-nitro-2,3-dihydro-indol-1-yl)-ethanone (prepared as described in International Patent Application WO 2009/130481) (600 mg; 2.7 mmol) was hydrogenated in a pressure vessel reactor at room temperature in EtOH (30 mL) and THF (20 mL) with 10% Pd/C (275 mg) as a catalyst at 3 bars of pressure of hydrogen for 3 h. The catalyst was filtered off on a pad of Celite®. The Celite® was washed with DCM and MeOH. The solvent was removed in vacuo to give 470 mg (90%) of crude 1-(5-amino-4-fluoro-indolin-1-yl)ethanone which was used without any purification in the next step.

A mixture of 1-(5-amino-4-fluoro-indolin-1-yl)ethanone (0.47 g; 2.42 mmol) and 4-chloro-6,7-dimethoxy-quinazoline (0.3 g; 1.34 mmol) in $^i$PrOH (8 mL) was stirred at reflux for 3 h. Water and DCM were added. The organic layer was washed with brine, dried over MgSO$_4$, filtered and the solvent was evaporated to give 720 mg of crude product. This fraction was purified by preparative LC (Silica 15-40 µm; 12 g GRACE), Mobile phase: gradient from 0.2% NH$_4$OH, 98% DCM, 2% MeOH to 0.5% NH$_4$OH, 95% DCM, 5% MeOH) to give 1-[5-(6,7-dimethoxy-quinazolin-4-ylamino)-4-fluoro-2,3-dihydro-indol-1-yl]-ethanone (500 mg; 97%). $^1$H NMR (500 MHz, DMSO-d$_6$, 300 K) δ 9.42 (s, 1H), 8.31 (s, 1H), 7.87 (d, J=8.5 Hz, 1H), 7.80 (s, 1H), 7.20-7.27 (m, 1H), 7.17 (s, 1H), 4.21 (t, J=8.5 Hz, 2H), 3.93 (s, 6H), 3.21 (t, J=8.5 Hz, 2H), 2.18 (s, 3H).

Step 2

N-(4-fluoroindolin-5-yl)-6,7-dimethoxy-quinazolin-4-amine (hydrochloride salt)

1-[5-(6,7-dimethoxy-quinazolin-4-ylamino)-4-fluoro-2,3-dihydro-indol-1-yl]-ethanone (500 mg; 1.3 mmol) in 37% HCl (8 mL) was refluxed overnight. The water was evaporated to give intermediate 6 as its hydrochloride salt (474 mg; 96%).

Intermediate 7 tert-butyl 5-amino-3,3-difluoro-indoline-1-carboxylate

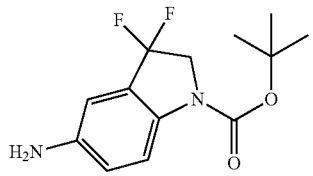 [SMILES: CC(C)(C)OC(=O)N1CC(F)(F)c2cc(N)ccc21]

Step 1 tert-butyl 3,3-difluoro-5-nitro-indoline-1-carboxylate

Di-t-butyl dicarbonate (6.4 g; 29 mmol) was added portionwise to a solution of 3,3-difluoro-5-nitro-indoline (prepared as described in *Tetrahedron* 1999, 55, 1881) (4.9 g; 24 mmol) and 4-dimethylaminopyridine (0.6 g; 5 mmol) in DCM (50 mL) at room temperature. The mixture was stirred at room temperature for 2 hours. The organic layer was washed with K$_2$CO$_3$ (aq) 10%, dried (MgSO$_4$), filtered and the solvent was removed in vacuo to afford the title compound (2.1 g; 28%).

Step 2 tert-butyl 5-amino-3,3-difluoro-indoline-1-carboxylate tert-butyl 3,3-difluoro-5-nitro-indoline-1-carboxylate (0.33 g; 1.1 mmol) was hydrogenated at room temperature in EtOH (3 mL) and THF (1 mL) with 10% Pd/C (0.045 g) as a catalyst at atmospheric pressure. After 12 h, the catalyst was filtered off on a pad of Celite®. The solvent was removed in vacuo to give the title compound which could be used without further purification in the next step (0.29 g; 97%).

Intermediate 8: 1-(5-amino-4-fluoro-indolin-1-yl)-2-(2-methyl-1H-indol-3-yl)ethanone

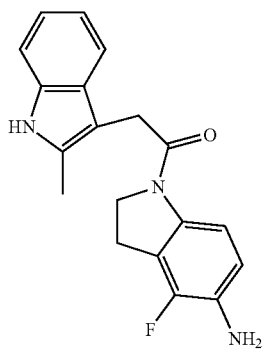 [SMILES: Cc1[nH]c2ccccc2c1CC(=O)N1CCc2c1ccc(N)c2F]

Step 1

1-(4-fluoro-5-nitro-indolin-1-yl)-2-(2-methyl-1H-indol-3-yl)ethanone 2-methylindole-3-acetic acid (purchased from Lancaster Synthesis Ltd.) (519 mg; 2.75 mmol), HATU (1 g; 2.75 mmol) in DMF (6.3 mL) was stirred for 15 min at room temperature. DIPEA (976 µL; 5.7 mmol) followed by 4-fluoro-5-nitro-2,3-dihydroindole (1003858-68-1, prepared as described in US 2007/0287708) (500 mg; 2.3 mmol) were added to the mixture. The reaction mixture was stirred overnight at RT. Water and of 10% K$_2$CO$_3$ (aq) solution were added. This mixture was extracted with EtOAc. The organic layer was dried over MgSO$_4$, filtered and the solvent was removed in vacuo to give 1.3 g crude material. This fraction was purified by preparative LC (Stationary phase: irregular SiOH 15-40 µm 300 g MERCK), Mobile phase: 99% DCM, 1% EtOAc) to give the title compound (460 mg; 57%). $^1$H NMR (500 MHz, DMSO-d6) δ 10.89 (s, 1H), 8.02-8.11 (m, 1H), 7.94 (d, J=8.8 Hz, 1H), 7.43 (d, J=7.9 Hz, 1H), 7.24 (d, J=7.9 Hz, 1H), 6.95-7.01 (m, 1H), 6.87-6.94 (m, 1H), 4.38 (t, J=8.7 Hz, 2H), 3.91 (s, 2H), 3.25 (t, J=8.7 Hz, 2H), 2.35 (s, 3H).

Step 2

1-(5-amino-4-fluoro-indolin-1-yl)-2-(2-methyl-1H-indol-3-yl)ethanone 1-(4-fluoro-5-nitro-indolin-1-yl)-2-(2-methyl-1H-indol-3-yl)ethanone (460 mg; 1.3 mmol) was hydrogenated in a pressure vessel reactor at room temperature in THF (10 mL) and MeOH (15 mL) with Pd/C (10%) (137 mg) as a catalyst at 3 bars pressure of hydrogen for 3 h. The catalyst was filtered off on a pad of Celite®. The Celite® was washed with DCM and MeOH. The solvent was removed in vacuo to give the title compound (468 mg; quantitative).

Intermediates 9-12 were prepared according to the protocol of Intermediate 8 using 5-nitroindoline and the appropriate acetic acid starting material (Table 2)

TABLE 2

| Int. | Structure | Starting Materials |
|---|---|---|
| 9 | 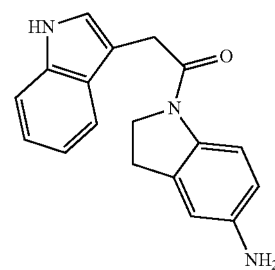 [SMILES: Nc1ccc2c(c1)CCN2C(=O)Cc1c[nH]c2ccccc12] | a) 5-nitroindoline<br>b) indole-3-acetic acid |
| 10 | 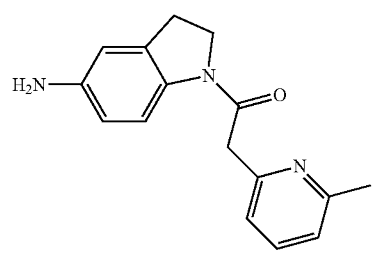 [SMILES: Cc1cccc(CC(=O)N2CCc3cc(N)ccc32)n1] | a) 5-nitroindoline<br>b) 2-(6-methyl-2-pyridyl)acetic acid TFA salt |
| 11 | 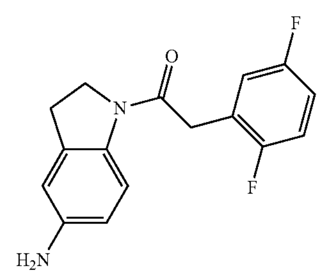 [SMILES: Nc1ccc2c(c1)CCN2C(=O)Cc1cc(F)ccc1F] | a) 5-nitroindoline<br>b) 2,5-difluoro-phenyl acetic acid |
| 12 | 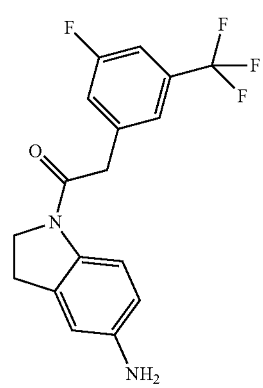 [SMILES: Nc1ccc2c(c1)CCN2C(=O)Cc1cc(F)cc(C(F)(F)F)c1] | a) 5-nitroindoline<br>b) 3-fluoro-5-(trifluoromethyl)-phenylacetic acid |

Preparation of Compounds

Method A

Example 1

1-[5-[(6,7-dimethoxyquinazolin-4-yl)amino]indolin-1-yl]-2-(2-methyl-1H-indol-3-yl)ethanone (compound 1)

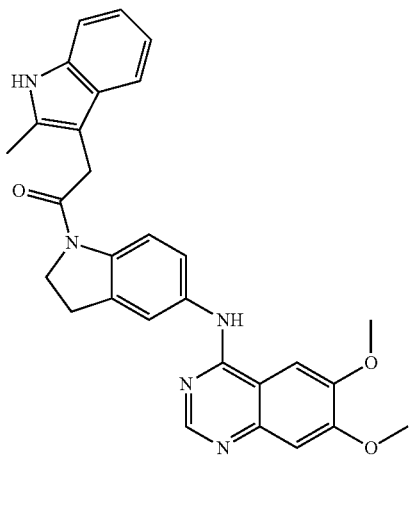

A mixture of intermediate 1 (N-indolin-5-yl-6,7-dimethoxy-quinazolin-4-amine hydrochloride) (0.500 g; 1.39 mmol), HATU (0.69 g; 1.81 mmol), 2-methylindole-3-acetic acid (purchased from Lancaster Synthesis Ltd) (0.32 g; 1.69 mmol) in DMF (10 mL) and DIPEA (0.8 mL; 4.64 mmol) was stirred at RT for a weekend. Water and 30% $NH_4OH$ (aq) were added and this mixture was stirred at room temperature for 30 min. The precipitate was filtered and taken up into EtOAc/MeOH. The organic layer was washed twice with water dried over $MgSO_4$, filtered and the solvent was removed in vacuo to give 588 mg of crude mixture. This fraction was purified by preparative LC (Stationary phase: Sunfire Silica 5 μm 150×30 mm), Mobile phase: gradient from 0.2% $NH_4OH$, 98% DCM, 2% MeOH to 0.8% $NH_4OH$, 92% DCM, 8% MeOH). The pure fractions were combined and the solvent removed in vacuo to give 300 mg. This fraction was taken up into ACN and DIPE, triturated and filtered off. The precipitate was taken up into DCM, dried over $MgSO_4$, filtered and the solvent was removed in vacuo to afford compound 1 (200 mg; 29%).

$^1$H NMR (500 MHz, DMSO-$d_6$, 295 K) δ 10.86 (s, 1H), 9.40 (s, 1H), 8.41 (s, 1H), 8.05 (d, J=8.8 Hz, 1H), 7.82 (s, 1H), 7.73 (s, 1H), 7.49 (d, J=7.6 Hz, 1H), 7.43 (d, J=8.8 Hz, 1H), 7.24 (d, J=8.2 Hz, 1H), 7.16 (s, 1H), 6.95-7.02 (m, 1H), 6.88-6.95 (m, 1H), 4.21 (t, J=8.5 Hz, 2H), 3.94 (s, 3H), 3.92 (s, 3H), 3.84 (s, 2H), 3.18 (t, J=8.5 Hz, 2H), 2.37 (s, 3H).

Compounds 2-38 and compound 53 were prepared according to an analogous reaction protocol as described in example 1 (Table 3)

TABLE 3

| Co. | Structure | Starting Material 1 | Starting Material 2 |
|---|---|---|---|
| 2 | 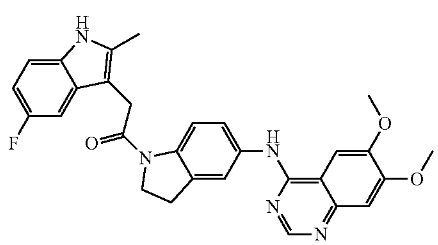 [SMILES: COc1cc2ncnc(Nc3ccc4c(c3)CCN4C(=O)Cc3c(C)[nH]c4ccc(F)cc34)c2cc1OC] | | |
| 3 | 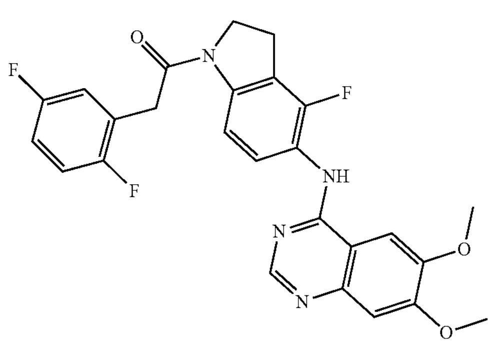 [SMILES: COc1cc2ncnc(Nc3ccc4c(c3F)CCN4C(=O)Cc3cc(F)ccc3F)c2cc1OC] | | |

TABLE 3-continued

| Co. | Structure | Starting Material 1 | Starting Material 2 |
| --- | --- | --- | --- |
| 4 | 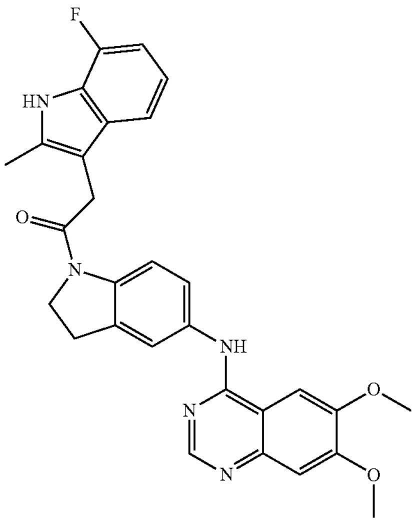 | | |
| 5 | 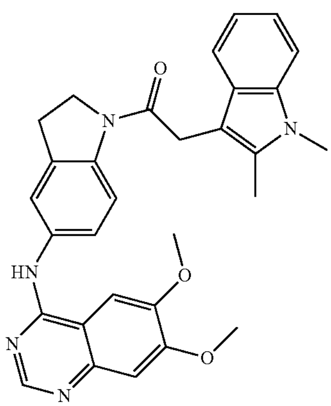 [SMILES: COc1cc2ncnc(Nc3ccc4c(c3)CCN4C(=O)Cc3c(C)n(C)c4ccccc34)c2cc1OC] | | |
| 6 | 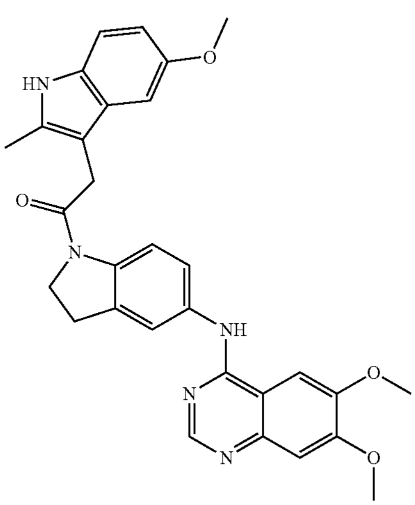 | | |

TABLE 3-continued

| Co. | Structure | Starting Material 1 | Starting Material 2 |
|-----|-----------|---------------------|---------------------|
| 7 | 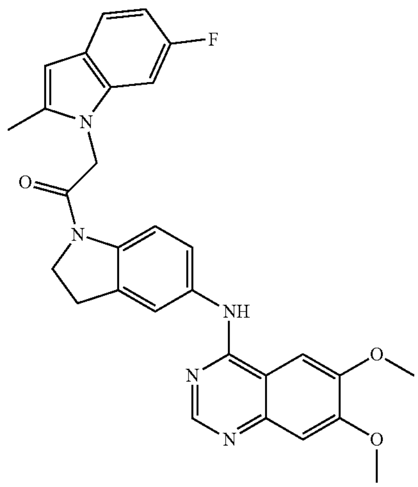 | | |
| 8 | 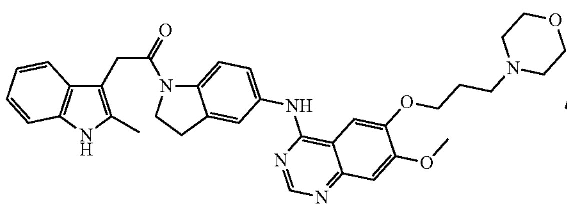 [SMILES: COc1cc2ncnc(Nc3ccc4c(c3)CCN4C(=O)Cc3c(C)[nH]c4ccccc34)c2cc1OCCCN1CCOCC1] | | |
| 9 | 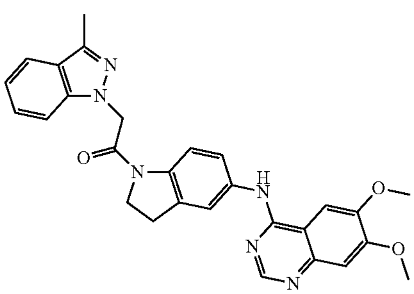 [SMILES: COc1cc2ncnc(Nc3ccc4c(c3)CCN4C(=O)Cn3nc(C)c4ccccc43)c2cc1OC] | | |
| 10 | 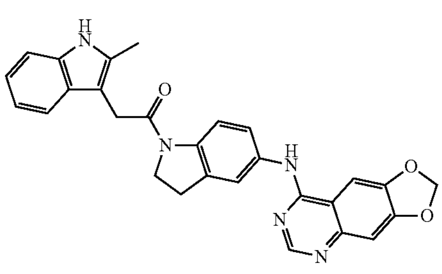 [SMILES: Cc1[nH]c2ccccc2c1CC(=O)N1CCc2cc(Nc3ncnc4cc5c(cc34)OCO5)ccc21] | | |
| 11 | 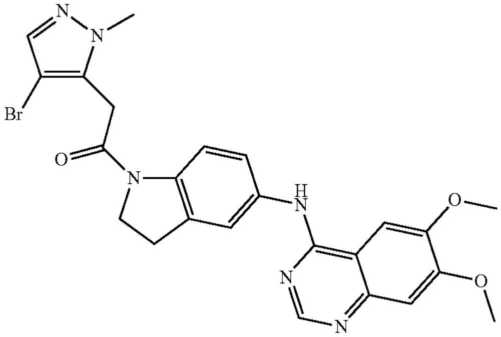 [SMILES: COc1cc2ncnc(Nc3ccc4c(c3)CCN4C(=O)Cc3c(Br)cnn3C)c2cc1OC] | | |

TABLE 3-continued

| Co. | Structure | Starting Material 1 | Starting Material 2 |
|---|---|---|---|
| 12 | 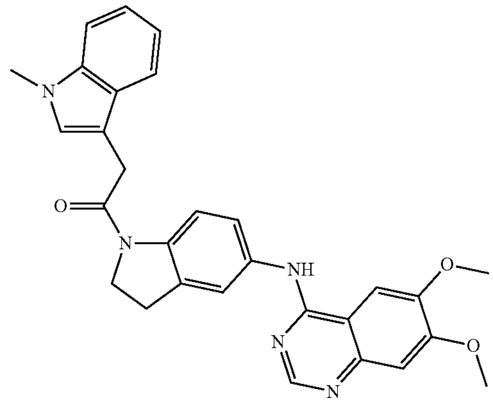 | | |
| 13 | 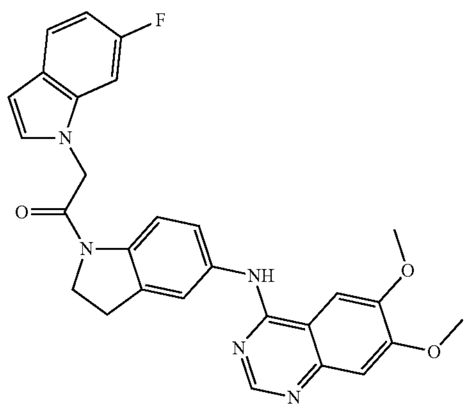 [SMILES: COc1cc2ncnc(Nc3ccc4c(c3)CCN4C(=O)Cn3ccc4ccc(F)cc43)c2cc1OC] | | |
| 14 | 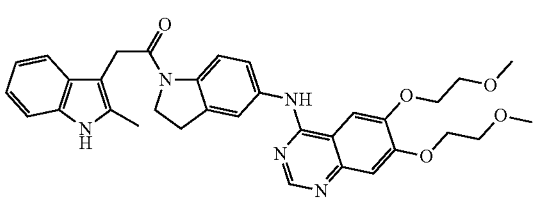 [SMILES: COCCOc1cc2ncnc(Nc3ccc4c(c3)CCN4C(=O)Cc3c(C)[nH]c4ccccc34)c2cc1OCCOC] | | |
| 15 | 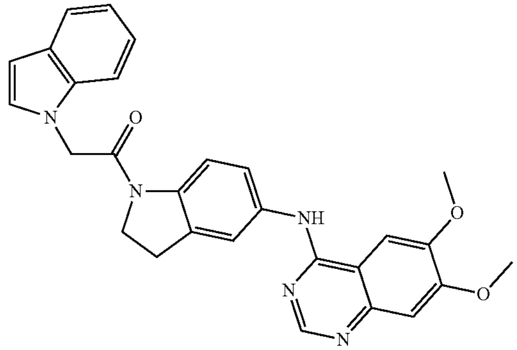 [SMILES: COc1cc2ncnc(Nc3ccc4c(c3)CCN4C(=O)Cn3ccc4ccccc43)c2cc1OC] | | |

TABLE 3-continued
| Co. | Structure | Starting Material 1 | Starting Material 2 |
|---|---|---|---|
| 16 | 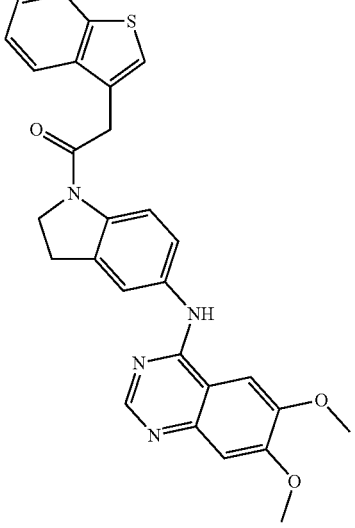 | 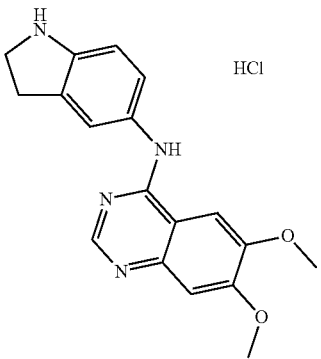 [SMILES: COc1cc2ncnc(Nc3ccc4c(c3)CCN4)c2cc1OC ; Cl] | 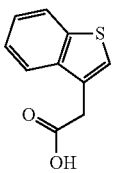 [SMILES: O=C(O)Cc1csc2ccccc12] |
| 17 | 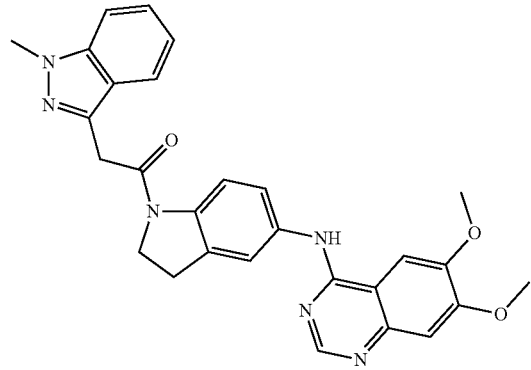 | 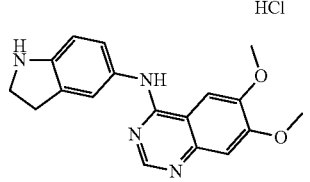 [SMILES: Cl ; COc1cc2ncnc(Nc3ccc4c(c3)CCN4)c2cc1OC] | 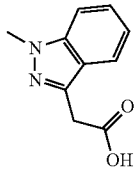 |
| 18 | 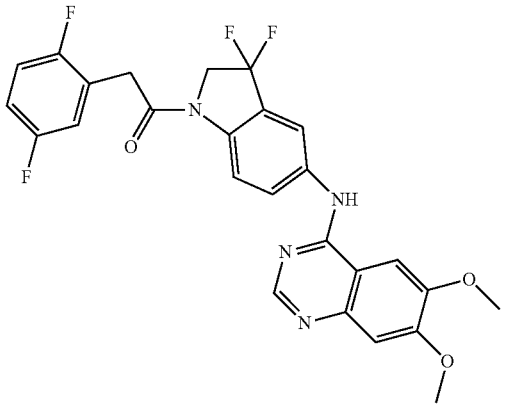 [SMILES: COc1cc2ncnc(Nc3ccc4c(c3)C(F)(F)CN4C(=O)Cc3cc(F)ccc3F)c2cc1OC] | 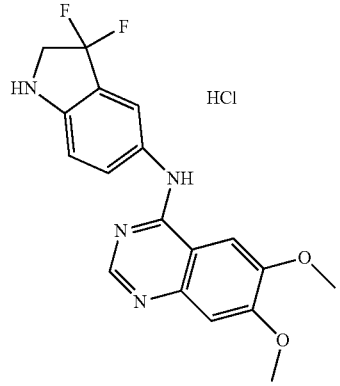 [SMILES: COc1cc2ncnc(Nc3ccc4c(c3)C(F)(F)CN4)c2cc1OC ; Cl] |  |

TABLE 3-continued

| Co. | Structure | Starting Material 1 | Starting Material 2 |
|---|---|---|---|
| 19 | (structure) | (structure) · HCl | (structure) |
| 20 | (structure) | (structure) · HCl | (structure) |
| 21 | (structure) | (structure) · HCl | (structure) |
| 22 | (structure) | (structure) · HCl | (structure) |

TABLE 3-continued

| Co. | Structure | Starting Material 1 | Starting Material 2 |
|-----|-----------|---------------------|---------------------|
| 23  | 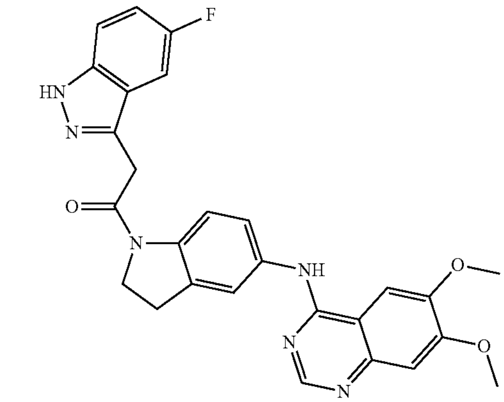 [SMILES: COc1cc2ncnc(Nc3ccc4c(c3)CCN4C(=O)Cc3n[nH]c4ccc(F)cc34)c2cc1OC]          |                     |                     |
| 24  | 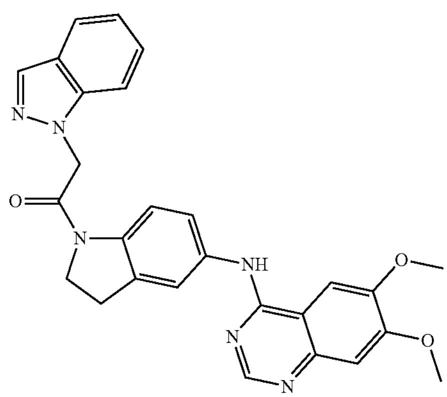          |                     |                     |
| 25  | 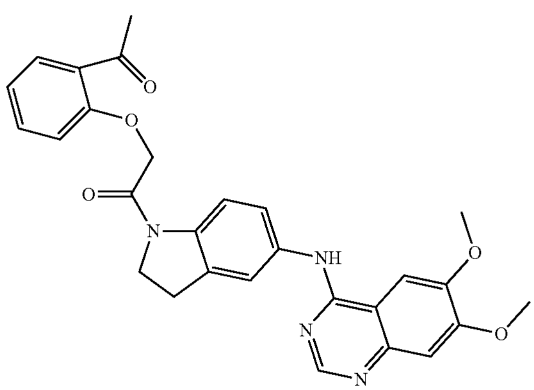 [SMILES: COc1cc2ncnc(Nc3ccc4c(c3)CCN4C(=O)COc3ccccc3C(C)=O)c2cc1OC]          |                     |                     |
| 26  | 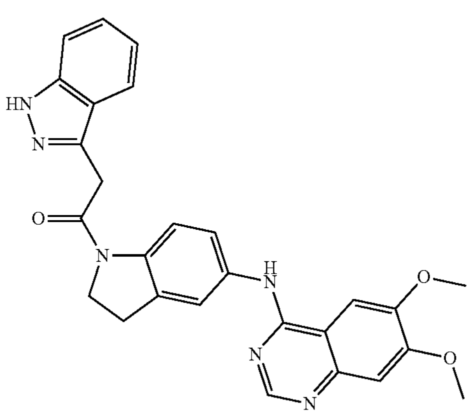 [SMILES: COc1cc2ncnc(Nc3ccc4c(c3)CCN4C(=O)Cc3n[nH]c4ccccc34)c2cc1OC]          |                     |                     |

TABLE 3-continued
| Co. | Structure | Starting Material 1 | Starting Material 2 |
|---|---|---|---|
| 27 | 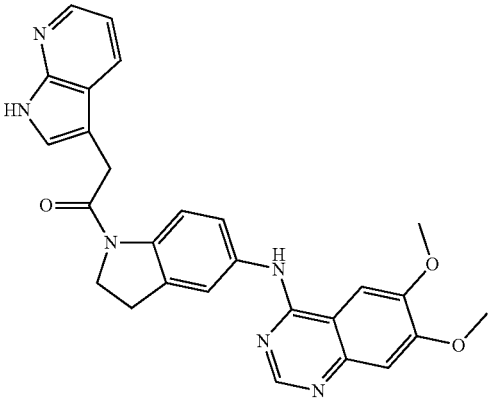 [SMILES: COc1cc2ncnc(Nc3ccc4c(c3)CCN4C(=O)Cc3c[nH]c4ncccc34)c2cc1OC] | 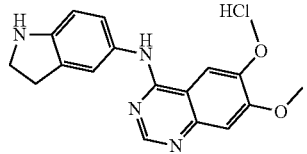 [SMILES: Cl ; COc1cc2ncnc(Nc3ccc4c(c3)CCN4)c2cc1OC] | 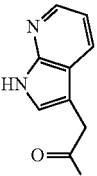 |
| 28 | 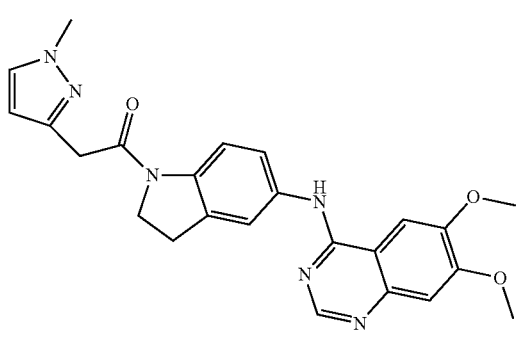 [SMILES: COc1cc2ncnc(Nc3ccc4c(c3)CCN4C(=O)Cc3ccn(C)n3)c2cc1OC] | 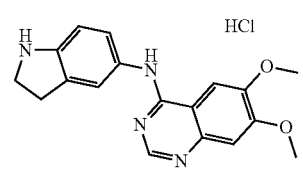 [SMILES: Cl ; COc1cc2ncnc(Nc3ccc4c(c3)CCN4)c2cc1OC] | 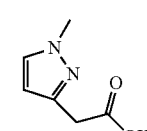 |
| 29 | 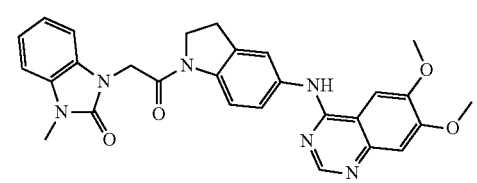 [SMILES: COc1cc2ncnc(Nc3ccc4c(c3)CCN4C(=O)Cn3c(=O)n(C)c4ccccc43)c2cc1OC] | 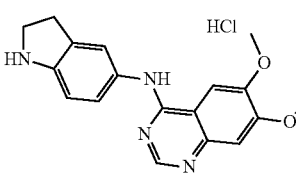 | 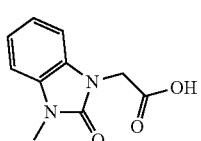 |
| 30 | 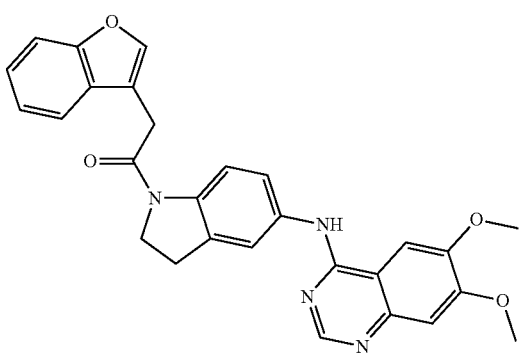 [SMILES: COc1cc2ncnc(Nc3ccc4c(c3)CCN4C(=O)Cc3coc4ccccc34)c2cc1OC] | 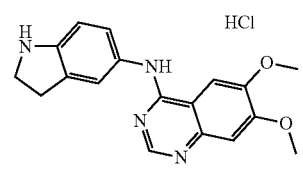 | 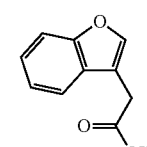 |

TABLE 3-continued

| Co. | Structure | Starting Material 1 | Starting Material 2 |
|---|---|---|---|
| 31 | 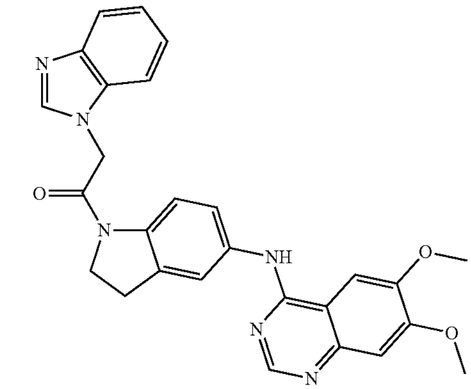 [SMILES: COc1cc2ncnc(Nc3ccc4c(c3)CCN4C(=O)Cn3cnc4ccccc43)c2cc1OC] | | |
| 32 | 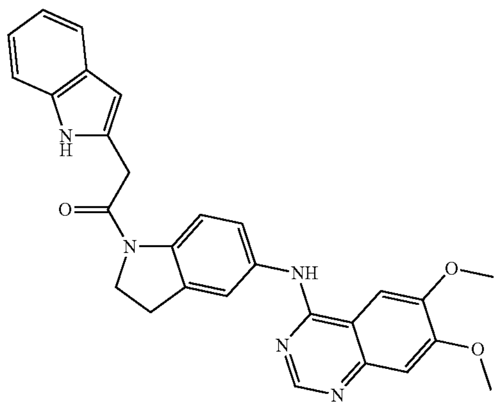 [SMILES: COc1cc2ncnc(Nc3ccc4c(c3)CCN4C(=O)Cc3cc4ccccc4[nH]3)c2cc1OC] | | |
| 33 | 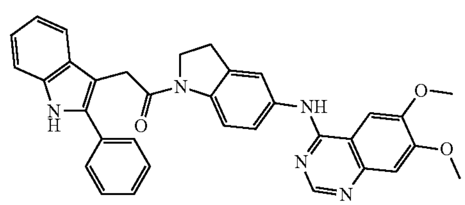 [SMILES: COc1cc2ncnc(Nc3ccc4c(c3)CCN4C(=O)Cc3c(-c4ccccc4)[nH]c4ccccc34)c2cc1OC] | | |
| 34 | 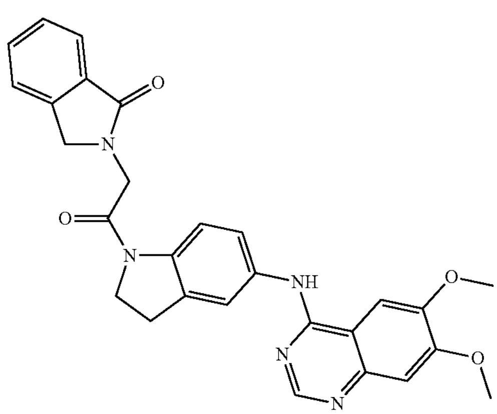 [SMILES: COc1cc2ncnc(Nc3ccc4c(c3)CCN4C(=O)CN3Cc4ccccc4C3=O)c2cc1OC] | | |

TABLE 3-continued

| Co. | Structure | Starting Material 1 | Starting Material 2 |
|---|---|---|---|
| 35 | (2,5-difluorophenyl)acetyl-indoline-5-yl-NH-[1,3]dioxolo[4,5-g]quinazolin-8-yl | indoline-5-yl-NH-[1,3]dioxolo[4,5-g]quinazolin-8-amine·HCl | 2,5-difluorophenylacetic acid |
| 36 | phthalimido-acetyl-indoline-5-yl-NH-(6,7-dimethoxyquinazolin-4-yl) | indoline-5-yl-NH-(6,7-dimethoxyquinazolin-4-yl)·HCl | phthalimidoacetic acid |
| 37 | (1-isopropyl-1H-indol-3-yl)acetyl-indoline-5-yl-NH-(6,7-dimethoxyquinazolin-4-yl) | indoline-5-yl-NH-(6,7-dimethoxyquinazolin-4-yl)·HCl | (1-isopropyl-1H-indol-3-yl)acetic acid |
| 38 | (3-fluoro-5-trifluoromethylphenyl)acetyl-7-azaindoline-5-yl-NH-(6,7-dimethoxyquinazolin-4-yl) | 7-azaindoline-5-yl-NH-(6,7-dimethoxyquinazolin-4-yl)·HCl | 3-fluoro-5-(trifluoromethyl)phenylacetic acid |

TABLE 3-continued

| Co. | Structure | Starting Material 1 | Starting Material 2 |
|---|---|---|---|
| 53 | 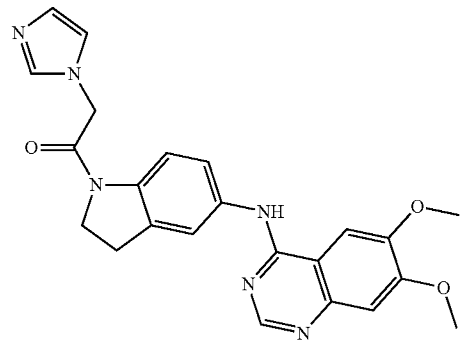 [SMILES: COc1cc2ncnc(Nc3ccc4c(c3)CCN4C(=O)Cn3ccnc3)c2cc1OC] | | |

Method B

Example 39

1-[5-[(6,7-dimethoxyquinazolin-4-yl)amino]-4-fluoro-indolin-1-yl]-2-(2-methyl-1H-indol-3-yl)ethanone (compound 39)

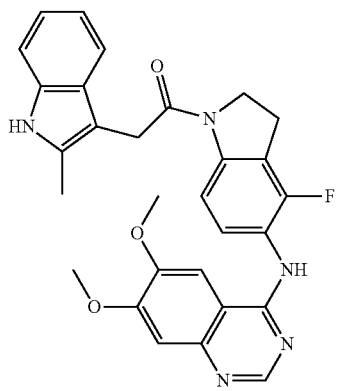 [SMILES: COc1cc2ncnc(Nc3ccc4c(c3F)CCN4C(=O)Cc3c(C)[nH]c4ccccc34)c2cc1OC]

A mixture of 4-chloro-6,7-dimethoxy-quinazoline (292 mg; 1.299 mmol) and intermediate 8 (1-(5-amino-4-fluoro-indolin-1-yl)-2-(2-methyl-1H-indol-3-yl)ethanone) (420 mg; 1.299 mmol) in $^i$PrOH (7.3 mL) was stirred for 4 h at 100° C. Water and DCM were added. The organic layer was dried over $MgSO_4$, filtered and concentrated in vacuo to give 570 mg. This fraction was purified by preparative LC (Stationary phase: Sunfire Silica 5 µm 150×30.0 mm), Mobile phase: gradient from 0.2% $NH_4OH$, 98% DCM, 2% MeOH to 1% $NH_4OH$, 90% DCM, 10% MeOH) to give 214 mg. This fraction was crystallized from $CH_3CN$ and a small quantity of DIPE to give compound 39 (176 mg; 26%). M.pt: 174° C. Kofler. $^1$H NMR (500 MHz, DMSO-d6, 300 K) δ 10.87 (s, 1H), 9.41 (s, 1H), 8.30 (s, 1H), 7.89 (d, J=8.2 Hz, 1H), 7.79 (s, 1H), 7.48 (d, J=7.9 Hz, 1H), 7.19-7.29 (m, 2H), 7.16 (s, 1H), 7.0-6.90 (m, 2H), 4.29 (t, J=8.5 Hz, 2H), 3.92 (s, 6H), 3.87 (s, 2H), 3.21 (t, J=8.5 Hz, 2H), 2.37 (s, 3H).

Compounds 40-45 were prepared according to an analogous reaction protocol as described in example 39 (Table 4)

TABLE 4

| Co. | Structure | Starting Material 1 | Starting Material 2 |
|---|---|---|---|
| 40 | 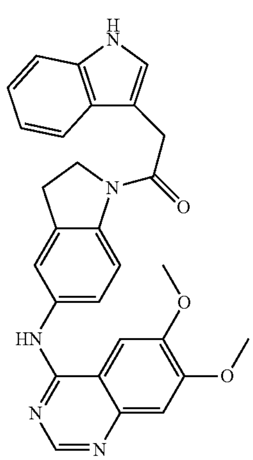 [SMILES: COc1cc2ncnc(Nc3ccc4c(c3)CCN4C(=O)Cc3c[nH]c4ccccc34)c2cc1OC] | | |

TABLE 4-continued

| Co. | Structure | Starting Material 1 | Starting Material 2 |
|---|---|---|---|
| 41 | 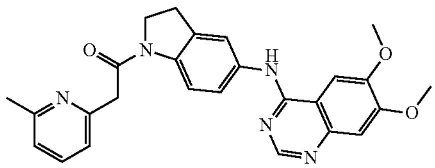 | | |
| 42 | 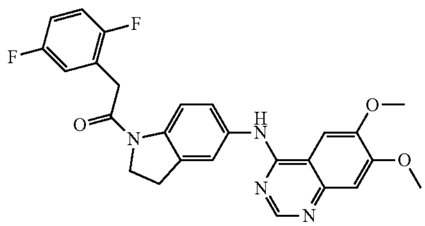 [SMILES: COc1cc2ncnc(Nc3ccc4c(c3)CCN4C(=O)Cc3cc(F)ccc3F)c2cc1OC] | | |
| 43 | 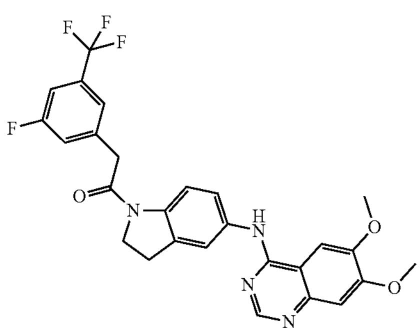 [SMILES: COc1cc2ncnc(Nc3ccc4c(c3)CCN4C(=O)Cc3cc(F)cc(C(F)(F)F)c3)c2cc1OC] | | |
| 44 | 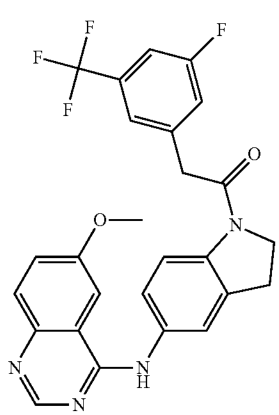 [SMILES: COc1ccc2ncnc(Nc3ccc4c(c3)CCN4C(=O)Cc3cc(F)cc(C(F)(F)F)c3)c2c1] | | |

TABLE 4-continued

| Co. | Structure | Starting Material 1 | Starting Material 2 |
|---|---|---|---|
| 45 | 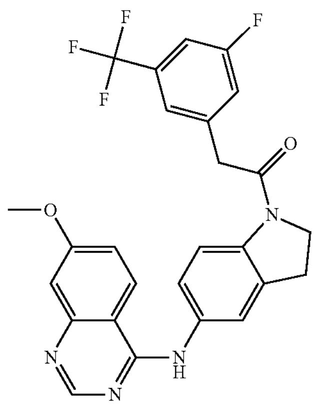 [SMILES: COc1ccc2c(Nc3ccc4c(c3)CCN4C(=O)Cc3cc(F)cc(C(F)(F)F)c3)ncnc2c1] | | |

Method C

Example 46

1-[5-[(6,7-dimethoxyquinazolin-4-yl)amino]indolin-1-yl]-2-[2-methyl-4-(2-thienyl)pyrazol-3-yl]ethanone (compound 46)

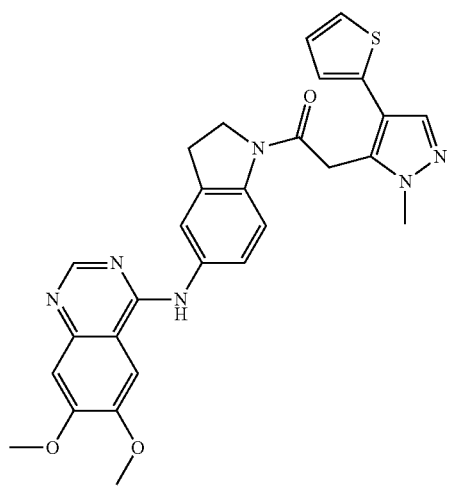 [SMILES: COc1cc2ncnc(Nc3ccc4c(c3)CCN4C(=O)Cc3c(-c4cccs4)cnn3C)c2cc1OC]

Example 47

1-[5-[(6,7-dimethoxyquinazolin-4-yl)amino]indolin-1-yl]-2-(2-methylpyrazol-3-yl)ethanone (compound 47)

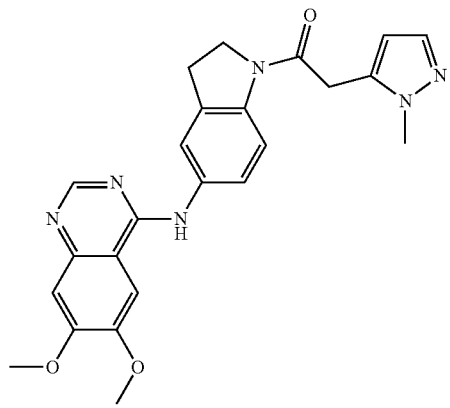 [SMILES: COc1cc2ncnc(Nc3ccc4c(c3)CCN4C(=O)Cc3ccnn3C)c2cc1OC]

A mixture of compound 11 (2-(4-bromo-2-methyl-pyrazol-3-yl)-1-[5-[(6,7-dimethoxyquinazolin-4-yl)amino]indolin-1-yl]ethanone) (0.100 g; 0.19 mmol), chloro(2-dicyclohexylphosphino-2',4',6'-triisopropyl-1,1'-biphenyl) [2-(2'-amino-1,1'-biphenyl)]palladium(II) (12 mg; 0.02 mmol), 2-thiophene boronic acid (0.049 g; 0.38 mmol), potassium phosphate 0.5 M (0.765 mL) in THF (1.50 mL) was heated with stirring in a one single mode microwave (Biotage Initiator EXP 60) at 110° C. with a power output ranging from 0 to 400 W for 5 min. Water and DCM with a fews drops of MeOH were then added. This mixture was filtered over Celite® (diatomaceous earth), washed with DCM/MeOH three times and the organic layer was separated, dried over MgSO$_4$, filtered and the solvent was removed in vacuo to give 70 mg of crude product. The compound was purified by preparative LC (Stationary phase: Spherical bare silica 5 μm 150×30.0 mm), Mobile phase: Gradient from 0.2% NH$_4$OH, 98% DCM, 2% MeOH to 0.8% NH$_4$OH, 92% DCM, 8% MeOH).

The pure fractions of two products were collected and the solvent was removed in vacuo. These two fractions were lyophilized separately (ACN/water 2 mL/5 mL) overnight to give the two title compounds:

1-[5-[(6,7-dimethoxyquinazolin-4-yl)amino]indolin-1-yl]-2-[2-methyl-4-(2-thienyl)pyrazol-3-yl]ethanone (32 mg; 32%). $^1$H NMR (500 MHz, DMSO-d$_6$, 300 K) δ 9.44 (s, 1H), 8.43 (s, 1H), 8.01 (d, J=8.7 Hz, 1H), 7.84 (s, 1H), 7.81 (br s, 1H), 7.64 (s, 1H), 7.47 (d, J=8.7 Hz, 1H), 7.42 (dd, J=5.1, 1.0 Hz, 1H), 7.17 (s, 1H), 7.05-7.09 (m, 2H), 4.32 (t, J=8.4 Hz, 2H), 4.16 (s, 2H), 3.95 (s, 3H), 3.93 (s, 3H), 3.80 (s, 3H), 3.28 (t, J=8.4 Hz, 2H).

1-[5-[(6,7-dimethoxyquinazolin-4-yl)amino]indolin-1-yl]-2-(2-methylpyrazol-3-yl)ethanone (6 mg; 7%). $^1$H NMR (500 MHz, DMSO-d$_6$, 300 K) δ 9.43 (s, 1H), 8.42 (s, 1H), 8.03 (d, J=8.7 Hz, 1H), 7.84 (s, 1H), 7.78 (br s, 1H), 7.47 (d, J=8.7 Hz, 1H), 7.33 (d, J=1.5 Hz, 1H), 7.17 (s, 1H), 6.15 (d, J=1.5 Hz, 1H), 4.25 (t, J=8.4 Hz, 2H), 4.02 (s, 2H), 3.95 (s, 3H), 3.93 (s, 3H), 3.76 (s, 3H), 3.23 (t, J=8.4 Hz, 2H).

Compounds 48-52 were prepared according to the reaction protocol of example 46 (Table 5).

TABLE 5

| Co. | Structure | Starting Material |
|---|---|---|
| 48 | 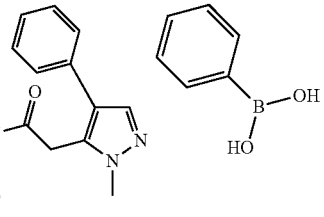 | 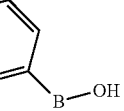 |
| 49 | 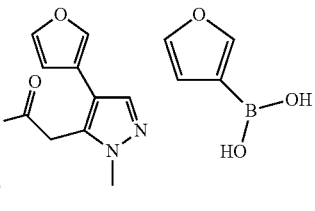 | 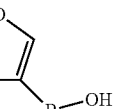 |
| 50 | 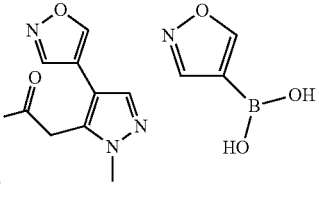 | 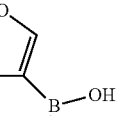 |
| 51 | 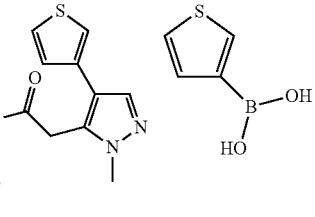 | 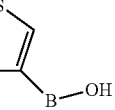 |

TABLE 5-continued

| Co. | Structure | Starting Material |
|---|---|---|
| 52 | 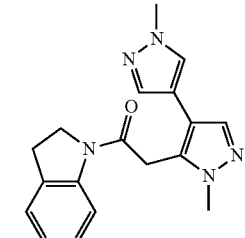 | 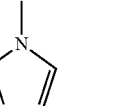 |

$^1$H NMR

Compound 2: $^1$H NMR (500 MHz, DMSO-d$_6$, 295 K) δ 10.97 (s, 1H), 9.41 (s, 1H), 8.42 (s, 1H), 8.05 (d, J=8.6 Hz, 1H), 7.83 (s, 1H), 7.75 (s, 1H), 7.43 (d, J=8.6 Hz, 1H), 7.19-7.29 (m, 2H), 7.16 (s, 1H), 6.81 (td, J=9.1, 2.5 Hz, 1H), 4.22 (t, J=8.5 Hz, 2H), 3.94 (s, 3H), 3.92 (s, 3H), 3.83 (s, 2H), 3.19 (t, J=8.5 Hz, 2H), 2.37 (s, 3H).

Compound 3: $^1$H NMR (500 MHz, DMSO-d$_6$, 295 K) δ 9.44 (s, 1H), 8.32 (s, 1H), 7.85 (d, J=8.5 Hz, 1H), 7.80 (s, 1H), 7.21-7.30 (m, 3H), 7.13-7.21 (m, 2H), 4.36 (t, J=8.5 Hz, 2H), 3.95 (s, 2H), 3.93 (s, 6H), 3.28 (t, J=8.5 Hz, 2H).

Compound 4: $^1$H NMR (500 MHz, DMSO-d$_6$, 295 K) δ 11.31 (s, 1H), 9.41 (s, 1H), 8.41 (s, 1H), 8.04 (d, J=8.8 Hz, 1H), 7.83 (s, 1H), 7.74 (s, 1H), 7.43 (dd, J=8.8, 1.4 Hz, 1H), 7.31 (d, J=7.9 Hz, 1H), 7.16 (s, 1H), 6.88-6.91 (m, 1H), 6.81 (dd, J=11.5, 7.7 Hz, 1H), 4.22 (t, J=8.4 Hz, 2H), 3.94 (s, 3H), 3.92 (s, 3H), 3.86 (s, 2H), 3.20 (t, J=8.4 Hz, 2H), 2.36 (s, 3H).

Compound 5: $^1$H NMR (500 MHz, DMSO-d$_6$, 295 K) δ 9.40 (s, 1H), 8.41 (s, 1H), 8.04 (d, J=8.8 Hz, 1H), 7.82 (s, 1H), 7.74 (s, 1H), 7.53 (d, J=7.9 Hz, 1H), 7.43 (d, J=8.8 Hz, 1H), 7.37 (d, J=8.2 Hz, 1H), 7.16 (s, 1H), 7.05-7.08 (m, 1H), 6.95-6.98 (m, 1H), 4.23 (t, J=8.5 Hz, 2H), 3.94 (s, 3H), 3.92 (s, 3H), 3.89 (s, 2H), 3.68 (s, 3H), 3.18 (t, J=8.5 Hz, 2H), 2.40 (s, 3H).

Compound 6: $^1$H NMR (500 MHz, DMSO-d$_6$, 295 K) δ 10.68 (s, 1H), 9.40 (s, 1H), 8.41 (s, 1H), 8.07 (d, J=8.8 Hz, 1H), 7.82 (s, 1H), 7.74 (br.s, 1H), 7.44 (d, J=8.8 Hz, 1H), 7.16 (s, 1H), 7.13 (d, J=8.6 Hz, 1H), 7.02 (d, J=2.2 Hz, 1H), 6.63 (dd, J=8.6, 2.2 Hz, 1H), 4.19 (t, J=8.4 Hz, 2H), 3.94 (s, 3H), 3.92 (s, 3H), 3.81 (s, 2H), 3.71 (s, 3H), 3.17 (t, J=8.4 Hz, 2H), 2.34 (s, 3H).

Compound 7: $^1$H NMR (500 MHz, DMSO-d$_6$, 300 K) δ 9.43 (s, 1H), 8.43 (s, 1H), 7.94 (d, J=8.6 Hz, 1H), 7.82-7.85 (m, 2H), 7.45-7.49 (m, 1H), 7.41 (dd, J=8.6, 5.4 Hz, 1H), 7.36 (dd, J=10.4, 1.9 Hz, 1H), 7.17 (s, 1H), 6.82 (s, 1H), 6.25 (s, 1H), 5.18 (s, 2H), 4.40 (t, J=8.5 Hz, 2H), 3.95 (s, 3H), 3.93 (s, 3H), 3.31 (t, J=8.5 Hz, 2H—partially obscured by solvent peak), 2.33 (s, 3H).

Compound 8: $^1$H NMR (500 MHz, DMSO-d$_6$, 295 K) δ 10.86 (s, 1H), 9.40 (s, 1H), 8.40 (s, 1H), 8.05 (d, J=8.8 Hz, 1H), 7.82 (s, 1H), 7.72 (s, 1H), 7.49 (d, J=7.9 Hz, 1H), 7.42 (d, J=8.8 Hz, 1H), 7.24 (d, J=7.9 Hz, 1H), 7.15 (s, 1H), 6.99 (m, 1H), 6.91 (m, 1H), 4.09-4.26 (m, 4H), 3.92 (s, 3H), 3.84

(s, 2H), 3.53-3.61 (m, 4H), 3.17 (t, J=8.5 Hz, 2H), 2.47 (m, 2H partially obscured by solvent peak), 2.30-2.42 (m, 7H), 1.98 (m, 2H).

Compound 9: $^1$H NMR (500 MHz, DMSO-d$_6$, 295 K) δ 9.42 (s, 1H), 8.43 (s, 1H), 7.92 (d, J=8.8 Hz, 1H), 7.83 (s, 1H), 7.80 (s, 1H), 7.73 (d, J=7.9 Hz, 1H), 7.58 (d, J=8.5 Hz, 1H), 7.46 (d, J=8.8 Hz, 1H), 7.37 (m, 1H), 7.17 (s, 1H), 7.13 (m, 1H), 5.46 (s, 2H), 4.33 (t, J=8.5 Hz, 2H), 3.94 (s, 3H), 3.92 (s, 3H), 3.29 (t, J=8.5 Hz, 2H), 2.49 (s, 3H—partially obscured by solvent peak).

Compound 10: $^1$H NMR (500 MHz, DMSO-d$_6$, 295 K) δ 10.85 (s, 1H), 9.29 (s, 1H), 8.40 (s, 1H), 8.03 (d, J=8.5 Hz, 1H), 7.96 (s, 1H), 7.75 (s, 1H), 7.49 (d, J=7.6 Hz, 1H), 7.45 (d, J=8.5 Hz, 1H), 7.24 (d, J=7.9 Hz, 1H), 7.15 (s, 1H), 6.95-7.01 (m, 1H), 6.88-6.94 (m, 1H), 6.23 (s, 2H), 4.19 (t, J=8.5 Hz, 2H), 3.84 (s, 2H), 3.16 (t, J=8.5 Hz, 2H), 2.37 (s, 3H).

Compound 11: $^1$H NMR (500 MHz, DMSO-d$_6$, 295 K) δ 9.51 (br. s., 1H), 8.45 (s, 1H), 8.01 (d, J=8.8 Hz, 1H), 7.85 (s, 1H), 7.80 (s, 1H), 7.52 (s, 1H), 7.47 (d, J=8.8 Hz, 1H), 7.17 (s, 1H), 4.33 (t, J=8.5 Hz, 2H), 4.03 (s, 2H), 3.95 (s, 3H), 3.93 (s, 3H), 3.80 (s, 3H), 3.27 (t, J=8.5 Hz, 2H).

Compound 12: $^1$H NMR (500 MHz, DMSO-d$_6$; 295 K) δ 9.41 (s, 1H), 8.41 (s, 1H), 8.07 (d, J=8.8 Hz, 1H), 7.83 (s, 1H), 7.74 (s, 1H), 7.64 (d, J=7.9 Hz, 1H), 7.44 (d, J=8.8 Hz, 1H), 7.40 (d, J=8.2 Hz, 1H), 7.29 (s, 1H), 7.10-7.19 (m, 2H), 7.03 (t, J=7.3 Hz, 1H), 4.25 (t, J=8.5 Hz, 2H), 3.94 (s, 3H), 3.92 (s, 3H), 3.90 (s, 2H), 3.77 (s, 3H), 3.18 (t, J=8.5 Hz, 2H).

Compound 13: $^1$H NMR (500 MHz, DMSO-d$_6$, 295 K) δ 9.42 (s, 1H), 8.43 (s, 1H), 7.95 (d, J=8.7 Hz, 1H), 7.74-7.88 (m, 2H), 7.55 (dd, J=8.7, 5.5 Hz, 1H), 7.47 (d, J=8.7 Hz, 1H), 7.39 (d, J=9.5 Hz, 1H), 7.33 (d, J=3.2 Hz, 1H), 7.17 (s, 1H), 6.85-6.93 (m, 1H), 6.49 (d, J=3.2 Hz, 1H), 5.26 (s, 2H), 4.33 (t, J=8.35 Hz, 2H), 3.95 (s, 3H), 3.93 (s, 3H), 3.30 (t, J=8.5 Hz, 2H—partially obscured by solvent peak).

Compound 14: $^1$H NMR (500 MHz, DMSO-d$_6$, 295 K) δ 10.86 (s, 1H), 9.38 (s, 1H), 8.40 (s, 1H), 8.05 (d, J=8.8 Hz, 1H), 7.85 (s, 1H), 7.74 (s, 1H), 7.49 (d, J=7.9 Hz, 1H), 7.43 (dd, J=8.8 Hz, 1H), 7.25 (d, J=7.9 Hz, 1H), 7.18 (s, 1H), 6.95-7.01 (m, 1H), 6.88-6.94 (m, 1H), 4.24-4.31 (m, 4H), 4.20 (t, J=8.4 Hz, 2H), 3.84 (s, 2H), 3.70-3.80 (m, 4H), 3.36 (s, 3H), 3.35 (s, 3H), 3.17 (t, J=8.4 Hz, 2H), 2.37 (s, 3H).

Compound 15: $^1$H NMR (500 MHz, DMSO-d$_6$, 295 K) δ 9.43 (s, 1H), 8.43 (s, 1H), 7.95 (d, J=8.8 Hz, 1H), 7.73-7.86 (m, 2H), 7.56 (d, J=7.6 Hz, 1H), 7.41-7.51 (m, 2H), 7.33 (d, J=3.2 Hz, 1H), 7.17 (s, 1H),), 7.09-7.14 (m, 1H), 7.00-7.06 (m, 1H), 6.48 (d, J=3.2 Hz, 1H), 5.29 (s, 2H), 4.34 (t, J=8.5 Hz, 2H), 3.95 (s, 3H), 3.92 (s, 3H), 3.29 (t, J=8.5 Hz, 2H—partially obscured by solvent peak).

Compound 16: $^1$H NMR (500 MHz, DMSO-d$_6$, 300 K) δ 8.51 (s, 1H), 8.05 (d, J=8.8 Hz, 1H), 8.00 (d, J=8.5 Hz, 1H), 7.84-7.93 (m, 2H), 7.73 (s, 1H), 7.61 (s, 1H), 7.35-7.47 (m, 3H), 4.32 (t, J=8.4 Hz, 2H), 4.13 (s, 2H), 3.95 (s, 3H), 3.94 (s, 3H), 3.24 (t, J=8.4 Hz, 2H).

Compound 17: $^1$H NMR (500 MHz, DMSO-d$_6$, 300 K) δ 9.42 (s, 1H), 8.42 (s, 1H), 8.03 (d, J=8.5 Hz, 1H), 7.83 (s, 1H), 7.78 (d, J=8.1 Hz, 1H), 7.76 (br s, 1H), 7.60 (d, J=8.5 Hz, 1H), 7.45 (d, J=8.5 Hz, 1H), 7.37-7.42 (m, 1H), 7.16 (s, 1H), 7.10-7.14 (m, 1H), 4.30 (t, J=8.4 Hz, 2H), 4.17 (s, 2H), 4.01 (s, 3H), 3.94 (s, 3H), 3.92 (s, 3H), 3.21 (t, J=8.4 Hz, 2H).

Compound 18: $^1$H NMR (500 MHz, DMSO-d$_6$, 295 K) δ 9.62 (s, 1H), 8.50 (s, 1H), 8.25 (s, 1H), 8.20 (d, J=8.8 Hz, 1H), 7.98 (d, J=8.8 Hz, 1H), 7.85 (s, 1H), 7.13-7.31 (m, 4H), 4.81 (t, J=16.6 Hz, 2H), 4.04 (s, 2H), 3.97 (s, 3H), 3.94 (s, 3H).

Compound 19: $^1$H NMR (500 MHz, DMSO-d$_6$, 300 K) δ 9.47 (s, 1H), 8.43 (s, 1H), 8.27 (d, J=6.6 Hz, 1H), 7.97 (d, J=8.8 Hz, 1H), 7.85 (s, 1H), 7.81 (br s, 1H), 7.43-7.48 (m, 2H), 7.15-7.20 (m, 2H), 6.84 (t, J=6.7 Hz, 1H), 4.38 (t, J=8.5 Hz, 2H), 4.23 (s, 2H), 3.94 (s, 3H), 3.92 (s, 3H), 3.28 (t, J=8.5 Hz, 2H—partially obscured by solvent peak), 2.34 (s, 3H).

Compound 20: $^1$H NMR (500 MHz, DMSO-d$_6$, 300 K) δ 9.43 (s, 1H), 8.42 (s, 1H), 8.06 (d, J=8.4 Hz, 1H), 7.83 (s, 1H), 7.77 (s, 1H) 7.47 (d, J=8.4 Hz, 1H), 7.42 (dd, J=4.7, 1.6 Hz, 1H), 7.17 (s, 1H), 6.98-7.02 (m, 2H), 4.23 (t, J=8.5 Hz, 2H), 4.10 (s, 2H), 3.95 (s, 3H), 39.2 (s, 3H), 3.21 (t, J=8.5 Hz, 2H).

Compound 21: $^1$H NMR (500 MHz, DMSO-d$_6$, 300 K) δ 9.58 (s, 1H), 8.46 (s, 1H), 8.07 (d, J=8.5 Hz, 1H), 7.86 (s, 1H), 7.73 (d, J=1.9 Hz, 1H), 7.45 (dd, J=8.5, 1.9 Hz, 1H), 7.29-7.37 (m, 4H), 7.23-7.28 (m, 1H), 7.17 (s, 1H), 4.21 (t, J=8.4 Hz, 2H), 3.95 (s, 3H), 3.93 (s, 3H), 3.86 (s, 2H), 3.20 (t, J=8.4 Hz, 2H).

Compound 22: $^1$H NMR (500 MHz, DMSO-d$_6$) δ 9.42 (s, 1H), 8.42 (s, 1H), 8.06 (d, J=8.7 Hz, 1H), 7.83 (s, 1H), 7.76 (d, J=1.8 Hz, 1H), 7.50 (dd, J=4.9, 3.0 Hz, 1H), 7.46 (dd, J=8.7 Hz, 1.8 Hz, 1H), 7.34-7.36 (m, 1H), 7.16 (s, 1H), 7.08 (dd, J=4.9, 1.1 Hz, 1H), 4.20 (t, J=8.5 Hz, 2H), 3.95 (s, 3H), 3.92 (s, 3H), 3.86 (s, 2H), 3.20 (t, J=8.5 Hz, 2H).

Compound 23: $^1$H NMR (500 MHz, DMSO-d$_6$, 300 K) δ 12.98 (s, 1H), 9.87 (br. s., 1H), 8.53 (s, 1H), 8.06 (d, J=8.7 Hz, 1H), 7.90 (s, 1H), 7.71 (br.s, 1H), 7.52-7.55 (m, 2H), 7.43 (d, J=8.7 Hz, 1H), 7.22-7.27 (m, 1H), 7.18 (s, 1H), 4.32 (t, J=8.4 Hz, 2H), 4.17 (s, 2H), 3.96 (s, 3H), 3.94 (s, 3H), 3.22 (t, J=8.4 Hz, 2H).

Compound 24: $^1$H NMR (500 MHz, DMSO-d$_6$, 300 K) δ 9.43 (s, 1H), 8.43 (s, 1H), 8.12 (s, 1H), 7.92 (d, J=8.6 Hz, 1H), 7.83 (s, 1H), 7.81 (br s, 1H), 7.80 (d, J=8.2 Hz, 1H), 7.67 (d, J=8.2 Hz, 1H), 7.46 (dd, J=8.6, 1.8 Hz, 1H), 7.37-7.42 (m, 1H), 7.14-7.19 (m, 2H), 5.57 (s, 2H), 4.36 (t, J=8.4 Hz, 2H), 3.94 (s, 3H), 3.92 (s, 3H), 3.29 (t, J=8.4 Hz, 2H).

Compound 25: $^1$H NMR (500 MHz, DMSO-d$_6$, 300 K) δ 9.44 (s, 1H), 8.43 (s, 1H), 8.03 (d, J=8.8 Hz, 1H), 7.81-7.86 (m, 2H), 7.59 (d, J=7.7 Hz, 1H), 7.45-7.54 (m, 2H), 7.21 (d, J=8.2 Hz, 1H), 7.17 (s, 1H), 7.01-7.08 (m, 1H), 5.15 (s, 2H), 4.22 (t, J=8.3 Hz, 2H), 3.95 (s, 3H), 3.93 (s, 3H), 3.26 (t, J=8.3 Hz, 2H), 2.68 (s, 3H).

Compound 26: $^1$H NMR (500 MHz, DMSO-d$_6$, 295 K) δ 12.86 (s, 1H), 9.42 (s, 1H), 8.42 (s, 1H), 8.04 (d, J=8.5 Hz, 1H), 7.83 (s, 1H), 7.74-7.80 (m, 2H), 7.50 (d, J=8.20 Hz, 1H), 7.45 (d, J=8.5 Hz), 7.32-7.37 (m, 1H), 7.16 (s, 1H), 7.08-7.12 (m, 1H), 4.31 (t, J=8.5 Hz, 2H), 4.18 (s, 2H), 3.94 (s, 3H), 3.92 (s, 3H), 3.20 (t, J=8.5 Hz, 2H).

Compound 27: $^1$H NMR (500 MHz, DMSO-d$_6$, 300 K) δ 11.50 (s, 1H), 9.50 (s, 1H), 8.43 (s, 1H), 8.21 (dd, J=4.7, 1.6 Hz, 1H), 8.06 (d, J=8.5 Hz, 1H), 8.01 (dd, J=7.7, 1.6 Hz, 1H), 7.84 (s, 1H), 7.74 (br s, 1H), 7.41-7.46 (m, 2H), 7.16 (s, 1H), 7.05 (dd, J=7.7, 4.7 Hz, 1H), 4.26 (t, J=8.5 Hz, 2H), 3.94 (s, 3H), 3.91-3.93 (m, 5H), 3.20 (t, J=8.5 Hz, 2H).

Compound 28: $^1$H NMR (500 MHz, DMSO-d$_6$, 295 K) δ 9.42 (s, 1H), 8.42 (s, 1H), 8.05 (d, J=8.6 Hz, 1H), 7.83 (s, 1H), 7.75 (d, J=1.8 Hz, 1H), 7.61 (d, J=2.2 Hz, 1H), 7.45 (dd, J=8.6, 1.8 Hz, 1H), 7.16 (s, 1H), 6.14 (d, J=2.2 Hz, 1H), 4.22 (t, J=8.5 Hz, 2H), 3.95 (s, 3H), 3.92 (s, 3H), 3.79 (s, 3H), 3.75 (s, 2H), 3.18 (t, J=8.5 Hz, 2H).

Compound 29: $^1$H NMR (500 MHz, DMSO-d$_6$, 295 K) δ 9.43 (s, 1H), 8.43 (s, 1H), 7.93 (d, J=8.40 Hz, 1H), 7.82 (m, 2H), 7.47 (d, J=8.40 Hz, 1H), 7.13-7.24 (m, 3H), 7.00-7.13 (m, 2H), 4.89 (s, 2H), 4.35 (t, J=7.6 Hz, 2H), 3.94 (s, 3H), 3.92 (s, 3H), 3.34 (m, 5H, obscured by solvent peak).

Compound 30: $^1$H NMR (500 MHz, DMSO-d$_6$, 295 K) δ 9.42 (s, 1H), 8.42 (s, 1H), 8.05 (d, J=8.4 Hz, 1H), 7.96 (s, 1H), 7.83 (s, 1H), 7.78 (s, 1H), 7.69 (d, J=7.6 Hz, 1H), 7.57 (d, J=8.2 Hz, 1H), 7.45 (d, J=8.4 Hz, 1H), 7.23-7.36 (m, 2H), 7.16 (s, 1H), 4.31 (t, J=8.4 Hz, 2H), 3.96 (br s, 2H), 3.95 (s, 3H), 3.92 (s, 3H), 3.24 (t, J=8.4 Hz, 2H).

Compound 31: $^1$H NMR (500 MHz, DMSO-d$_6$, 295 K) δ 9.44 (s, 1H), 8.43 (s, 1H), 8.18 (s, 1H), 7.95 (d, J=8.7 Hz, 1H), 7.83 (m, 2H), 7.68 (d, J=7.5 Hz, 1H), 7.61 (d, J=7.6 Hz, 1H), 7.47 (dd, J=8.7, 2.1 Hz, 1H), 7.20-7.28 (m, 2H), 7.17 (s, 1H), 5.41 (s, 2H), 4.36 (t, J=8.5 Hz, 2H), 3.95 (s, 3H), 3.93 (s, 3H), 3.33 (t, J=8.5 Hz, 2H obscured by solvent peak).

Compound 32: $^1$H NMR (500 MHz, DMSO-d$_6$, 296 K) δ=11.02 (s, 1H), 9.42 (s, 1H), 8.42 (s, 1H), 8.09 (d, J=8.6 Hz, 1H), 7.83 (s, 1H), 7.76 (s, 1H), 7.48 (d, J=8.6 Hz, 1H), 7.45 (d, J=7.9 Hz, 1H), 7.34 (d, J=8.2 Hz, 1H), 7.17 (s, 1H), 7.00-7.05 (m, 1H), 6.92-6.97 (m, 1H), 6.29 (s, 1H), 4.26 (t, J=8.5 Hz, 2H), 4.00 (s, 2H), 3.95 (s, 3H), 3.92 (s, 3H), 3.22 (t, J=8.5 Hz, 2H).

Compound 33: $^1$H NMR (500 MHz, DMSO-d$_6$, 295 K) δ 11.32 (s, 1H), 9.42 (s, 1H), 8.42 (s, 1H), 8.04 (d, J=8.7 Hz, 1H), 7.83 (s, 1H), 7.76 (s, 1H), 7.65 (d, J=7.3 Hz, 2H), 7.57 (d, J=7.9 Hz, 1H), 7.52 (t, J=7.7 Hz, 2H), 7.44 (d, J=8.7 Hz, 1H), 7.36-7.42 (m, 2H), 7.16 (s, 1H), 7.12 (s, 1H), 7.00 (s, 1H), 4.22 (t, J=8.4 Hz, 2H), 4.03 (s, 2H), 3.95 (s, 3H), 3.92 (s, 3H), 3.20 (t, J=8.4 Hz, 2H).

Compound 34: $^1$H NMR (500 MHz, DMSO-d$_6$, 296 K) δ 9.43 (s, 1H), 8.43 (s, 1H), 8.00 (d, J=8.8 Hz, 1H), 7.83 (s, 1H), 7.80 (s, 1H), 7.74 (d, J=7.6 Hz, 1H), 7.61-7.68 (m, 2H), 7.44-7.57 (m, 2H), 7.17 (s, 1H), 4.58 (s, 2H), 4.57 (s, 2H), 4.25 (t, J=8.1 Hz, 2H), 3.95 (s, 3H), 3.94 (s, 3H), 3.26 (t, J=8.1 Hz, 2H).

Compound 35: $^1$H NMR (500 MHz, DMSO-d$_6$, 300K) δ 9.31 (s, 1H), 8.42 (s, 1H), 7.95-8.00 (m, 2H), 7.79 (s, 1H), 7.49 (d, J=8.5 Hz, 1H), 7.13-7.30 (m, 4H), 6.23 (s, 2H), 4.26 (t, J=8.4 Hz, 2H), 3.92 (s, 2H), 3.24 (t, J=8.4 Hz, 2H).

Compound 36: $^1$H NMR (500 MHz, DMSO-d$_6$, 300 K) δ 9.45 (s, 1H), 8.43 (s, 1H), 7.88-7.99 (m, 5H), 7.83 (s, 1H), 7.81 (s, 1H), 7.47 (d, J=8.5 Hz, 1H), 7.16 (s, 1H), 4.67 (s, 2H), 4.34 (t, J=8.3 Hz, 2H), 3.94 (s, 3H), 3.92 (s, 3H), 3.28 (t, J=8.3 Hz, 2H).

Compound 37: $^1$H NMR (500 MHz, DMSO-d$_6$, 300 K) δ 9.41 (s, 1H), 8.41 (s, 1H), 8.07 (d, J=8.5 Hz, 1H), 7.83 (s, 1H), 7.74 (d, J=1.3 Hz, 1H), 7.63 (d, J=7.9 Hz, 1H), 7.48 (d, J=8.5 Hz, 1H), 7.41-7.46 (m, 2H), 7.16 (s, 1H), 7.11-7.15 (m, 1H), 6.99-7.03 (m, 1H), 4.70-4.77 (m, 1H), 4.26 (t, J=8.5 Hz, 2H), 3.94 (s, 3H), 3.92 (s, 3H), 3.91 (s, 2H), 3.20 (t, J=8.5 Hz, 2H), 1.46 (s, 3H), 1.45 (s, 3H).

Compound 38: $^1$H NMR (500 MHz, DMSO-d$_6$, 295 K) δ 9.65 (br. s., 1H), 8.43 (s, 1H), 8.41 (s, 1H), 8.11 (s, 1H), 7.83 (s, 1H), 7.47-7.62 (m, 3H), 7.17 (s, 1H), 4.60 (s, 2H), 4.05 (t, J=8.1 Hz, 2H), 3.95 (s, 3H), 3.93 (s, 3H), 3.12 (t, J=8.1 Hz, 2H).

Compound 40: $^1$H NMR (500 MHz, DMSO-d$_6$, 300 K) δ 9.40 (s, 1H), 8.41 (s, 1H), 8.07 (d, J=8.8 Hz, 1H), 7.83 (s, 1H), 7.74 (s, 1H), 7.63 (d, J=7.9 Hz, 1H), 7.44 (d, J=8.8 Hz, 1H), 7.36 (d, J=7.9 Hz, 1H), 7.27-7.32 (m, 1H), 7.16 (s, 1H), 7.06-7.10 (m, 1H), 6.95-7.01 (m, 1H), 4.24 (t, J=8.5 Hz, 2H), 3.10-3.21 (m, 2H).

Compound 41: $^1$H NMR (500 MHz, DMSO-d$_6$, 297 K) δ 9.42 (s, 1H), 8.42 (s, 1H), 8.04 (d, J=8.5 Hz, 1H), 7.83 (s, 1H), 7.76 (s, 1H), 7.65 (d, J=7.6 Hz, 1H), 7.46 (d, J=8.5 Hz, 1H), 7.09-7.20 (m, 3H), 4.26 (t, J=8.4 Hz, 2H), 3.97 (s, 2H), 3.95 (s, 3H), 3.92 (s, 3H), 3.21 (t, J=8.4 Hz, 2H), 2.45 (s, 3H).

Compound 42: $^1$H NMR (500 MHz, DMSO-d$_6$, 295 K) δ 9.42 (s, 1H), 8.42 (s, 1H), 8.00 (d, J=8.6 Hz, 1H), 7.84 (s, 1H), 7.78 (s, 1H), 7.46 (d, J=8.6 Hz, 1H), 7.14-7.29 (m, 4H), 4.27 (t, J=8.4 Hz, 2H), 3.95 (s, 2H), 3.93 (s, 6H), 3.25 (t, J=8.4 Hz, 2H).

Compound 43: $^1$H NMR (500 MHz, DMSO-d$_6$, 300 K) δ 9.42 (s, 1H), 8.43 (s, 1H), 8.03 (d, J=8.8 Hz, 1H), 7.83 (s, 1H), 7.79 (br s, 1H), 7.56-7.61 (m, 2H), 7.51 (d, J=9.5 Hz, 1H), 7.46 (dd, J=8.7, 1.7 Hz, 1H), 7.17 (s, 1H), 4.25 (t, J=8.5 Hz, 2H), 4.05 (s, 2H), 3.95 (s, 3H), 3.92 (s, 3H), 3.25 (t, J=8.5 Hz, 2H).

Compound 44: $^1$H NMR (500 MHz, DMSO-d$_6$, 300 K) δ 9.58 (s, 1H), 8.46 (s, 1H), 8.04 (d, J=8.8 Hz, 1H), 7.91 (d, J=2.6 Hz, 1H), 7.82 (s, 1H), 7.71 (d, J=9.2 Hz, 1H), 7.56-7.61 (m, 2H), 7.46-7.58 (m, 3H), 4.26 (t, J=8.4 Hz, 2H), 4.05 (s, 2H), 3.94 (s, 3H), 3.92 (s, 3H), 3.26 (t, J=8.4 Hz, 2H—partially obscured by solvent peak), 2.34 (s, 3H).

Compound 45: $^1$H NMR (500 MHz, DMSO-d$_6$, 300 K) δ 9.61 (s, 1H), 8.50 (s, 1H), 8.43 (d, J=9.4 Hz, 1H), 8.01 (d, J=8.5 Hz, 1H), 7.81 (br s, 1H), 7.56-7.60 (m, 2H), 7.49-7.53 (m, 2H), 7.22 (dd, J=9.1, 2.5 Hz, 1H), 7.16 (d, J=2.5 Hz, 1H), 4.25 (t, J=8.5 Hz, 2H), 4.04 (s, 2H), 3.92 (s, 3H), 3.24 (t, J=8.5 Hz, 2H).

Compound 48: $^1$H NMR (500 MHz, DMSO-d$_6$, 300 K) δ 9.43 (br.s, 1H), 8.43 (s, 1H), 8.05 (d, J=8.5 Hz, 1H), 7.84 (s, 1H), 7.81 (br.s, 1H), 7.61 (s, 1H), 7.49 (d, J=8.5 Hz, 1H), 7.31-7.43 (m, 4H), 7.22-7.29 (m, 1H), 7.17 (s, 1H), 4.27 (t, J=8.2 Hz, 2H), 4.08 (s, 2H), 3.96 (s, 3H), 3.93 (s, 3H), 3.80 (s, 3H), 3.25 (t, J=8.2 Hz, 3H—partially obscured by solvent peak).

Compound 49: $^1$H NMR (400 MHz, DMSO-d$_6$, 298 K) δ 9.42 (s, 1H), 8.43 (s, 1H), 8.00 (d, J=8.7 Hz, 1H), 7.84 (s, 1H), 7.76-7.82 (m, 2H), 7.67-7.70 (m, 1H), 7.58 (s, 1H), 7.47 (d, J=8.7 Hz, 1H), 7.17 (s, 1H), 6.67 (s, 1H), 4.33 (t, J=8.5 Hz, 2H), 4.09 (s, 2H), 3.95 (s, 3H), 3.93 (s, 3H), 3.26 (t, J=8.5 Hz, 2H partially obscured by solvent peak).

Compound 50: $^1$H NMR (500 MHz, DMSO-d$_6$, 298 K) δ 9.44 (s, 1H), 9.10 (s, 1H), 8.88 (s, 1H), 8.43 (s, 1H), 7.99 (d, J=8.7 Hz, 1H), 7.84 (s, 1H), 7.81 (s, 1H), 7.69 (s, 1H), 7.47 (d, J=8.7 Hz, 1H), 7.17 (s, 1H), 4.34 (t, J=8.4 Hz, 2H), 4.14 (s, 2H), 3.95 (s, 3H), 3.92 (s, 3H), 3.78 (s, 3H), 3.27 (t, J=8.4 Hz, 2H—partially obscured by solvent peak).

Compound 51: $^1$H NMR (500 MHz, DMSO-d$_6$, 295 K) δ 9.44 (s, 1H), 8.43 (s, 1H), 8.02 (d, J=8.8 Hz, 1H), 7.84 (s, 1H), 7.81 (b.s, 1H), 7.64 (s, 1H), 7.56-7.61 (m, 1H), 7.47 (dd, J=8.8, 1.8 Hz, 1H), 7.38 (d, J=1.8 Hz, 1H), 7.22-7.25 (m, 1H), 7.17 (s, 1H), 4.32 (t, J=8.5 Hz, 2H), 4.13 (s, 2H), 3.95 (s, 3H), 3.93 (s, 3H), 3.78 (s, 3H), 3.26 (t, J=8.5 Hz, 2H).

Compound 52: $^1$H NMR (400 MHz, DMSO-d$_6$, 300 K) δ 9.42 (br.s, 1H), 8.43 (s, 1H), 8.01 (d, J=9.1 Hz, 1H), 7.84 (s, 1H), 7.80 (br.s, 1H), 7.76 (s, 1H), 7.45-7.51 (m, 3H), 7.17 (s, 1H), 4.31 (t, J=8.6 Hz, 2H), 4.05 (s, 2H), 3.95 (s, 3H), 3.93 (s, 3H), 3.83 (s, 3H), 3.75 (s, 3H), 3.26 (t, J=8.6 Hz, 2H—partially obscured by solvent peak).

Compound 53: $^1$H NMR (500 MHz, DMSO-d$_6$, 300K) δ 9.44 (s, 1H), 8.43 (s, 1H), 8.00 (d, J=8.7 Hz, 1H), 7.83 (s, 1H), 7.80 (br. s, 1H), 7.67 (s, 1H), 7.48 (d, J=8.7 Hz, 1H), 7.14-7.19 (m, 2H), 6.95 (s, 1H), 5.14 (s, 2H), 4.21 (t, J=8.5 Hz, 2H), 3.95 (s, 3H), 3.93 (s, 3H), 3.27 (t, J=8.5 Hz, 2H-partially obscured by the solvent).

Liquid Chromatography/Mass Spectrometry (LCMS) and Melting Points (M.Pt)

LCMS Procedure

The LC measurement was performed using a UPLC (Ultra Performance Liquid Chromatography) Acquity (Waters) system comprising a binary pump with degasser, an autosampler, a diode-array detector (PDA) and a column as specified in the respective methods below, the column is held at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system. Reversed phase UPLC was carried out on a Waters Acquity BEH (bridged ethylsiloxane/silica hybrid) C18 column (1.7 µm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (held for 0.49 minute) to 10.5% A and 89.5% B in 2.18 minutes, held for 1.94 minutes and back to the initial conditions in 0.73 minute, held for 0.73 minute. An injection volume of 2 µl was used. Cone voltage was 20V for positive and negative ionization mode. Mass spectra were acquired by scanning from 100 to 1000 in 0.2 seconds using an interscan delay of 0.1 seconds.

Melting Points

For a number of compounds, melting points were obtained with a Kofler hot bench, consisting of a heated plate with linear temperature gradient, a sliding pointer and a temperature scale in degrees Celsius.

The results of the analytical measurements are shown in table 6.

TABLE 6

Retention time ($R_t$) in min., $[M + H]^+$ peak (protonated molecule), and M.pt (melting point in ° C.). (n.d. means not determined)

| Co. No. | $R_t$ | $[M + H]^+$ | M.pt (° C.) |
| --- | --- | --- | --- |
| 1 | 2.61 | 494 | n.d. |
| 2 | 2.63 | 512 | n.d. |
| 3 | 2.67 | 495 | 210 |
| 4 | 2.68 | 512 | n.d. |
| 5 | 2.83 | 508 | 168 |
| 6 | 2.55 | 524 | n.d. |
| 7 | 2.88 | 512 | n.d. |
| 8 | 2.55 | 607 | 216 |
| 9 | 2.60 | 495 | n.d. |
| 10 | 2.65 | 478 | n.d. |
| 11 | 2.41 | 523 | 170 |
| 12 | 2.78 | 494 | n.d. |
| 13 | 2.79 | 498 | n.d. |
| 14 | 2.66 | 582 | 186 |
| 15 | 2.75 | 480 | 176 |
| 16 | 2.87 | 497 | 161 |
| 17 | 2.53 | 495 | 158 |
| 18 | 2.92 | 513 | n.d. |
| 19 | 2.19 | 495 | n.d. |
| 20 | 2.57 | 447 | 219 |
| 21 | 2.62 | 441 | n.d. |
| 22 | 2.56 | 447 | n.d. |
| 23 | 2.43 | 499 | n.d. |
| 24 | 2.52 | 481 | n.d. |
| 25 | 2.53 | 499 | n.d. |
| 26 | 2.37 | 481 | n.d. |
| 27 | 2.23 | 481 | n.d. |
| 28 | 2.15 | 445 | 199 |
| 29 | 2.40 | 511 | n.d. |
| 30 | 2.76 | 481 | 165 |
| 31 | 2.27 | 481 | n.d. |
| 32 | 2.69 | 480 | n.d. |
| 33 | 2.89 | 556 | n.d. |
| 34 | 2.31 | 496 | n.d. |
| 36 | 2.48 | 510 | 190 |
| 37 | 3.02 | 522 | n.d. |

TABLE 6-continued

Retention time ($R_t$) in min., $[M + H]^+$ peak (protonated molecule), and M.pt (melting point in ° C.). (n.d. means not determined)

| Co. No. | $R_t$ | $[M + H]^+$ | M.pt (° C.) |
| --- | --- | --- | --- |
| 38 | 2.99 | 528 | n.d. |
| 39 | 2.60 | 512 | 174 |
| 40 | 2.59 | 480 | 180 |
| 41 | 2.30 | 456 | 248 |
| 42 | 2.73 | 477 | >260 |
| 43 | 2.98 | 527 | n.d. |
| 44 | 3.06 | 497 | n.d. |
| 45 | 3.03 | 497 | n.d. |
| 46 | 2.52 | 527 | n.d. |
| 47 | 2.12 | 445 | n.d. |
| 48 | 2.56 | 521 | n.d. |
| 49 | 2.39 | 511 | n.d. |
| 50 | 2.22 | 512 | n.d. |
| 51 | 2.50 | 527 | n.d. |
| 52 | 2.09 | 525 | n.d. |
| 35 | 2.73 | 461 | n.d. |
| 53 | 1.97 | 431 | 174 |

Pharmacology i) In-Vitro PERK Enzyme Inhibition Assay (KIN_PERK pIC50)

The compounds of the invention were tested for inhibitory activity against PERK in an enzyme inhibition assay.

A biochemical PERK kinase assay using LanthaScreen® technology from Invitrogen using recombinant GST-PERK (Invitrogen PV5106), GFP-eIF2 alpha (full length) as substrate (Invitrogen PV4809) and the Terbium-labeled antibody (Tb-anti-peIF2alpha (pSer52); Invitrogen PV4816) as detection reagent, was performed essentially as described by the manufacturer, using following specific parameters: Compounds, dissolved in DMSO, were incubated in a reaction mix consisting of 50 mM Tris pH 7.5, 1 mM EGTA, 0.01% Tween® 20, 10 mM MgCl2, 1 mM DTT, 200 nM GFP-eIF2 alpha, 12.5 ng/ml PERK, 5 µM ATP for 60 minutes at room temperature. The reaction was stopped using 20 mM EDTA and after 30 minutes of incubation at room temperature, 2 nM LanthaScreen® Tb-anti-peIF2alpha (pSer52) antibody was added before measuring in an Envision instrument using following wavelengths (nm): Ex337_Em 520/Em 495.

ii) cell-based PERK inhibition assay (P-eIF2alpha_Lantha_cell pIC50)

The potential for the compounds of the invention to inhibit PERK activity in a cell-based context may be demonstrated using the cell-based assay.

A cell-based TR-FRET assay to measure inhibition of phosphorylation of GFP-eIF2 alpha expressed in HEK293 cells by compounds was set up as follows:

LanthaScreen® eIF2α GripTite cells (Invitrogen M4387) were plated and incubated for 16-20 h at 37° C. and 5% CO$_2$, incubated with test compounds for 60 min, and then stimulated with tunicamycin (2 microg/ml) for 120 min. Culture medium was aspirated from the wells and, the cells were lysed in LanthaScreen® Cellular Assay Lysis Buffer (Invitrogen; PV5598), supplemented with protease inhibitor cocktail (Sigma P8340, 1/1000 dilution) and phosphatase inhibitor cocktail (Sigma P0044, 1/1000 dilution), including 2 nM terbium-labeled eIF2a pSer52 antibody (Invitrogen; PV4816). After 2 hours of incubation at room temperature in the dark with slow shaking (200 rpm), the assay plate was measured in an Envision instrument using following wavelengths (nm): Ex337_Em 520/Em 495.

Compounds were assayed in the above described biochemical and cell-based assays (example i; ii) and results are reported as $pIC_{50}$ activities in Table 7.

TABLE 7

| Co. No. | KIN_PERK pIC50 | P-eIF2alpha_Lantha_cell pIC50 |
|---|---|---|
| 1 | 9.1 | 7.7 |
| 2 | 9.2 | 7.6 |
| 3 | 9.4 | 7.3 |
| 4 | 8.8 | 7.4 |
| 5 | 8.9 | 7.2 |
| 6 | 8.8 | 7.1 |
| 7 | 8.5 | 7.1 |
| 8 | n.d. | 6.8 |
| 9 | 7.8 | 6.6 |
| 10 | 8.4 | 6.8 |
| 11 | 8.1 | 6.6 |
| 12 | 8.3 | 6.7 |
| 13 | 8.4 | 6.7 |
| 14 | n.d. | 6.4 |
| 15 | 8.2 | ~6.52 |
| 16 | 8.3 | 6.3 |
| 17 | 7.7 | 6.1 |
| 18 | 7.5 | 6.1 |
| 19 | 7.9 | 5.9 |
| 20 | 7.5 | 5.9 |
| 21 | 7.6 | 5.9 |
| 22 | 7.2 | 5.7 |
| 23 | 7.5 | 5.7 |
| 24 | 7.1 | 5.5 |
| 25 | 7.1 | 5.5 |
| 26 | 7.2 | 5.5 |
| 27 | 7.2 | 5.4 |
| 28 | 6.6 | 5.1 |
| 29 | 7.3 | <4.52 |
| 30 | 8.0 | <4.52 |
| 31 | 7.2 | <4.52 |
| 32 | 6.4 | <4.52 |
| 33 | 5.2 | n.d. |
| 34 | 5.8 | n.d. |
| 35 | <5 | n.d. |
| 36 | 5.5 | n.d. |
| 37 | 5.8 | n.d. |
| 38 | 5.5 | n.d. |
| 53 | <5 | <5 |
| 39 | 9.0 | 7.9 |
| 40 | 7.9 | 6.2 |
| 41 | n.d. | 6.1 |
| 42 | 8.2 | 6.2 |
| 43 | 8.7 | 5.8 |
| 44 | ~7.67 | <4.52 |
| 45 | 7.4 | <4.52 |
| 46 | 6.4 | ~4.94 |
| 47 | 7.2 | 5.2 |
| 48 | 6.6 | 5.9 |
| 49 | 7.3 | 5.5 |
| 50 | 7.1 | 5.5 |
| 51 | 6.6 | 4.5 |
| 52 | 6.2 | <4.52 |

Composition Examples

"Active ingredient" (a.i.) as used throughout these examples relates to a compound of Formula (I), including any tautomer or stereoisomeric form thereof, or a pharmaceutically acceptable addition salt or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A compound of Formula (I)

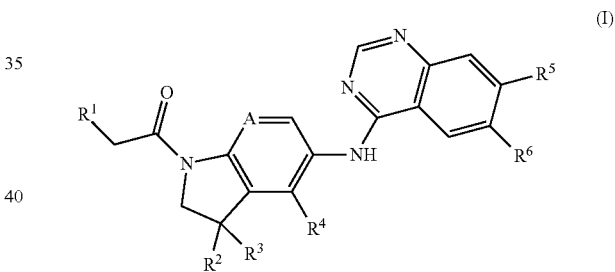

a tautomer or a stereoisomeric form thereof, wherein
$R^1$ is —$Ar^1$, —O—$Ar^1$ or —NH—$Ar^1$;
$Ar^1$ is phenyl, pyridinyl, indazolyl, pyrazolyl, indolyl, imidazolyl, benzimidazolyl, thienyl, quinazolinyl, benzo[b]thienyl, benzofuranyl, 1H-pyrrolo[2,3-b]pyridinyl, imidazo[1,2-a]pyridinyl, 1,3-dihydro-1-oxo-2H-isoindolyl, 1,3-dihydro-1,3-dioxo-2H-isoindolyl, naphthyl, isoquinolinyl, quinolinyl, cinnolinyl, furanyl or 2,3-dihydro-2-oxo-1H-benzimidazolyl;
each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ and $C_{1-4}$alkyl substituted with one or more halo atoms;
$Ar^2$ is phenyl, thienyl, furanyl, isoxazolyl, oxazolyl or pyrazolyl; each optionally substituted with 1, 2 or 3 $C_{1-4}$alkyl groups;
$R^2$ and $R^3$ are the same and are hydrogen or fluoro;
A is CH or N;
$R^4$ is hydrogen, chloro or fluoro;
$R^5$ is hydrogen, —$OR^7$ or —O—$(CH_2)_m$—O—$R^7$;
$R^6$ is hydrogen, —$OR^8$ or —O—$(CH_2)_m$—O—$R^8$;
provided that at least one of $R^5$ and $R^6$ is not hydrogen;

or $R^5$ and $R^6$ are taken together to form the bivalent radical —O—$(CH_2)_n$—O—;

n is 1, 2 or 3;

m is 1, 2, 3 or 4;

$R^7$ is $C_{1-4}$alkyl optionally substituted with one $NR^{9a}R^{10a}$;

$R^8$ is $C_{1-4}$alkyl optionally substituted with one $NR^{9b}R^{10b}$;

R9a and a $R^{10a}$ each independently are hydrogen or $C_{1-4}$alkyl; or $R^{9a}$ and $R^{10a}$ are taken together with the nitrogen to which they are attached to form a saturated monocyclic 4, 5, 6 or 7-membered heterocycle which may further contain one additional heteroatom selected from O, S, S(=O)$_p$ or N; and which heterocycle may optionally be substituted with 1, 2 or 3 substituents each independently selected from the group consisting of halo and $C_{1-4}$alkyl;

$R^{9b}$ and $R^{10b}$ each independently are hydrogen or $C_{1-4}$alkyl; or $R^{9b}$ and $R^{10b}$ are taken together with the nitrogen to which they are attached to form a saturated monocyclic 4, 5, 6 or 7-membered heterocycle which may further contain one additional heteroatom selected from O, S, S(=O)$_p$ or N; and which heterocycle may optionally be substituted with 1, 2 or 3 substituents each independently selected from the group consisting of halo and $C_{1-4}$alkyl;

p is 1 or 2;

or a pharmaceutically acceptable addition salt or a solvate thereof.

2. The compound according to claim 1, wherein $R^1$ is —$Ar^1$ or —O—$Ar^1$;

$Ar^1$ is phenyl, pyridinyl, indazolyl, pyrazolyl, indolyl, imidazolyl, benzimidazolyl, thienyl, benzo[b]thienyl, benzofuranyl, 1H-pyrrolo[2,3-b]pyridinyl, imidazo[1,2-a]pyridinyl, 1,3-dihydro-1-oxo-2H-isoindolyl, 1,3-dihydro-1,3-dioxo-2H-isoindolyl or 2,3-dihydro-2-oxo-1H-benzimidazolyl; each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ and $C_{1-4}$alkyl substituted with one or more halo atoms;

$Ar^2$ is phenyl, thienyl, furanyl, isoxazolyl or pyrazolyl; each optionally substituted with one $C_{1-4}$alkyl group;

$R^2$ and $R^3$ are the same and are hydrogen or fluoro;

A is CH or N;

$R^4$ is hydrogen or fluoro;

$R^5$ is hydrogen, —$OR^7$ or —O—$(CH_2)_m$—O—$C_{1-4}$alkyl;

$R^6$ is —$OR^8$ or —O—$(CH_2)_m$—O—$C_{1-4}$alkyl;

or $R^5$ and $R^6$ are taken together to form the bivalent radical —O—$CH_2$—O—;

m is 1, 2, 3 or 4;

$R^7$ is $C_{1-4}$alkyl;

$R^8$ is $C_{1-4}$alkyl optionally substituted with one $NR^{9b}R^{10b}$;

$R^{9b}$ and $R^{10b}$ are taken together with the nitrogen to which they are attached to form morpholinyl.

3. The compound according to claim 1, wherein $R^1$ is —$Ar^1$;

$Ar^1$ is phenyl, pyridinyl, indazolyl, pyrazolyl, indolyl, benzimidazolyl, thienyl, benzo[b]thienyl, benzofuranyl, 1H-pyrrolo[2,3-b]pyridinyl, imidazo[1,2-a]pyridinyl, or 2,3-dihydro-2-oxo-1H-benzimidazolyl;

each optionally substituted with 1, 2 or 3 substituents each independently selected from the group consisting of $C_{1-4}$alkyl, $C_{1-4}$alkylcarbonyl, $C_{1-4}$alkyloxy, halo, $Ar^2$ and $C_{1-4}$alkyl substituted with one or more halo atoms;

$Ar^2$ is phenyl, thienyl, furanyl, isoxazolyl, or pyrazolyl; each optionally substituted with 1, 2 or 3 $C_{1-4}$alkyl groups;

$R^2$ and $R^3$ are the same and are hydrogen or fluoro;

A is CH;

$R^4$ is hydrogen or fluoro;

$R^5$ is —$OR^7$;

$R^6$ is —$OR^8$;

or $R^5$ and $R^6$ are taken together to form the bivalent radical —O—$CH_2$—O—;

$R^7$ is $C_{1-4}$alkyl;

$R^8$ is $C_{1-4}$alkyl optionally substituted with one morpholinyl.

4. The compound according to claim 1 wherein $R^1$ is —$Ar^1$;

$Ar^1$ is phenyl or indolyl;

each optionally substituted with 1 or 2 substituents each independently selected from the group consisting of $C_{1-4}$alkyl and halo;

$R^2$ and $R^3$ are the same and are hydrogen;

A is CH;

$R^4$ is hydrogen or fluoro;

$R^5$ is methoxy;

$R^6$ is $OR^8$;

$R^8$ is $C_{1-4}$alkyl optionally substituted with one morpholinyl.

5. The compound according to claim 1, wherein $R^1$ is —$Ar^1$.

6. The compound according to claim 5, wherein $Ar^1$ is phenyl, indol-1-yl or indol-3-yl;

each optionally substituted with one or two substituents selected from the group consisting of methyl and fluoro.

7. The compound according to claim 1, wherein A is CH.

8. The compound according to claim 1, wherein $R^5$ and $R^6$ are methoxy.

9. The compound according to claim 1, wherein $R^4$ is hydrogen.

10. The compound according to claim 1 wherein the compound is selected from the group consisting of

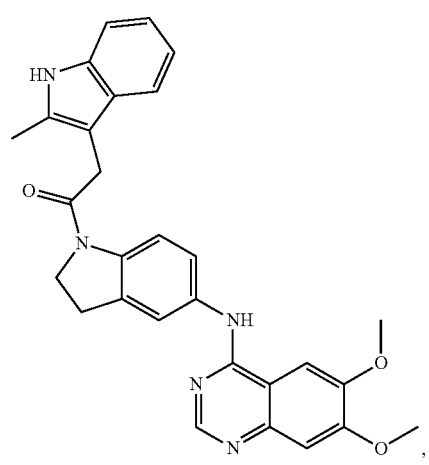

-continued
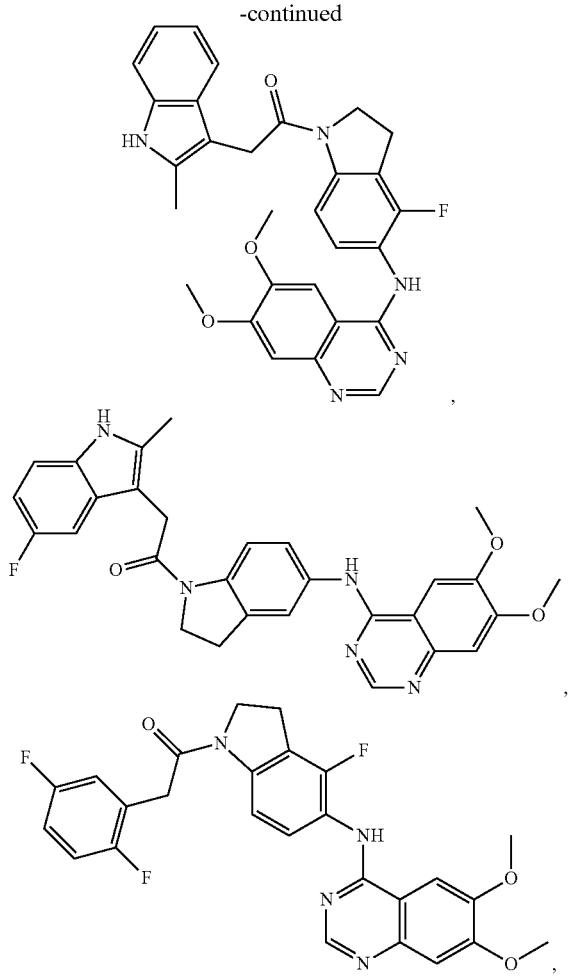
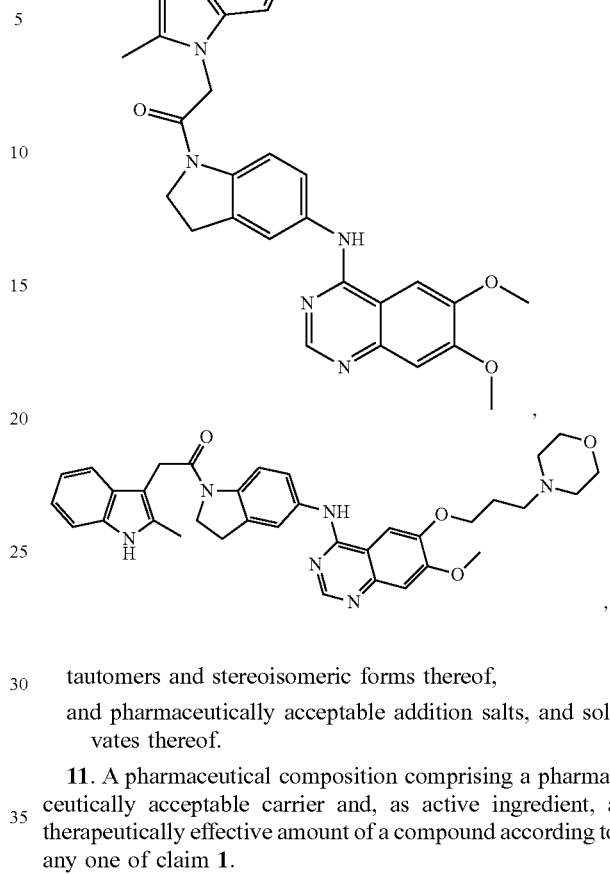
tautomers and stereoisomeric forms thereof,
and pharmaceutically acceptable addition salts, and solvates thereof.
11. A pharmaceutical composition comprising a pharmaceutically acceptable carrier and, as active ingredient, a therapeutically effective amount of a compound according to any one of claim 1.
* * * * *